US007462482B2

(12) United States Patent
Malik et al.

(10) Patent No.: US 7,462,482 B2
(45) Date of Patent: Dec. 9, 2008

(54) HUMAN SMOOTH MUSCLE MYOSIN HEAVY CHAIN

(75) Inventors: Fady Malik, Burlingame, CA (US); Christophe Beraud, Palm Springs, CA (US); Richard Freedman, San Mateo, CA (US); Andrew Craven, Belmont, CA (US); Roman Sakowicz, Foster City, CA (US); James Hartman, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 176 days.

(21) Appl. No.: 10/486,057

(22) PCT Filed: Aug. 9, 2002

(86) PCT No.: PCT/US02/25563

§ 371 (c)(1),
(2), (4) Date: Feb. 6, 2004

(87) PCT Pub. No.: WO03/014323

PCT Pub. Date: Feb. 20, 2003

(65) Prior Publication Data

US 2005/0130143 A1 Jun. 16, 2005

Related U.S. Application Data

(63) Continuation-in-part of application No. 09/927,597, filed on Aug. 10, 2001, now Pat. No. 6,974,688.

(51) Int. Cl.
*C12N 1/20* (2006.01)
*C12N 15/00* (2006.01)
*C07H 21/04* (2006.01)
*C12N 9/16* (2006.01)

(52) U.S. Cl. ............ 435/325; 435/410; 435/252.3; 435/254.11; 435/320.1; 435/196; 536/23.1; 536/23.2; 536/23.5; 536/24.31

(58) Field of Classification Search ............ None
See application file for complete search history.

(56) References Cited

U.S. PATENT DOCUMENTS 6,197,512 B1 3/2001 Bandman et al.
6,593,304 B1 * 7/2003 Hasegawa et al. ............ 514/44
6,974,688 B2 12/2005 Malik et al.

FOREIGN PATENT DOCUMENTS

WO  WO 96/23069 A1  1/1996
WO  WO 00/26372 A1  5/2000
WO  WO 03/014323 A2  2/2003
WO  WO 03/014323 A3  9/2004

OTHER PUBLICATIONS

Babij et al. (1991) Proc Natl Acad Sci 88:10676-10680.*
dos Remedios et al., Physiol Rev. 83:433-73, 2003.*
Guo et al., Proc Natl Acad Sci 101:9205-9210, 2004.*
Hult et al., Curr Opin Biotechnol 14:395-400, 2003.*
Definition of "ATPase" in the "Encyclopedia of Molecular Biology" (Creighton, Ed., John Wiley and Sons, Inc., New York, 1999, pp. 1-2.*
Dang et al. "Gene Therapy and Translational Cancer Research", Clin Cancer Res 5:471-474, 1999.*
Branden et al. *Introduction to Protein Structure*, 1991, p. 247, Garland Publishing, Inc. New York.
Castilla, L.H. et al. "The Fusion Gene Cbfb-MYH11 Blocks Myeloid Differentiation and Predisposes Mice to Accute Myelomonocytic Leukemia" *Nat. Gent.*, Oct. 1999, pp. 144-146, vol. 23, No. 2.
Deng, Z. et al. "Smooth Muscle Myosin Heavy Chain Locus (MYH11) maps to 16p13.13-p13.12 and Establishes a New Region of Conserved Synteny Between Human 16p and Mouse 16" *Genomics*, Oct. 1993, pp. 156-159, vol. 18, No. 1.
GenBank Accession No. AB020673 (gi: 4240220), Feb. 1999.
GenBank Accession No. AC024120 (gi: 21703573), Feb. 2000.
GenBank Accession No. AF001548 (gi: 2104552), Apr. 1997.
GenPept Accession No. A41604 (gi: 109322), Apr. 1993.
GenPept Accession No. P35749 (gi: 13432177), Mar. 2001.
Liu, P. et al. "Fusion Between Transcription Factor CBF beta/PEBP2 beta and a Myosin Heavy Chain in Acute Myeloid Leukemia" *Science*, Aug. 20, 1993; pp. 1041-1044, vol. 261, No. 5124.
Loftus, B.J. et al. "Genome Duplications and other Features in 12 Mb of DNA Sequence from Human Chromosome 16p and 16q", *Genomics*, Sep. 1999, pp. 295-308.
Matsuoka et al. "Human Smooth Muscle Myosin Heavy Chain Gene Mapped to Chromosomal Region 16q12", *Am. Journal. Med. Genet.*, 1993, pp. 61-67, vol. 46, No. 1.
Nagase, T. et al. "Prediction of the Coding Sequences of Unidentified Human Genes. XII. The Complete Sequences of 100 New cDNA From Brain Which Code for Large Protein in Vitro." *DNA Research*, Dec. 1998, pp. 355-364.
Witkowski et al. "Conversion of a β-Ketoacyl Synthase to a Malonyl Decarboxylase by Replacement of the Active-Site Cysteine with Glutamine" *Biochemistry*, 1999, pp. 11643-11650, vol. 38.
Abaza, Mohammed-Salah & Atassi, M. Zouhair "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin" *Journal of Protein Chemistry*, 1992, pp. 433-444, vol. 11, No. 5.
Creighton, T.E. *Protein Structure: A Practical Approach*, 1989, pp. 184-186, IRL PRess at Oxford University Press.
Office Action (including Form 892) of Mar. 19, 2004 in granted US patent 6,974,688.
Office Action (including form 892) of Sep. 23, 2003 in granted US patent 6,974,688.

(Continued)

Primary Examiner—David J Steadman
(74) Attorney, Agent, or Firm—Townsend and Townsend and Crew LLP

(57) ABSTRACT

The invention provides novel compositions, methods, and uses of hSMMyHC polypeptides and polynucleotides.

7 Claims, 27 Drawing Sheets

OTHER PUBLICATIONS

Notice of Allowance and Fee(s) Due (4 pp.): Notice of Allowability (10 pp.); Form 892 (1p.) of Sep. 22, 2004 in granted US patent 6,974,688.

Locus Link Report: Locus ID: 4629; MYHII: myosin, heavy polypeptide 11, smooth muscle; 5 pages; NCBI; Nov. 2001.

Manstein, D.J., et al.; Overexpression of myosin motor domains in Dictyostelium: screening of transformants and purification of the affinity tagged protein; J Mus Res Cell Mot; 16:325-332; 1995.

OMIM ID No. 160745; Myosin, Heavy Chain 11, Smooth Muscle; MYH11; Nov. 2001.

* cited by examiner

```
   1  ATGGCGCAGA AGGGCCAACT CAGTGACGAT GAGAAGTTCC TCTTTGTGGA
  51  CAAAAACTTC ATCAACAGCC CAGTGGCCCA GGCTGACTGG GCCGCCAAGA
 101  GACTCGTCTG GGTCCCCTCG AGAAGCAGG GCTTCGAGGC AGCCAGCATT
 151  AAGGAGGAGA AGGGGGATGA GGTGGTTGTG GAGCTGGTGG AGAATGGCAA
 201  GAAGGTCACG GTTGGGAAAG ATGACATCCA GAAGATGAAC CCACCCAAGT
 251  TCTCCAAGGT GGAGGACATG GCGGAGCTGA CGTGCCTCAA CGAAGCCTCC
 301  GTGCTACACA ACCTGAGGGA GCGGTACTTC TCAGGGCTAA TATATACGTA
 351  CTCTGGCCTC TTCTGCGTGG TGGTCAACCC CTATAAACAC CTGCCCATCT
 401  ACTCGGAGAA GATCGTCGAC ATGTACAAGG GCAAGAAGAG GCACGAGATG
 451  CCGCCTCACA TCTACGCCAT CGCAGACACG GCCTACCGGA GCATGCTTCA
 501  AGATCGGGAG GACCAGTCCA TTCTATGCAC AGGCGAGTCT GGAGCCGGGA
 551  AAACCGAAAA CACCAAGAAG GTCATTCAGT ACCTGGCCGT GGTGGCCTCC
 601  TCCCACAAGG GCAAGAAAGA CACAAGTATC ACGCAAGGCC ATCTTTTGC
 651  CTACGGAGAG CTGGAAAAGC AGCTTCTACA AGCAAACCCG ATTCTGGAGG
 701  CTTTCGGCAA CGCCAAAACA GTGAAGAACG ACAACTCCTC ACGATTCGGC
 751  AAATTCATCC GCATCAACTT CGACGTCACG GGTTACATCG TGGGAGCCAA
 801  CATTGAGACC TATCTGCTAG AAAAATCACG GGCAATTCGC CAAGCCAGAG
 851  ACGAGAGGAC ATTCCACATC TTTTACTACA TGATTGCTGG AGCCAAGGAG
 901  AAGATGAGAA GTGACTTGCT TTTGGAGGGC TTCAACAACT ACACCTTCCT
 951  CTCCAATGGC TTTGTGCCCA TCCCAGCAGC CCAGGATGAT GAGATGTTCC
1001  AGGAAACCGT GGAGGCCATG GCAATCATGG GTTTCAGCGA GGAGGAGCAG
1051  CTATCCATAT TGAAGGTGGT ATCATCGGTC CTGCAGCTTG GAAATATCGT
1101  CTTCAAGAAG GAAAGAAACA CAGACCAGGC GTCCATGCCA GATAACACAG
1151  CTGCTCAGAA AGTTTGCCAC CTCATGGGAA TTAATGTGAC AGATTTCACC
1201  AGATCCATCC TCACTCCTCG TATCAAGGTT GGGCGAGATG TGGTACAGAA
1251  AGCTCAGACA AAAGAACAGG CTGACTTTGC TGTAGAGGCT TTGGCCAAGG
1301  CAACATATGA GCGCCTTTTC CGCTGGATAC TCACCCGCGT GAACAAAGCC
1351  CTGGACAAGA CCCATCGGCA AGGGGCTTCC TTCCTGGGGA TCCTGGATAT
1401  AGCTGGATTT GAGATCTTTG AGGTGAACTC CTTCGAGCAG CTGTGCATCA
1451  ACTACACCAA CGAGAAGCTG CAGCAGCTCT TCAACCACAC CATGTTCATC
```

FIG. 1A

```
1501  CTGGAGCAGG AGGAGTACCA GCGCGAGGGC ATCGAGTGGA ACTTCATCGA
1551  CTTTGGGCTG GACCTACAGC CCTGCATCGA GCTCATCGAG CGACCGAACA
1601  ACCCTCCAGG TGTGCTGGCC CTGCTGGACG AGGAATGCTG GTTCCCCAAA
1651  GCCACGGACA AGTCTTTCGT GGAGAAGCTG TGCACGGAGC AGGGCAGCCA
1701  CCCCAAGTTC CAGAAGCCCA AGCAGCTCAA GGACAAGACT GAGTTCTCCA
1751  TCATCCATTA TGCTGGGAAG GTGGACTATA ATGCGAGTGC CTGGCTGACC
1801  AAGAATATGG ACCCGCTGAA TGACAACGTG ACTTCCCTGC TCAATGCCTC
1851  CTCCGACAAG TTTGTGGCCG ACCTGTGGAA GGACGTGGAC CGCATCGTGG
1901  GCCTGGACCA GATGGCCAAG ATGACGGAGA GCTCGCTGCC CAGCGCCTCC
1951  AAGACCAAGA AGGGCATGTT CCGCACAGTG GGGCAGCTGT ACAAGGAGCA
2001  GCTGGGCAAG CTGATGACCA CGCTACGCAA CACCACGCCC AACTTCGTGC
2051  GCTGCATCAT CCCCAACCAC GAGAAGAGGT CCGGCAAGCT GGATGCGTTC
2101  CTGGTGCTGG AGCAGCTGCG GTGCAATGGG GTGCTGGAAG GCATTCGCAT
2151  CTGCCGGCAG GGCTTCCCCA ACCGGATCGT CTTCCAGGAG TTCCGCCAAC
2201  GCTACGAGAT CCTGGCGGCG AATGCCATCC CCAAAGGCTT CATGGACGGG
2251  AAGCAGGCCT GCATTCTCAT GATCAAAGCC CTGGAACTTG ACCCCAACTT
2301  ATACAGGATA GGGCAGAGCA AAATCTTCTT CCGAACTGGC GTCCTGGCCC
2351  ACCTAGAGGA GGAGCGAGAT TTGAAGATCA CCGATGTCAT CATGGCCTTC
2401  CAGGCGATGT GTCGTGGCTA CTTGGCCAGA AAGGCTTTTG CCAAGAGGCA
2451  GCAGCAGCTG ACCGCCATGA AGGTGATTCA GAGGAACTGC GCCGCCTACC
2501  TCAAGCTGCG GAACTGGCAG TGGTGGAGGC TTTTCACCAA AGTGAAGCCA
2551  CTGCTGCAGG TGACACGGCA GGAGGAGGAG ATGCAGGCCA AGGAGGATGA
2601  ACTGCAGAAG ACCAAGGAGC GGCAGCAGAA GGCAGAGAAT GAGCTTAAGG
2651  AGCTGGAACA GAAGCACTCG CAGCTGACCG AGGAGAAGAA CCTGCTACAG
2701  GAACAGCTGC AGGCAGAGAC AGAGCTGTAT GCAGAGGCTG AGGAGATGCG
2751  GGTGCGGCTG GCGGCCAAGA AGCAGGAGCT GGAGGAGATA CTGCATGAGA
2801  TGGAGGCCCG CCTGGAGGAG GAGGAAGACA GGGCCAGCA GCTACAGGCT
2851  GAAAGGAAGA AGATGGCCCA GCAGATGCTG GACCTTGAAG AACAGCTGGA
2901  GGAGGAGGAA GCTGCCAGGC AGAAGCTGCA ACTTGAGAAG GTCACGGCTG
2951  AGGCCAAGAT CAAGAAACTG GAGGATGAGA TCCTGGTCAT GGATGATCAG
3001  AACAATAAAC TATCAAAAGA ACGAAAACTC CTTGAGGAGA GGATTAGTGA
```

FIG. 1B

```
3051  CTTAACGACA AATCTTGCAG AAGAGGAAGA AAAGGCCAAG AATCTTACCA
3101  AGCTGAAAAA CAAGCATGAA TCTATGATTT CAGAACTGGA AGTGCGGCTA
3151  AAGAAGGAAG AGAAGAGCCG ACAGGAGCTG GAGAAGCTGA AACGGAAGCT
3201  GGAGGGTGAT GCCAGCGACT TCCACGAGCA GATCGCTGAC CTCCAGGCGC
3251  AGATCGCAGA GCTCAAGATG CAGCTGGCCA AGAAGGAGGA GGAGCTGCAG
3301  GCGGCCCTGG CCAGGCTTGA CGATGAAATC GCTCAGAAGA ACAATGCCCT
3351  GAAGAAGATC CGGGAGCTGG AGGGCCACAT CTCAGACCTC CAGGAGGACC
3401  TGGACTCAGA GCGGGCCGCC AGGAACAAGG CTGAAAAGCA GAAGCGAGAC
3451  CTCGGCGAGG AGCTGGAGGC CCTAAAGACA GAGCTGGAAG ACACACTGGA
3501  CAGCACAGCC ACTCAGCAGG AGCTCAGGGC CAAGAGGGAG CAGGAGGTGA
3551  CGGTGCTGAA GAAGGCCCTG GATGAAGAGA CGCGGTCCCA TGAGGCTCAG
3601  GTCCAGGAGA TGAGGCAGAA ACACGCACAG GCGGTGGAGG AGCTCACAGA
3651  GCAGCTTGAG CAGTTCAAGA GGGCCAAGGC GAACCTAGAC AAGAATAAGC
3701  AGACGCTGGA GAAAGAGAAC GCAGACCTGG CCGGGGAGCT GCGGGTCCTG
3751  GGCCAGGCCA AGCAGGAGGT GGAACATAAG AAGAAGAAGC TGGAGGCGCA
3801  GGTGCAGGAG CTGCAGTCCA AGTGCAGCGA TGGGGAGCGG GCCCGGGCGG
3851  AGCTCAATGA CAAAGTCCAC AAGCTGCAGA ATGAAGTTGA GAGCGTCACA
3901  GGGATGCTTA ACGAGGCCGA GGGGAAGGCC ATTAAGCTGG CCAAGGACGT
3951  GGCGTCCCTC AGTTCCCAGC TCCAGGACAC CCAGGAGCTG CTTCAAGAAG
4001  AAACCCGGCA GAAGCTCAAC GTGTCTACGA AGCTGCGCCA GCTGGAGGAG
4051  GAGCGGAACA GCCTGCAAGA CCAGCTGGAC GAGGAGATGG AGGCCAAGCA
4101  GAACCTGGAG CGCCACATCT CCACTCTCAA CATCCAGCTC TCCGACTCGA
4151  AGAAGAAGCT GCAGGACTTT GCCAGCACCG TGGAAGCTCT GGAAGAGGGG
4201  AAGAAGAGGT TCCAGAAGGA GATCGAGAAC CTCACCCAGC AGTACGAGGA
4251  GAAGGCGGCC GCTTATGATA AACTGGAAAA GACCAAGAAC AGGCTTCAGC
4301  AGGAGCTGGA CGACCTGGTT GTTGATTTGG ACAACCAGCG GCAACTCGTG
4351  TCCAACCTGG AAAAGAAGCA GAGGAAATTT GATCAGTTGT TAGCCGAGGA
4401  GAAAAACATC TCTTCCAAAT ACGCGGATGA GAGGGACAGA GCTGAGGCAG
4451  AAGCCAGGGA GAAGGAAACC AAGGCCCTGT CCCTGGCTCG GGCCCTTGAA
4501  GAGGCCTTGG AAGCCAAAGA GGAACTCGAG CGGACCAACA AAATGCTCAA
4551  AGCCGAAATG GAAGACCTGG TCAGCTCCAA GGATGACGTG GGCAAGAACG
```

FIG. 1C

```
4601  TCCATGAGCT GGAGAAGTCC AAGCGGGCCC TGGAGACCCA GATGGAGGAG

4651  ATGAAGACGC AGCTGGAAGA GCTGGAGGAC GAGCTGCAAG CCACGGAGGA

4701  CGCCAAACTG CGGCTGGAAG TCAACATGCA GGCGCTCAAG GGCCAGTTCG

4751  AAAGGGATCT CCAAGCCCGG GACGAGCAGA ATGAGGAGAA GAGGAGGCAA

4801  CTGCAGAGAC AGCTTCACGA GTATGAGACG GAACTGGAAG ACGAGCGAAA

4851  GCAACGTGCC CTGGCAGCTG CAGCAAAGAA GAAGCTGGAA GGGGACCTGA

4901  AAGACCTGGA GCTTCAGGCC GACTCTGCCA TCAAGGGGAG GGAGGAAGCC

4951  ATCAAGCAGC TACGCAAACT GCAGGCTCAG ATGAAGGACT TCAAAGAGA

5001  GCTGGAAGAT GCCCGTGCCT CCAGAGATGA GATCTTTGCC ACAGCCAAAG

5051  AGAATGAGAA GAAAGCCAAG AGCTTGGAAG CAGACCTCAT GCAGCTACAA

5101  GAGGACCTCG CCGCCGCTGA GAGGGCTCGC AAACAAGCGG ACCTCGAGAA

5151  GGAGGAACTG GCAGAGGAGC TGGCCAGTAG CCTGTCGGGA AGGAACGCAC

5201  TCCAGGACGA GAAGCGCCGC CTGGAGGCCC GGATCGCCCA GCTGGAGGAG

5251  GAGCTGGAGG AGGAGCAGGG CAACATGGAG GCCATGAGCG ACCGGGTCCG

5301  CAAAGCCACA CAGCAGGCCG AGCAGCTCAG CAACGAGCTG GCCACAGAGC

5351  GCAGCACGGC CCAGAAGAAT GAGAGTGCCC GGCAGCAGCT CGAGCGGCAG

5401  AACAAGGAGC TCCGGAGCAA GCTCCACGAG ATGGAGGGGG CCGTCAAGTC

5451  CAAGTTCAAG TCCACCATCG CGGCGCTGGA GGCCAAGATT GCACAGCTGG

5501  AGGAGCAGGT CGAGCAGGAG GCCAGAGAGA ACAGGCGGC CACCAAGTCG

5551  CTGAAGCAGA AAGACAAGAA GCTGAAGGAA ATCTTGCTGC AGGTGGAGGA

5601  CGAGCGCAAG ATGGCCGAGC AGTACAAGGA GCAGGCAGAG AAAGGCAATG

5651  CCAGGGTCAA GCAGCTCAAG AGGCAGCTGG AGGAGGCAGA GGAGGAGTCC

5701  CAGCGCATCA ACGCCAACCG CAGGAAGCTG CAGCGGGAGC TGGATGAGGC

5751  CACGGAGAGC AACGAGGCCA TGGGCCGCGA GGTGAACGCA CTCAAGAGCA

5801  AGCTCAGAGG GCCCCCCCCA CAGGAAACTT CGCAG
```

FIG. 1D

```
   1  MAQKGQLSDD  EKFLFVDKNF  INSPVAQADW  AAKRLVWVPS  EKQGPEAASI
  51  KEEKGDEVVV  ELVENGKKVT  VGKDDIQKMN  PPKFSKVEDM  AELTCLNEAS
 101  VLHNLRERYF  SGLIYTYSGL  FCVVVNPYKH  LPIYSEKIVD  MYKGKKRHEM
 151  PPHIYAIADT  AYRSMLQDRE  DQSILCTGES  GAGKTENTKK  VIQYLAVVAS
 201  SHKGKKDTSI  TQGPSFAYGE  LEKQLLQANP  ILEAFGNAKT  VKNDNSSRFG
 251  KFIRINFDVT  GYIVGANIET  YLLEKSRAIR  QARDERTFHI  FYYMIAGAKE
 301  KMRSDLLLEG  FNNYTFLSNG  FVPIPAAQDD  EMFQETVEAM  AIMGFSEEEQ
 351  LSILKVVSSV  LQLGNIVFKK  ERNTDQASMP  DNTAAQKVCH  LMGINVTDFT
 401  RSILTPRIKV  GRDVVQKAQT  KEQADFAVEA  LAKATYERLF  RWILTRVNKA
 451  LDKTHRQGAS  FLGILDIAGF  EIFEVNSFEQ  LCINYTNEKL  QQLFNHTMFI
 501  LEQEEYQREG  IEWNFIDFGL  DLQPCIELIE  RPNNPPGVLA  LLDEECWFPK
 551  ATDKSFVEKL  CTEQGSHPKF  QKPKQLKDKT  EFSIIHYAGK  VDYNASAWLT
 601  KNMDPLNDNV  TSLLNASSDK  FVADLWKDVD  RIVGLDQMAK  MTESSLPSAS
 651  KTKKGMFRTV  GQLYKEQLGK  LMTTLRNTTP  NFVRCIIPNH  EKRSGKLDAF
 701  LVLEQLRCNG  VLEGIRICRQ  GFPNRIVFQE  FRQRYEILAA  NAIPKGFMDG
 751  KQACILMIKA  LELDPNLYRI  GQSKIFFRTG  VLAHLEEERD  LKITDVIMAF
 801  QAMCRGYLAR  KAFAKRQQQL  TAMKVIQRNC  AAYLKLRNWQ  WWRLFTKVKP
 851  LLQVTRQEEE  MQAKEDELQK  TKERQQKAEN  ELKELEQKHS  QLTEEKNLLQ
 901  EQLQAETELY  AEAEEMRVRL  AAKKQELEEI  LHEMEARLEE  EEDRGQQLQA
 951  ERKKMAQQML  DLEEQLEEEE  AARQKLQLEK  VTAEAKIKKL  EDEILVMDDQ
1001  NNKLSKERKL  LEERISDLTT  NLAEEEEKAK  NLTKLKNKHE  SMISELEVRL
1051  KKEEKSRQEL  EKLKRKLEGD  ASDFHEQIAD  LQAQIAELKM  QLAKKEEELQ
1101  AALARLDDEI  AQKNNALKKI  RELEGHISDL  QEDLDSERAA  RNKAEKQKRD
1151  LGEELEALKT  ELEDTLDSTA  TQQELRAKRE  QEVTVLKKAL  DEETRSHEAQ
1201  VQEMRQKHAQ  AVEELTEQLE  QFKRAKANLD  KNKQTLEKEN  ADLAGELRVL
1251  GQAKQEVEHK  KKKLEAQVQE  LQSKCSDGER  ARAELNDKVH  KLQNEVESVT
1301  GMLNEAEGKA  IKLAKDVASL  SSQLQDTQEL  LQEETRQKLN  VSTKLRQLEE
1351  ERNSLQDQLD  EEMEAKQNLE  RHISTLNIQL  SDSKKKLQDF  ASTVEALEEG
1401  KKRFQKEIEN  LTQQYEEKAA  AYDKLEKTKN  RLQQELDDLV  VDLDNQRQLV
1451  SNLEKKQRKF  DQLLAEEKNI  SSKYADERDR  AEAEAREKET  KALSLARALE
1501  EALEAKEELE  RTNKMLKAEM  EDLVSSKDDV  GKNVHELEKS  KRALETQMEE
```

FIG. 2A

```
1551  MKTQLEELED  ELQATEDAKL  RLEVNMQALK  GQFERDLQAR  DEQNEEKRRQ

1601  LQRQLHEYET  ELEDERKQRA  LAAAAKKKLE  GDLKDLELQA  DSAIKGREEA

1651  IKQLRKLQAQ  MKDFQRELED  ARASRDEIFA  TAKENEKKAK  SLEADLMQLQ

1701  EDLAAAERAR  KQADLEKEEL  AEELASSLSG  RNALQDEKRR  LEARIAQLEE

1751  ELEEEQGNME  AMSDRVRKAT  QQAEQLSNEL  ATERSTAQKN  ESARQQLERQ

1801  NKELRSKLHE  MEGAVKSKFK  STIAALEAKI  AQLEEQVEQE  AREKQAATKS

1851  LKQKDKKLKE  ILLQVEDERK  MAEQYKEQAE  KGNARVKQLK  RQLEEAEEES

1901  QRINANRRKL  QRELDEATES  NEAMGREVNA  LKSKLRGPPP  QETSQ
```

FIG. 2B

```
   1  ATGGCGCAGA AGGGCCAACT CAGTGACGAT GAGAAGTTCC TCTTTGTGGA
  51  CAAAAACTTC ATCAACAGCC CAGTGGCCCA GGCTGACTGG GCCGCCAAGA
 101  GACTCGTCTG GGTCCCCTCG GAGAAGCAGG GCTTCGAGGC AGCCAGCATT
 151  AAGGAGGAGA AGGGGGATGA GGTGGTTGTG GAGCTGGTGG AGAATGGCAA
 201  GAAGGTCACG GTTGGGAAAG ATGACATCCA GAAGATGAAC CCACCCAAGT
 251  TCTCCAAGGT GGAGGACATG GCGGAGCTGA CGTGCCTCAA CGAAGCCTCC
 301  GTGCTACACA ACCTGAGGGA GCGGTACTTC TCAGGGCTAA TATATACGTA
 351  CTCTGGCCTC TTCTGCGTGG TGGTCAACCC CTATAAACAC CTGCCCATCT
 401  ACTCGGAGAA GATCGTCGAC ATGTACAAGG GCAAGAAGAG GCACGAGATG
 451  CCGCCTCACA TCTACGCCAT CGCAGACACG GCCTACCGGA GCATGCTTCA
 501  AGATCGGGAG GACCAGTCCA TTCTATGCAC AGGCGAGTCT GGAGCCGGGA
 551  AAACCGAAAA CACCAAGAAG GTCATTCAGT ACCTGGCCGT GGTGGCCTCC
 601  TCCCACAAGG GCAAGAAAGA CACAAGTATC ACGCAAGGCC ATCTTTTGC
 651  CTACGGAGAG CTGGAAAAGC AGCTTCTACA AGCAAACCCG ATTCTGGAGG
 701  CTTTCGGCAA CGCCAAAACA GTGAAGAACG ACAACTCCTC ACGATTCGGC
 751  AAATTCATCC GCATCAACTT CGACGTCACG GGTTACATCG TGGGAGCCAA
 801  CATTGAGACC TATCTGCTAG AAAAATCACG GGCAATTCGC CAAGCCAGAG
 851  ACGAGAGGAC ATTCCACATC TTTTACTACA TGATTGCTGG AGCCAAGGAG
 901  AAGATGAGAA GTGACTTGCT TTTGGAGGGC TTCAACAACT ACACCTTCCT
 951  CTCCAATGGC TTTGTGCCCA TCCCAGCAGC CAGGATGAT GAGATGTTCC
1001  AGGAAACCGT GGAGGCCATG GCAATCATGG GTTTCAGCGA GGAGGAGCAG
1051  CTATCCATAT TGAAGGTGGT ATCATCGGTC CTGCAGCTTG AAATATCGT
1101  CTTCAAGAAG GAAAGAAACA CAGACCAGGC GTCCATGCCA GATAACACAG
1151  CTGCTCAGAA AGTTTGCCAC CTCATGGGAA TTAATGTGAC AGATTTCACC
1201  AGATCCATCC TCACTCCTCG TATCAAGGTT GGGCGAGATG TGGTACAGAA
1251  AGCTCAGACA AAAGAACAGG CTGACTTTGC TGTAGAGGCT TTGGCCAAGG
1301  CAACATATGA GCGCCTTTTC CGCTGGATAC TCACCCGCGT GAACAAAGCC
1351  CTGGACAAGA CCCATCGGCA AGGGGCTTCC TTCCTGGGGA TCCTGGATAT
1401  AGCTGGATTT GAGATCTTTG AGGTGAACTC CTTCGAGCAG CTGTGCATCA
1451  ACTACACCAA CGAGAAGCTG CAGCAGCTCT TCAACCACAC CATGTTCATC
1501  CTGGAGCAGG AGGAGTACCA GCGCGAGGGC ATCGAGTGGA ACTTCATCGA
```

FIG. 3A

```
1551  CTTTGGGCTG GACCTACAGC CCTGCATCGA GCTCATCGAG CGACCGAACA
1601  ACCCTCCAGG TGTGCTGGCC CTGCTGGACG AGGAATGCTG GTTCCCCAAA
1651  GCCACGGACA AGTCTTTCGT GGAGAAGCTG TGCACGGAGC AGGGCAGCCA
1701  CCCCAAGTTC CAGAAGCCCA AGCAGCTCAA GGACAAGACT GAGTTCTCCA
1751  TCATCCATTA TGCTGGGAAG GTGGACTATA ATGCGAGTGC CTGGCTGACC
1801  AAGAATATGG ACCCGCTGAA TGACAACGTG ACTTCCCTGC TCAATGCCTC
1851  CTCCGACAAG TTTGTGGCCG ACCTGTGGAA GGACGTGGAC CGCATCGTGG
1901  GCCTGGACCA GATGGCCAAG ATGACGGAGA GCTCGCTGCC CAGCGCCTCC
1951  AAGACCAAGA AGGGCATGTT CCGCACAGTG GGGCAGCTGT ACAAGGAGCA
2001  GCTGGGCAAG CTGATGACCA CGCTACGCAA CACCACGCCC AACTTCGTGC
2051  GCTGCATCAT CCCCAACCAC GAGAAGAGGT CCGGCAAGCT GGATGCGTTC
2101  CTGGTGCTGG AGCAGCTGCG GTGCAATGGG GTGCTGGAAG GCATTCGCAT
2151  CTGCCGGCAG GGCTTCCCCA ACCGGATCGT CTTCCAGGAG TTCCGCCAAC
2201  GCTACGAGAT CCTGGCGGCG AATGCCATCC CCAAAGGCTT CATGGACGGG
2251  AAGCAGGCCT GCATTCTCAT GATCAAAGCC CTGGAACTTG ACCCCAACTT
2301  ATACAGGATA GGGCAGAGCA AAATCTTCTT CCGAACTGGC GTCCTGGCCC
2351  ACCTAGAGGA GGAGCGAGAT TTGAAGATCA CCGATGTCAT CATGGCCTTC
2401  CAGGCGATGT GTCGTGGCTA CTTGGCCAGA AAGGCTTTTG CCAAGAGGCA
2451  GCAGCAGCTG ACCGCCATGA AGGTGATTCA GAGGAACTGC GCCGCCTACC
2501  TCAAGCTGCG GAACTGGCAG TGGTGGAGGC TTTTCACCAA AGTGAAGCCA
2551  CTGCTGCAGG TGACACGGCA GGAGGAGGAG ATGCAGGCCA AGGAGGATGA
2601  ACTGCAGAAG ACCAAGGAGC GGCAGCAGAA GGCAGAGAAT GAGCTTAAGG
2651  AGCTGGAACA GAAGCACTCG CAGCTGACCG AGGAGAAGAA CCTGCTACAG
2701  GAACAGCTGC AGGCAGAGAC AGAGCTGTAT GCAGAGGCTG AGGAGATGCG
2751  GGTGCGGCTG GCGGCCAAGA AGCAGGAGCT GGAGGAGATA CTGCATGAGA
2801  TGGAGGCCCG CCTGGAGGAG GAGGAAGACA GGGGCCAGCA GCTACAGGCT
2851  GAAAGGAAGA AGATGGCCCA GCAGATGCTG GACCTTGAAG AACAGCTGGA
2901  GGAGGAGGAA GCTGCCAGGC AGAAGCTGCA ACTTGAGAAG GTCACGGCTG
2951  AGGCCAAGAT CAAGAAACTG GAGGATGAGA TCCTGGTCAT GGATGATCAG
3001  AACAATAAAC TATCAAAAGA ACGAAAACTC CTTGAGGAGA GGATTAGTGA
3051  CTTAACGACA AATCTTGCAG AAGAGGAAGA AAAGGCCAAG AATCTTACCA
```

FIG. 3B

```
3101  AGCTGAAAAA CAAGCATGAA TCTATGATTT CAGAACTGGA AGTGCGGCTA
3151  AAGAAGGAAG AGAAGAGCCG ACAGGAGCTG GAGAAGCTGA AACGGAAGCT
3201  GGAGGGTGAT GCCAGCGACT TCCACGAGCA GATCGCTGAC CTCCAGGCGC
3251  AGATCGCAGA GCTCAAGATG CAGCTGGCCA GAAGGAGGA GGAGCTGCAG
3301  GCGGCCCTGG CCAGGCTTGA CGATGAAATC GCTCAGAAGA ACAATGCCCT
3351  GAAGAAGATC CGGGAGCTGG AGGGCCACAT CTCAGACCTC CAGGAGGACC
3401  TGGACTCAGA GCGGGCCGCC AGGAACAAGG CTGAAAAGCA GAAGCGAGAC
3451  CTCGGCGAGG AGCTGGAGGC CCTAAAGACA GAGCTGGAAG ACACACTGGA
3501  CAGCACAGCC ACTCAGCAGG AGCTCAGGGC CAAGAGGGAG CAGGAGGTGA
3551  CGGTGCTGAA GAAGGCCCTG GATGAAGAGA CGCGGTCCCA TGAGGCTCAG
3601  GTCCAGGAGA TGAGGCAGAA ACACGCACAG GCGGTGGAGG AGCTCACAGA
3651  GCAGCTTGAG CAGTTCAAGA GGGCCAAGGC GAACCTAGAC AAGAATAAGC
3701  AGACGCTGGA GAAAGAGAAC GCAGACCTGG CCGGGGAGCT GCGGGTCCTG
3751  GGCCAGGCCA AGCAGGAGGT GGAACATAAG AAGAAGAAGC TGGAGGCGCA
3801  GGTGCAGGAG CTGCAGTCCA AGTGCAGCGA TGGGGAGCGG GCCCGGGCGG
3851  AGCTCAATGA CAAAGTCCAC AAGCTGCAGA ATGAAGTTGA GAGCGTCACA
3901  GGGATGCTTA ACGAGGCCGA GGGGAAGGCC ATTAAGCTGG CCAAGGACGT
3951  GGCGTCCCTC AGTTCCCAGC TCCAGGACAC CCAGGAGCTG CTTCAAGAAG
4001  AAACCCGGCA GAAGCTCAAC GTGTCTACGA AGCTGCGCCA GCTGGAGGAG
4051  GAGCGGAACA GCCTGCAAGA CCAGCTGGAC GAGGAGATGG AGGCCAAGCA
4101  GAACCTGGAG CGCCACATCT CCACTCTCAA CATCCAGCTC TCCGACTCGA
4151  AGAAGAAGCT GCAGGACTTT GCCAGCACCG TGGAAGCTCT GGAAGAGGGG
4201  AAGAAGAGGT TCCAGAAGGA GATCGAGAAC CTCACCCAGC AGTACGAGGA
4251  GAAGGCGGCC GCTTATGATA AACTGGAAAA GACCAAGAAC AGGCTTCAGC
4301  AGGAGCTGGA CGACCTGGTT GTTGATTTGG ACAACCAGCG GCAACTCGTG
4351  TCCAACCTGG AAAAGAAGCA GAGGAAATTT GATCAGTTGT TAGCCGAGGA
4401  GAAAAACATC TCTTCCAAAT ACGCGGATGA GAGGGACAGA GCTGAGGCAG
4451  AAGCCAGGGA GAAGGAAACC AAGGCCCTGT CCCTGGCTCG GGCCCTTGAA
4501  GAGGCCTTGG AAGCCAAAGA GGAACTCGAG CGGACCAACA AAATGCTCAA
4551  AGCCGAAATG GAAGACCTGG TCAGCTCCAA GGATGACGTG GGCAAGAACG
4601  TCCATGAGCT GGAGAAGTCC AAGCGGGCCC TGGAGACCCA GATGGAGGAG
```

FIG. 3C

```
4651  ATGAAGACGC AGCTGGAAGA GCTGGAGGAC GAGCTGCAAG CCACGGAGGA
4701  CGCCAAACTG CGGCTGGAAG TCAACATGCA GGCGCTCAAG GCCAGTTCG
4751  AAAGGGATCT CCAAGCCCGG GACGAGCAGA ATGAGGAGAA GAGGAGGCAA
4801  CTGCAGAGAC AGCTTCACGA GTATGAGACG GAACTGGAAG ACGAGCGAAA
4851  GCAACGTGCC CTGGCAGCTG CAGCAAAGAA GAAGCTGGAA GGGGACCTGA
4901  AAGACCTGGA GCTTCAGGCC GACTCTGCCA TCAAGGGGAG GGAGGAAGCC
4951  ATCAAGCAGC TACGCAAACT GCAGGCTCAG ATGAAGGACT TTCAAAGAGA
5001  GCTGGAAGAT GCCCGTGCCT CCAGAGATGA GATCTTTGCC ACAGCCAAAG
5051  AGAATGAGAA GAAAGCCAAG AGCTTGGAAG CAGACCTCAT GCAGCTACAA
5101  GAGGACCTCG CCGCCGCTGA GAGGGCTCGC AAACAAGCGG ACCTCGAGAA
5151  GGAGGAACTG GCAGAGGAGC TGGCCAGTAG CCTGTCGGGA AGGAACGCAC
5201  TCCAGGACGA GAAGCGCCGC CTGGAGGCCC GGATCGCCCA GCTGGAGGAG
5251  GAGCTGGAGG AGGAGCAGGG CAACATGGAG GCCATGAGCG ACCGGGTCCG
5301  CAAAGCCACA CAGCAGGCCG AGCAGCTCAG CAACGAGCTG GCCACAGAGC
5351  GCAGCACGGC CCAGAAGAAT GAGAGTGCCC GGCAGCAGCT CGAGCGGCAG
5401  AACAAGGAGC TCCGGAGCAA GCTCCACGAG ATGGAGGGGG CCGTCAAGTC
5451  CAAGTTCAAG TCCACCATCG CGGCGCTGGA GGCCAAGATT GCACAGCTGG
5501  AGGAGCAGGT CGAGCAGGAG GCCAGAGAGA ACAGGCGGC CACCAAGTCG
5551  CTGAAGCAGA AAGACAAGAA GCTGAAGGAA ATCTTGCTGC AGGTGGAGGA
5601  CGAGCGCAAG ATGGCCGAGC AGTACAAGGA GCAGGCAGAG AAAGGCAATG
5651  CCAGGGTCAA GCAGCTCAAG AGGCAGCTGG AGGAGGCAGA GGAGGAGTCC
5701  CAGCGCATCA ACGCCAACCG CAGGAAGCTG CAGCGGGAGC TGGATGAGGC
5751  CACGGAGAGC AACGAGGCCA TGGGCCGCGA GGTGAACGCA CTCAAGAGCA
5801  AGCTCAGGCG AGGAAACGAG ACCTCTTTCG TTCCTTCTAG AAGGTCTGGA
5851  GGACGTAGAG TTATTGAAAA TGCAGATGGT TCTGAGGAGG AAACGGACAC
5901  TCGAGACGCA GACTTCAATG GAACCAAGGC CAGTGAA
```

FIG. 3D

```
   1  MAQKGQLSDD EKFLFVDKNF INSPVAQADW AAKRLVWVPS EKQGFEAASI
  51  KEEKGDEVVV ELVENGKKVT VGKDDIQKMN PPKFSKVEDM AELTCLNEAS
 101  VLHNLRERYF SGLIYTYSGL FCVVVNPYKH LPIYSEKIVD MYKGKKRHEM
 151  PPHIYAIADT AYRSMLQDRE DQSILCTGES GAGKTENTKK VIQYLAVVAS
 201  SHKGKKDTSI TQGPSFAYGE LEKQLLQANP ILEAFGNAKT VKNDNSSRFG
 251  KFIRINFDVT GYIVGANIET YLLEKSRAIR QARDERTFHI FYYMIAGAKE
 301  KMRSDLLLEG FNNYTFLSNG FVPIPAAQDD EMFQETVEAM AIMGFSEEEQ
 351  LSILKVVSSV LQLGNIVFKK ERNTDQASMP DNTAAQKVCH LMGINVTDFT
 401  RSILTPRIKV GRDVVQKAQT KEQADFAVEA LAKATYERLF RWILTRVNKA
 451  LDKTHRQGAS FLGILDIAGF EIFEVNSFEQ LCINYTNEKL QQLFNHTMFI
 501  LEQEEYQREG IEWNFIDFGL DLQPCIELIE RPNNPPGVLA LLDEECWFPK
 551  ATDKSFVEKL CTEQGSHPKF QKPKQLKDKT EFSIIHYAGK VDYNASAWLT
 601  KNMDPLNDNV TSLLNASSDK FVADLWKDVD RIVGLDQMAK MTESSLPSAS
 651  KTKKGMFRTV GQLYKEQLGK LMTTLRNTTP NFVRCIIPNH EKRSGKLDAF
 701  LVLEQLRCNG VLEGIRICRQ GFPNRIVFQE FRQRYEILAA NAIPKGFMDG
 751  KQACILMIKA LELDPNLYRI GQSKIFFRTG VLAHLEEERD LKITDVIMAF
 801  QAMCRGYLAR KAFAKRQQQL TAMKVIQRNC AAYLKLRNWQ WWRLFTKVKP
 851  LLQVTRQEEE MQAKEDELQK TKERQQKAEN ELKELEQKHS QLTEEKNLLQ
 901  EQLQAETELY AEAEEMRVRL AAKKQELEEI LHEMEARLEE EEDRGQQLQA
 951  ERKKMAQQML DLEEQLEEEE AARQKLQLEK VTAEAKIKKL EDEILVMDDQ
1001  NNKLSKERKL LEERISDLTT NLAEEEEKAK NLTKLKNKHE SMISELEVRL
1051  KKEEKSRQEL EKLKRKLEGD ASDFHEQIAD LQAQIAELKM QLAKKEEELQ
1101  AALARLDDEI AQKNNALKKI RELEGHISDL QEDLDSERAA RNKAEKQKRD
1151  LGEELEALKT ELEDTLDSTA TQQELRAKRE QEVTVLKKAL DEETRSHEAQ
1201  VQEMRQKHAQ AVEELTEQLE QFKRAKANLD KNKQTLEKEN ADLAGELRVL
1251  GQAKQEVEHK KKKLEAQVQE LQSKCSDGER ARAELNDKVH KLQNEVESVT
1301  GMLNEAEGKA IKLAKDVASL SSQLQDTQEL LQEETRQKLN VSTKLRQLEE
1351  ERNSLQDQLD EEMEAKQNLE RHISTLNIQL SDSKKKLQDF ASTVEALEEG
1401  KKRFQKEIEN LTQQYEEKAA AYDKLEKTKN RLQQELDDLV VDLDNQRQLV
1451  SNLEKKQRKF DQLLAEEKNI SSKYADERDR AEAEAREKET KALSLARALE
1501  EALEAKEELE RTNKMLKAEM EDLVSSKDDV GKNVHELEKS KRALETQMEE
```

FIG. 4A

```
1551    MKTQLEELED  ELQATEDAKL  RLEVNMQALK  GQFERDLQAR  DEQNEEKRRQ

1601    LQRQLHEYET  ELEDERKQRA  LAAAAKKKLE  GDLKDLELQA  DSAIKGREEA

1651    IKQLRKLQAQ  MKDFQRELED  ARASRDEIFA  TAKENEKKAK  SLEADLMQLQ

1701    EDLAAAERAR  KQADLEKEEL  AEELASSLSG  RNALQDEKRR  LEARIAQLEE

1751    ELEEEQGNME  AMSDRVRKAT  QQAEQLSNEL  ATERSTAQKN  ESARQQLERQ

1801    NKELRSKLHE  MEGAVKSKFK  STIAALEAKI  AQLEEQVEQE  AREKQAATKS

1851    LKQKDKKLKE  ILLQVEDERK  MAEQYKEQAE  KGNARVKQLK  RQLEEAEEES

1901    QRINANRRKL  QRELDEATES  NEAMGREVNA  LKSKLRRGNE  TSFVPSRRSG

1951    GRRVIENADG  SEEETDTRDA  DFNGTKASE
```

FIG. 4B

```
   1  ATGGCGCAGA AGGGCCAACT CAGTGACGAT GAGAAGTTCC TCTTTGTGGA
  51  CAAAAACTTC ATCAACAGCC CAGTGGCCCA GGCTGACTGG GCCGCCAAGA
 101  GACTCGTCTG GGTCCCCTCG AGAAGCAGG GCTTCGAGGC AGCCAGCATT
 151  AAGGAGGAGA AGGGGGATGA GGTGGTTGTG GAGCTGGTGG AGAATGGCAA
 201  GAAGGTCACG GTTGGGAAAG ATGACATCCA GAAGATGAAC CCACCCAAGT
 251  TCTCCAAGGT GGAGGACATG GCGGAGCTGA CGTGCCTCAA CGAAGCCTCC
 301  GTGCTACACA ACCTGAGGGA GCGGTACTTC TCAGGGCTAA TATATACGTA
 351  CTCTGGCCTC TTCTGCGTGG TGGTCAACCC CTATAAACAC CTGCCCATCT
 401  ACTCGGAGAA GATCGTCGAC ATGTACAAGG GCAAGAAGAG GCACGAGATG
 451  CCGCCTCACA TCTACGCCAT CGCAGACACG GCCTACCGGA GCATGCTTCA
 501  AGATCGGGAG GACCAGTCCA TTCTATGCAC AGGCGAGTCT GGAGCCGGGA
 551  AAACCGAAAA CACCAAGAAG GTCATTCAGT ACCTGGCCGT GGTGGCCTCC
 601  TCCCACAAGG GCAAGAAAGA CACAAGTATC ACGCAAGGCC CATCTTTTGC
 651  CTACGGAGAG CTGGAAAAGC AGCTTCTACA AGCAAACCCG ATTCTGGAGG
 701  CTTTCGGCAA CGCCAAAACA GTGAAGAACG ACAACTCCTC ACGATTCGGC
 751  AAATTCATCC GCATCAACTT CGACGTCACG GGTTACATCG TGGGAGCCAA
 801  CATTGAGACC TATCTGCTAG AAAAATCACG GGCAATTCGC CAAGCCAGAG
 851  ACGAGAGGAC ATTCCACATC TTTTACTACA TGATTGCTGG AGCCAAGGAG
 901  AAGATGAGAA GTGACTTGCT TTTGGAGGGC TTCAACAACT ACACCTTCCT
 951  CTCCAATGGC TTTGTGCCCA TCCCAGCAGC CCAGGATGAT GAGATGTTCC
1001  AGGAAACCGT GGAGGCCATG GCAATCATGG GTTTCAGCGA GGAGGAGCAG
1051  CTATCCATAT TGAAGGTGGT ATCATCGGTC CTGCAGCTTG GAAATATCGT
1101  CTTCAAGAAG GAAAGAAACA CAGACCAGGC GTCCATGCCA GATAACACAG
1151  CTGCTCAGAA AGTTTGCCAC CTCATGGGAA TTAATGTGAC AGATTTCACC
1201  AGATCCATCC TCACTCCTCG TATCAAGGTT GGGCGAGATG TGGTACAGAA
1251  AGCTCAGACA AAAGAACAGG CTGACTTTGC TGTAGAGGCT TTGGCCAAGG
1301  CAACATATGA GCGCCTTTTC CGCTGGATAC TCACCCGCGT GAACAAAGCC
1351  CTGGACAAGA CCCATCGGCA AGGGGCTTCC TTCCTGGGGA TCCTGGATAT
1401  AGCTGGATTT GAGATCTTTG AGGTGAACTC CTTCGAGCAG CTGTGCATCA
1451  ACTACACCAA CGAGAAGCTG CAGCAGCTCT TCAACCACAC CATGTTCATC
1501  CTGGAGCAGG AGGAGTACCA GCGCGAGGGC ATCGAGTGGA ACTTCATCGA
```

FIG. 5A

1551 CTTTGGGCTG GACCTACAGC CCTGCATCGA GCTCATCGAG CGACCGAACA

1601 ACCCTCCAGG TGTGCTGGCC CTGCTGGACG AGGAATGCTG GTTCCCCAAA

1651 GCCACGGACA AGTCTTTCGT GGAGAAGCTG TGCACGGAGC AGGGCAGCCA

1701 CCCCAAGTTC CAGAAGCCCA AGCAGCTCAA GGACAAGACT GAGTTCTCCA

1751 TCATCCATTA TGCTGGGAAG GTGGACTATA ATGCGAGTGC CTGGCTGACC

1801 AAGAATATGG ACCCGCTGAA TGACAACGTG ACTTCCCTGC TCAATGCCTC

1851 CTCCGACAAG TTTGTGGCCG ACCTGTGGAA GGACGTGGAC CGCATCGTGG

1901 GCCTGGACCA GATGGCCAAG ATGACGGAGA GCTCGCTGCC CAGCGCCTCC

1951 AAGACCAAGA AGGGCATGTT CCGCACAGTG GGGCAGCTGT ACAAGGAGCA

2001 GCTGGGCAAG CTGATGACCA CGCTACGCAA CACCACGCCC AACTTCGTGC

2051 GCTGCATCAT CCCCAACCAC GAGAAGAGGT CCGGCAAGCT GGATGCG

FIG. 5B

```
  1  MAQKGQLSDD  EKFLFVDKNF  INSPVAQADW  AAKRLVWVPS  EKQGFEAASI
 51  KEEKGDEVVV  ELVENGKKVT  VGKDDIQKMN  PPKFSKVEDM  AELTCLNEAS
101  VLHNLRERYF  SGLIYTYSGL  FCVVVNPYKH  LPIYSEKIVD  MYKGKKRHEM
151  PPHIYAIADT  AYRSMLQDRE  DQSILCTGES  GAGKTENTKK  VIQYLAVVAS
201  SHKGKKDTSI  TQGPSFAYGE  LEKQLLQANP  ILEAFGNAKT  VKNDNSSRFG
251  KFIRINFDVT  GYIVGANIET  YLLEKSRAIR  QARDERTFHI  FYYMIAGAKE
301  KMRSDLLLEG  FNNYTFLSNG  FVPIPAAQDD  EMFQETVEAM  AIMGFSEEEQ
351  LSILKVVSSV  LQLGNIVFKK  ERNTDQASMP  DNTAAQKVCH  LMGINVTDFT
401  RSILTPRIKV  GRDVVQKAQT  KEQADFAVEA  LAKATYERLF  RWILTRVNKA
451  LDKTHRQGAS  FLGILDIAGF  EIFEVNSFEQ  LCINYTNEKL  QQLFNHTMFI
501  LEQEEYQREG  IEWNFIDFGL  DLQPCIELIE  RPNNPPGVLA  LLDEECWFPK
551  ATDKSFVEKL  CTEQGSHPKF  QKPKQLKDKT  EFSIIHYAGK  VDYNASAWLT
601  KNMDPLNDNV  TSLLNASSDK  FVADLWKDVD  RIVGLDQMAK  MTESSLPSAS
651  KTKKGMFRTV  GQLYKEQLGK  LMTTLRNTTP  NFVRCIIPNH  EKRSGKLDA
```

FIG. 6

```
   1 ATGGCGCAGA AGGGCCAACT CAGTGACGAT GAGAAGTTCC TCTTTGTGGA
  51 CAAAAACTTC ATCAACAGCC CAGTGGCCCA GGCTGACTGG GCCGCCAAGA
 101 GACTCGTCTG GGTCCCCTCG GAGAAGCAGG GCTTCGAGGC AGCCAGCATT
 151 AAGGAGGAGA AGGGGGATGA GGTGGTTGTG GAGCTGGTGG AGAATGGCAA
 201 GAAGGTCACG GTTGGGAAAG ATGACATCCA GAAGATGAAC CCACCCAAGT
 251 TCTCCAAGGT GGAGGACATG GCGGAGCTGA CGTGCCTCAA CGAAGCCTCC
 301 GTGCTACACA ACCTGAGGGA GCGGTACTTC TCAGGGCTAA TATATACGTA
 351 CTCTGGCCTC TTCTGCGTGG TGGTCAACCC CTATAAACAC CTGCCCATCT
 401 ACTCGGAGAA GATCGTCGAC ATGTACAAGG GCAAGAAGAG GCACGAGATG
 451 CCGCCTCACA TCTACGCCAT CGCAGACACG GCCTACCGGA GCATGCTTCA
 501 AGATCGGGAG GACCAGTCCA TTCTATGCAC AGGCGAGTCT GGAGCCGGGA
 551 AAACCGAAAA CACCAAGAAG GTCATTCAGT ACCTGGCCGT GGTGGCCTCC
 601 TCCCACAAGG GCAAGAAAGA CACAAGTATC ACGCAAGGCC CATCTTTTGC
 651 CTACGGAGAG CTGGAAAAGC AGCTTCTACA AGCAAACCCG ATTCTGGAGG
 701 CTTTCGGCAA CGCCAAAACA GTGAAGAACG ACAACTCCTC ACGATTCGGC
 751 AAATTCATCC GCATCAACTT CGACGTCACG GGTTACATCG TGGGAGCCAA
 801 CATTGAGACC TATCTGCTAG AAAAATCACG GGCAATTCGC CAAGCCAGAG
 851 ACGAGAGGAC ATTCCACATC TTTTACTACA TGATTGCTGG AGCCAAGGAG
 901 AAGATGAGAA GTGACTTGCT TTTGGAGGGC TTCAACAACT ACACCTTCCT
 951 CTCCAATGGC TTTGTGCCCA TCCCAGCAGC CCAGGATGAT GAGATGTTCC
1001 AGGAAACCGT GGAGGCCATG GCAATCATGG GTTTCAGCGA GGAGGAGCAG
1051 CTATCCATAT TGAAGGTGGT ATCATCGGTC CTGCAGCTTG GAAATATCGT
1101 CTTCAAGAAG GAAAGAAACA CAGACCAGGC GTCCATGCCA GATAACACAG
1151 CTGCTCAGAA AGTTTGCCAC CTCATGGGAA TTAATGTGAC AGATTTCACC
1201 AGATCCATCC TCACTCCTCG TATCAAGGTT GGGCGAGATG TGGTACAGAA
1251 AGCTCAGACA AAAGAACAGG CTGACTTTGC TGTAGAGGCT TTGGCCAAGG
1301 CAACATATGA GCGCCTTTTC CGCTGGATAC TCACCCGCGT GAACAAAGCC
1351 CTGGACAAGA CCCATCGGCA AGGGGCTTCC TTCCTGGGGA TCCTGGATAT
1401 AGCTGGATTT GAGATCTTTG AGGTGAACTC CTTCGAGCAG CTGTGCATCA
1451 ACTACACCAA CGAGAAGCTG CAGCAGCTCT TCAACCACAC CATGTTCATC
1501 CTGGAGCAGG AGGAGTACCA GCGCGAGGGC ATCGAGTGGA ACTTCATCGA
```

FIG. 7A

```
1551  CTTTGGGCTG GACCTACAGC CCTGCATCGA GCTCATCGAG CGACCGAACA

1601  ACCCTCCAGG TGTGCTGGCC CTGCTGGACG AGGAATGCTG GTTCCCCAAA

1651  GCCACGGACA AGTCTTTCGT GGAGAAGCTG TGCACGGAGC AGGGCAGCCA

1701  CCCCAAGTTC CAGAAGCCCA AGCAGCTCAA GGACAAGACT GAGTTCTCCA

1751  TCATCCATTA TGCTGGGAAG GTGGACTATA ATGCGAGTGC CTGGCTGACC

1801  AAGAATATGG ACCCGCTGAA TGACAACGTG ACTTCCCTGC TCAATGCCTC

1851  CTCCGACAAG TTTGTGGCCG ACCTGTGGAA GGACGTGGAC CGCATCGTGG

1901  GCCTGGACCA GATGGCCAAG ATGACGGAGA GCTCGCTGCC CAGCGCCTCC

1951  AAGACCAAGA AGGGCATGTT CCGCACAGTG GGGCAGCTGT ACAAGGAGCA

2001  GCTGGGCAAG CTGATGACCA CGCTACGCAA CACCACGCCC AACTTCGTGC

2051  GCTGCATCAT CCCCAACCAC GAGAAGAGGT CCGGCAAGCT GGATGCGTTC

2101  CTGGTGCTGG AGCAGCTGCG GTGCAATGGG GTGCTGGAAG CATTCGCAT

2151  CTGCCGGCAG GGCTTCCCCA ACCGGATCGT CTTCCAGGAG TTCGCCAAC

2201  GCTACGAGAT CCTGGCGGCG AATGCCATCC CCAAAGGCTT CATGGACGGG

2251  AAGCAGGCCT GCATTCTCAT GATCAAAGCC CTGGAACTTG ACCCCAACTT

2301  ATACAGGATA GGGCAG
```

FIG. 7B

```
  1  MAQKGQLSDD EKFLFVDKNF INSPVAQADW AAKRLVWVPS EKQGFEAASI
 51  KEEKGDEVVV ELVENGKKVT VGKDDIQKMN PPKFSKVEDM AELTCLNEAS
101  VLHNLRERYF SGLIYTYSGL FCVVVNPYKH LPIYSEKIVD MYKGKKRHEM
151  PPHIYAIADT AYRSMLQDRE DQSILCTGES GAGKTENTKK VIQYLAVVAS
201  SHKGKKDTSI TQGPSFAYGE LEKQLLQANP ILEAFGNAKT VKNDNSSRFG
251  KFIRINFDVT GYIVGANIET YLLEKSRAIR QARDERTFHI FYYMIAGAKE
301  KMRSDLLLEG FNNYTFLSNG FVPIPAAQDD EMFQETVEAM AIMGFSEEEQ
351  LSILKVVSSV LQLGNIVFKK ERNTDQASMP DNTAAQKVCH LMGINVTDFT
401  RSILTPRIKV GRDVVQKAQT KEQADFAVEA LAKATYERLF RWILTRVNKA
451  LDKTHRQGAS FLGILDIAGF EIFEVNSFEQ LCINYTNEKL QQLFNHTMFI
501  LEQEEYQREG IEWNFIDFGL DLQPCIELIE RPNNPPGVLA LLDEECWFPK
551  ATDKSFVEKL CTEQGSHPKF QKPKQLKDKT EFSIIHYAGK VDYNASAWLT
601  KNMDPLNDNV TSLLNASSDK FVADLWKDVD RIVGLDQMAK MTESSLPSAS
651  KTKKGMFRTV GQLYKEQLGK LMTTLRNTTP NFVRCIIPNH EKRSGKLDAF
701  LVLEQLRCNG VLEGIRICRQ GFPNRIVFQE FRQRYEILAA NAIPKGFMDG
751  KQACILMIKA LELDPNLYRI GQ
```

FIG. 8

```
   1  ATGGCGCAGA AGGGCCAACT CAGTGACGAT GAGAAGTTCC TCTTTGTGGA
  51  CAAAAACTTC ATCAACAGCC CAGTGGCCCA GGCTGACTGG GCCGCCAAGA
 101  GACTCGTCTG GGTCCCCTCG AGAAGCAGG GCTTCGAGGC AGCCAGCATT
 151  AAGGAGGAGA AGGGGGATGA GGTGGTTGTG GAGCTGGTGG AGAATGGCAA
 201  GAAGGTCACG GTTGGGAAAG ATGACATCCA AAGATGAAC CCACCCAAGT
 251  TCTCCAAGGT GGAGGACATG GCGGAGCTGA CGTGCCTCAA CGAAGCCTCC
 301  GTGCTACACA ACCTGAGGGA GCGGTACTTC TCAGGGCTAA TATATACGTA
 351  CTCTGGCCTC TTCTGCGTGG TGGTCAACCC CTATAAACAC CTGCCCATCT
 401  ACTCGGAGAA GATCGTCGAC ATGTACAAGG GCAAGAAGAG GCACGAGATG
 451  CCGCCTCACA TCTACGCCAT CGCAGACACG GCCTACCGGA GCATGCTTCA
 501  AGATCGGGAG GACCAGTCCA TTCTATGCAC AGGCGAGTCT GGAGCCGGGA
 551  AAACCGAAAA CACCAAGAAG GTCATTCAGT ACCTGGCCGT GGTGGCCTCC
 601  TCCCACAAGG GCAAGAAAGA CACAAGTATC ACGCAAGGCC CATCTTTTGC
 651  CTACGGAGAG CTGGAAAAGC AGCTTCTACA AGCAAACCCG ATTCTGGAGG
 701  CTTTCGGCAA CGCCAAAACA GTGAAGAACG ACAACTCCTC ACGATTCGGC
 751  AAATTCATCC GCATCAACTT CGACGTCACG GGTTACATCG TGGGAGCCAA
 801  CATTGAGACC TATCTGCTAG AAAAATCACG GGCAATTCGC CAAGCCAGAG
 851  ACGAGAGGAC ATTCCACATC TTTTACTACA TGATTGCTGG AGCCAAGGAG
 901  AAGATGAGAA GTGACTTGCT TTTGGAGGGC TTCAACAACT ACACCTTCCT
 951  CTCCAATGGC TTTGTGCCCA TCCCAGCAGC CCAGGATGAT GAGATGTTCC
1001  AGGAAACCGT GGAGGCCATG GCAATCATGG GTTTCAGCGA GGAGGAGCAG
1051  CTATCCATAT TGAAGGTGGT ATCATCGGTC CTGCAGCTTG GAAATATCGT
1101  CTTCAAGAAG GAAAGAAACA CAGACCAGGC GTCCATGCCA GATAACACAG
1151  CTGCTCAGAA AGTTTGCCAC CTCATGGGAA TTAATGTGAC AGATTTCACC
1201  AGATCCATCC TCACTCCTCG TATCAAGGTT GGGCGAGATG TGGTACAGAA
1251  AGCTCAGACA AAAGAACAGG CTGACTTTGC TGTAGAGGCT TTGGCCAAGG
1301  CAACATATGA GCGCCTTTTC CGCTGGATAC TCACCCGCGT GAACAAAGCC
1351  CTGGACAAGA CCCATCGGCA AGGGGCTTCC TTCCTGGGGA TCCTGGATAT
1401  AGCTGGATTT GAGATCTTTG AGGTGAACTC CTTCGAGCAG CTGTGCATCA
1451  ACTACACCAA CGAGAAGCTG CAGCAGCTCT TCAACCACAC CATGTTCATC
1501  CTGGAGCAGG AGGAGTACCA GCGCGAGGGC ATCGAGTGGA ACTTCATCGA
```

FIG. 9A

```
1551  CTTTGGGCTG GACCTACAGC CCTGCATCGA GCTCATCGAG CGACCGAACA

1601  ACCCTCCAGG TGTGCTGGCC CTGCTGGACG AGGAATGCTG GTTCCCCAAA

1651  GCCACGGACA AGTCTTTCGT GGAGAAGCTG TGCACGGAGC AGGGCAGCCA

1701  CCCCAAGTTC CAGAAGCCCA AGCAGCTCAA GGACAAGACT GAGTTCTCCA

1751  TCATCCATTA TGCTGGGAAG GTGGACTATA ATGCGAGTGC CTGGCTGACC

1801  AAGAATATGG ACCCGCTGAA TGACAACGTG ACTTCCCTGC TCAATGCCTC

1851  CTCCGACAAG TTTGTGGCCG ACCTGTGGAA GGACGTGGAC CGCATCGTGG

1901  GCCTGGACCA GATGGCCAAG ATGACGGAGA GCTCGCTGCC CAGCGCCTCC

1951  AAGACCAAGA AGGGCATGTT CCGCACAGTG GGCAGCTGT ACAAGGAGCA

2001  GCTGGGCAAG CTGATGACCA CGCTACGCAA CACCACGCCC AACTTCGTGC

2051  GCTGCATCAT CCCCAACCAC GAGAAGAGGT CCGGCAAGCT GGATGCGTTC

2101  CTGGTGCTGG AGCAGCTGCG GTGCAATGGG GTGCTGGAAG CATTCGCAT

2151  CTGCCGGCAG GGCTTCCCCA ACCGGATCGT CTTCCAGGAG TTCCGCCAAC

2201  GCTACGAGAT CCTGGCGGCG AATGCCATCC CCAAAGGCTT CATGGACGGG

2251  AAGCAGGCCT GCATTCTCAT GATCAAAGCC CTGGAACTTG ACCCCAACTT

2301  ATACAGGATA GGGCAGAGCA AAATCTTCTT CCGAACTGGC GTCCTGGCCC

2351  ACCTAGAGGA GGAGCGAGAT TTGAAGATCA CCGATGTCAT CATGGCCTTC

2401  CAGGCGATGT GTCGTGGCTA CTTGGCCAGA AAGGCTTTTG CCAAGAGGCA

2451  GCAGCAGCTG ACCGCCATGA AGGTGATTCA GAGGAACTGC GCCGCCTACC

2501  TCAAGCTGCG GAACTGGCAG TGGTGGAGGC TTTTCACCAA AGTGAAG
```

FIG. 9B

```
  1  MAQKGQLSDD EKFLFVDKNF INSPVAQADW AAKRLVWVPS EKQGFEAASI
 51  KEEKGDEVVV ELVENGKKVT VGKDDIQKMN PPKFSKVEDM AELTCLNEAS
101  VLHNLRERYF SGLIYTYSGL FCVVVNPYKH LPIYSEKIVD MYKGKKRHEM
151  PPHIYAIADT AYRSMLQDRE DQSILCTGES GAGKTENTKK VIQYLAVVAS
201  SHKGKKDTSI TQGPSFAYGE LEKQLLQANP ILEAFGNAKT VKNDNSSRFG
251  KFIRINFDVT GYIVGANIET YLLEKSRAIR QARDERTFHI FYYMIAGAKE
301  KMRSDLLLEG FNNYTFLSNG FVPIPAAQDD EMFQETVEAM AIMGFSEEEQ
351  LSILKVVSSV LQLGNIVFKK ERNTDQASMP DNTAAQKVCH LMGINVTDFT
401  RSILTPRIKV GRDVVQKAQT KEQADFAVEA LAKATYERLF RWILTRVNKA
451  LDKTHRQGAS FLGILDIAGF EIFEVNSFEQ LCINYTNEKL QQLFNHTMFI
501  LEQEEYQREG IEWNFIDFGL DLQPCIELIE RPNNPPGVLA LLDEECWFPK
551  ATDKSFVEKL CTEQGSHPKF QKPKQLKDKT EFSIIHYAGK VDYNASAWLT
601  KNMDPLNDNV TSLLNASSDK FVADLWKDVD RIVGLDQMAK MTESSLPSAS
651  KTKKGMFRTV GQLYKEQLGK LMTTLRNTTP NFVRCIIPNH EKRSGKLDAF
701  LVLEQLRCNG VLEGIRICRQ GFPNRIVFQE FRQRYEILAA NAIPKGFMDG
751  KQACILMIKA LELDPNLYRI GQSKIFFRTG VLAHLEEERD LKITDVIMAF
801  QAMCRGYLAR KAFAKRQQQL TAMKVIQRNC AAYLKLRNWQ WWRLFTKVK
```

FIG. 10

```
   1  ATGGCGCAGA AGGGCCAACT CAGTGACGAT GAGAAGTTCC TCTTTGTGGA
  51  CAAAAACTTC ATCAACAGCC CAGTGGCCCA GGCTGACTGG GCCGCCAAGA
 101  GACTCGTCTG GGTCCCCTCG GAGAAGCAGG GCTTCGAGGC AGCCAGCATT
 151  AAGGAGGAGA AGGGGGATGA GGTGGTTGTG GAGCTGGTGG AGAATGGCAA
 201  GAAGGTCACG GTTGGGAAAG ATGACATCCA GAAGATGAAC CCACCCAAGT
 251  TCTCCAAGGT GGAGGACATG GCGGAGCTGA CGTGCCTCAA CGAAGCCTCC
 301  GTGCTACACA ACCTGAGGGA GCGGTACTTC TCAGGGCTAA TATATACGTA
 351  CTCTGGCCTC TTCTGCGTGG TGGTCAACCC CTATAAACAC CTGCCCATCT
 401  ACTCGGAGAA GATCGTCGAC ATGTACAAGG GCAAGAAGAG GCACGAGATG
 451  CCGCCTCACA TCTACGCCAT CGCAGACACG GCCTACCGGA GCATGCTTCA
 501  AGATCGGGAG GACCAGTCCA TTCTATGCAC AGGCGAGTCT GGAGCCGGGA
 551  AAACCGAAAA CACCAAGAAG GTCATTCAGT ACCTGGCCGT GGTGGCCTCC
 601  TCCCACAAGG GCAAGAAAGA CACAAGTATC ACGCAAGGCC ATCTTTTGC
 651  CTACGGAGAG CTGGAAAAGC AGCTTCTACA AGCAAACCCG ATTCTGGAGG
 701  CTTTCGGCAA CGCCAAAACA GTGAAGAACG ACAACTCCTC ACGATTCGGC
 751  AAATTCATCC GCATCAACTT CGACGTCACG GGTTACATCG TGGGAGCCAA
 801  CATTGAGACC TATCTGCTAG AAAAATCACG GGCAATTCGC CAAGCCAGAG
 851  ACGAGAGGAC ATTCCACATC TTTTACTACA TGATTGCTGG AGCCAAGGAG
 901  AAGATGAGAA GTGACTTGCT TTTGGAGGGC TTCAACAACT ACACCTTCCT
 951  CTCCAATGGC TTTGTGCCCA TCCCAGCAGC CCAGGATGAT GAGATGTTCC
1001  AGGAAACCGT GGAGGCCATG GCAATCATGG GTTTCAGCGA GGAGGAGCAG
1051  CTATCCATAT TGAAGGTGGT ATCATCGGTC CTGCAGCTTG GAAATATCGT
1101  CTTCAAGAAG GAAAGAAACA CAGACCAGGC GTCCATGCCA GATAACACAG
1151  CTGCTCAGAA AGTTTGCCAC CTCATGGGAA TTAATGTGAC AGATTTCACC
1201  AGATCCATCC TCACTCCTCG TATCAAGGTT GGGCGAGATG TGGTACAGAA
1251  AGCTCAGACA AAAGAACAGG CTGACTTTGC TGTAGAGGCT TTGGCCAAGG
1301  CAACATATGA GCGCCTTTTC CGCTGGATAC TCACCCGCGT GAACAAAGCC
1351  CTGGACAAGA CCCATCGGCA AGGGGCTTCC TTCCTGGGGA TCCTGGATAT
1401  AGCTGGATTT GAGATCTTTG AGGTGAACTC CTTCGAGCAG CTGTGCATCA
1451  ACTACACCAA CGAGAAGCTG CAGCAGCTCT TCAACCACAC CATGTTCATC
1501  CTGGAGCAGG AGGAGTACCA GCGCGAGGGC ATCGAGTGGA ACTTCATCGA
```

FIG. 11A

```
1551  CTTTGGGCTG GACCTACAGC CCTGCATCGA GCTCATCGAG CGACCGAACA
1601  ACCCTCCAGG TGTGCTGGCC CTGCTGGACG AGGAATGCTG GTTCCCCAAA
1651  GCCACGGACA AGTCTTTCGT GGAGAAGCTG TGCACGGAGC AGGGCAGCCA
1701  CCCCAAGTTC CAGAAGCCCA AGCAGCTCAA GGACAAGACT GAGTTCTCCA
1751  TCATCCATTA TGCTGGGAAG GTGGACTATA ATGCGAGTGC CTGGCTGACC
1801  AAGAATATGG ACCCGCTGAA TGACAACGTG ACTTCCCTGC TCAATGCCTC
1851  CTCCGACAAG TTTGTGGCCG ACCTGTGGAA GGACGTGGAC CGCATCGTGG
1901  GCCTGGACCA GATGGCCAAG ATGACGGAGA GCTCGCTGCC CAGCGCCTCC
1951  AAGACCAAGA AGGGCATGTT CCGCACAGTG GGGCAGCTGT ACAAGGAGCA
2001  GCTGGGCAAG CTGATGACCA CGCTACGCAA CACCACGCCC AACTTCGTGC
2051  GCTGCATCAT CCCCAACCAC GAGAAGAGGT CCGGCAAGCT GGATGCGTTC
2101  CTGGTGCTGG AGCAGCTGCG GTGCAATGGG GTGCTGGAAG GCATTCGCAT
2151  CTGCCGGCAG GGCTTCCCCA ACCGGATCGT CTTCCAGGAG TTCCGCCAAC
2201  GCTACGAGAT CCTGGCGGCG AATGCCATCC CCAAAGGCTT CATGGACGGG
2251  AAGCAGGCCT GCATTCTCAT GATCAAAGCC CTGGAACTTG ACCCCAACTT
2301  ATACAGGATA GGGCAGAGCA AAATCTTCTT CCGAACTGGC GTCCTGGCCC
2351  ACCTAGAGGA GGAGCGAGAT TTGAAGATCA CCGATGTCAT CATGGCCTTC
2401  CAGGCGATGT GTCGTGGCTA CTTGGCCAGA AAGGCTTTTG CCAAGAGGCA
2451  GCAGCAGCTG ACCGCCATGA AGGTGATTCA GAGGAACTGC GCCGCCTACC
2501  TCAAGCTGCG GAACTGGCAG TGGTGGAGGC TTTTCACCAA AGTGAAGCCA
2551  CTGCTG
```

FIG. 11B

```
  1  MAQKGQLSDD EKFLFVDKNF INSPVAQADW AAKRLVWVPS EKQGFEAASI
 51  KEEKGDEVVV ELVENGKKVT VGKDDIQKMN PPKFSKVEDM AELTCLNEAS
101  VLHNLRERYF SGLIYTYSGL FCVVVNPYKH LPIYSEKIVD MYKGKKRHEM
151  PPHIYAIADT AYRSMLQDRE DQSILCTGES GAGKTENTKK VIQYLAVVAS
201  SHKGKKDTSI TQGPSFAYGE LEKQLLQANP ILEAFGNAKT VKNDNSSRFG
251  KFIRINFDVT GYIVGANIET YLLEKSRAIR QARDERTFHI FYYMIAGAKE
301  KMRSDLLLEG FNNYTFLSNG FVPIPAAQDD EMFQETVEAM AIMGFSEEEQ
351  LSILKVVSSV LQLGNIVFKK ERNTDQASMP DNTAAQKVCH LMGINVTDFT
401  RSILTPRIKV GRDVVQKAQT KEQADFAVEA LAKATYERLF RWILTRVNKA
451  LDKTHRQGAS FLGILDIAGF EIFEVNSFEQ LCINYTNEKL QQLFNHTMFI
501  LEQEEYQREG IEWNFIDFGL DLQPCIELIE RPNNPPGVLA LLDEECWFPK
551  ATDKSFVEKL CTEQGSHPKF QKPKQLKDKT EFSIIHYAGK VDYNASAWLT
601  KNMDPLNDNV TSLLNASSDK FVADLWKDVD RIVGLDQMAK MTESSLPSAS
651  KTKKGMFRTV GQLYKEQLGK LMTTLRNTTP NFVRCIIPNH EKRSGKLDAF
701  LVLEQLRCNG VLEGIRICRQ GFPNRIVFQE FRQRYEILAA NAIPKGFMDG
751  KQACILMIKA LELDPNLYRI GQSKIFFRTG VLAHLEEERD LKITDVIMAF
801  QAMCRGYLAR KAFAKRQQQL TAMKVIQRNC AAYLKLRNWQ WWRLFTKVKP
851  LL
```

FIG. 12

```
   1  ATGGCGCAGA AGGGCCAACT CAGTGACGAT GAGAAGTTCC TCTTTGTGGA
  51  CAAAAACTTC ATCAACAGCC CAGTGGCCCA GGCTGACTGG GCCGCCAAGA
 101  GACTCGTCTG GGTCCCCTCG GAGAAGCAGG GCTTCGAGGC AGCCAGCATT
 151  AAGGAGGAGA AGGGGGATGA GGTGGTTGTG GAGCTGGTGG AGAATGGCAA
 201  GAAGGTCACG GTTGGGAAAG ATGACATCCA GAAGATGAAC CCACCCAAGT
 251  TCTCCAAGGT GGAGGACATG GCGGAGCTGA CGTGCCTCAA CGAAGCCTCC
 301  GTGCTACACA ACCTGAGGGA GCGGTACTTC TCAGGGCTAA TATATACGTA
 351  CTCTGGCCTC TTCTGCGTGG TGGTCAACCC CTATAAACAC CTGCCCATCT
 401  ACTCGGAGAA GATCGTCGAC ATGTACAAGG GCAAGAAGAG GCACGAGATG
 451  CCGCCTCACA TCTACGCCAT CGCAGACACG GCCTACCGGA GCATGCTTCA
 501  AGATCGGGAG GACCAGTCCA TTCTATGCAC AGGCGAGTCT GGAGCCGGGA
 551  AAACCGAAAA CACCAAGAAG GTCATTCAGT ACCTGGCCGT GGTGGCCTCC
 601  TCCCACAAGG GCAAGAAAGA CACAAGTATC ACGGGAGAGC TGGAAAAGCA
 651  GCTTCTACAA GCAAACCCGA TTCTGGAGGC TTTCGGCAAC GCCAAAACAG
 701  TGAAGAACGA CAACTCCTCA CGATTCGGCA AATTCATCCG CATCAACTTC
 751  GACGTCACGG GTTACATCGT GGGAGCCAAC ATTGAGACCT ATCTGCTAGA
 801  AAAATCACGG GCAATTCGCC AAGCCAGAGA CGAGAGGACA TTCCACATCT
 851  TTTACTACAT GATTGCTGGA GCCAAGGAGA GATGAGAAG TGACTTGCTT
 901  TTGGAGGGCT TCAACAACTA CACCTTCCTC TCCAATGGCT TTGTGCCCAT
 951  CCCAGCAGCC CAGGATGATG AGATGTTCCA GGAAACCGTG GAGGCCATGG
1001  CAATCATGGG TTTCAGCGAG GAGGAGCAGC TATCCATATT GAAGGTGGTA
1051  TCATCGGTCC TGCAGCTTGG AAATATCGTC TTCAAGAAGG AAAGAAACAC
1101  AGACCAGGCG TCCATGCCAG ATAACACAGC TGCTCAGAAA GTTTGCCACC
1151  TCATGGGAAT TAATGTGACA GATTTCACCA GATCCATCCT CACTCCTCGT
1201  ATCAAGGTTG GGCGAGATGT GGTACAGAAA GCTCAGACAA AGAACAGGC
1251  TGACTTTGCT GTAGAGGCTT TGGCCAAGGC AACATATGAG CGCCTTTTCC
1301  GCTGGATACT CACCCGCGTG AACAAAGCCC TGGACAAGAC CCATCGGCAA
1351  GGGGCTTCCT TCCTGGGGAT CCTGGATATA GCTGGATTTG AGATCTTTGA
1401  GGTGAACTCC TTCGAGCAGC TGTGCATCAA CTACACCAAC GAGAAGCTGC
1451  AGCAGCTCTT CAACCACACC ATGTTCATCC TGGAGCAGGA GGAGTACCAG
1501  CGCGAGGGCA TCGAGTGGAA CTTCATCGAC TTTGGGCTGG ACCTACAGCC
```

FIG. 13A

```
1551  CTGCATCGAG CTCATCGAGC GACCGAACAA CCCTCCAGGT GTGCTGGCCC
1601  TGCTGGACGA GGAATGCTGG TTCCCCAAAG CCACGGACAA GTCTTTCGTG
1651  GAGAAGCTGT GCACGGAGCA GGGCAGCCAC CCCAAGTTCC AGAAGCCCAA
1701  GCAGCTCAAG GACAAGACTG AGTTCTCCAT CATCCATTAT GCTGGGAAGG
1751  TGGACTATAA TGCGAGTGCC TGGCTGACCA AGAATATGGA CCCGCTGAAT
1801  GACAACGTGA CTTCCCTGCT CAATGCCTCC TCCGACAAGT TTGTGGCCGA
1851  CCTGTGGAAG GACGTGGACC GCATCGTGGG CCTGGACCAG ATGGCCAAGA
1901  TGACGGAGAG CTCGCTGCCC AGCGCCTCCA AGACCAAGAA GGGCATGTTC
1951  CGCACAGTGG GGCAGCTGTA CAAGGAGCAG CTGGGCAAGC TGATGACCAC
2001  GCTACGCAAC ACCACGCCCA ACTTCGTGCG CTGCATCATC CCCAACCACG
2051  AGAAGAGGTC CGGCAAGCTG GATGCGTTCC TGGTGCTGGA GCAGCTGCGG
2101  TGCAATGGGG TGCTGGAAGG CATTCGCATC TGCCGGCAGG GCTTCCCCAA
2151  CCGGATCGTC TTCCAGGAGT TCCGCCAACG CTACGAGATC CTGGCGGCGA
2201  ATGCCATCCC CAAAGGCTTC ATGGACGGGA AGCAGGCCTG CATTCTCATG
2251  ATCAAAGCCC TGGAACTTGA CCCCAACTTA TACAGGATAG GGCAGAGCAA
2301  AATCTTCTTC CGAACTGGCG TCCTGGCCCA CCTAGAGGAG GAGCGAGATT
2351  TGAAGATCAC CGATGTCATC ATGGCCTTCC AGGCGATGTG TCGTGGCTAC
2401  TTGGCCAGAA AGGCTTTTGC CAAGAGGCAG CAGCAGCTGA CCGCCATGAA
2451  GGTGATTCAG AGGAACTGCG CCGCCTACCT CAAGCTGCGG AACTGGCAGT
2501  GGTGGAGGCT TTTCACCAAA GTGAAGCCAC TGCTG
```

FIG. 13B

```
  1  MAQKGQLSDD EKFLFVDKNF INSPVAQADW AAKRLVWVPS EKQGFEAASI
 51  KEEKGDEVVV ELVENGKKVT VGKDDIQKMN PPKFSKVEDM AELTCLNEAS
101  VLHNLRERYF SGLIYTYSGL FCVVVNPYKH LPIYSEKIVD MYKGKKRHEM
151  PPHIYAIADT AYRSMLQDRE DQSILCTGES GAGKTENTKK VIQYLAVVAS
201  SHKGKKDTSI TQGPSFAYGE LEKQLLQANP ILEAFGNAKT VKNDNSSRFG
251  KFIRINFDVT GYIVGANIET YLLEKSRAIR QARDERTFHI FYYMIAGAKE
301  KMRSDLLLEG FNNYTFLSNG FVPIPAAQDD EMFQETVEAM AIMGFSEEEQ
351  LSILKVVSSV LQLGNIVFKK ERNTDQASMP DNTAAQKVCH LMGINVTDFT
401  RSILTPRIKV GRDVVQKAQT KEQADFAVEA LAKATYERLF RWILTRVNKA
451  LDKTHRQGAS FLGILDIAGF EIFEVNSFEQ LCINYTNEKL QQLFNHTMFI
501  LEQEEYQREG IEWNFIDFGL DLQPCIELIE RPNNPPGVLA LLDEECWFPK
551  ATDKSFVEKL CTEQGSHPKF QKPKQLKDKT EFSIIHYAGK VDYNASAWLT
601  KNMDPLNDNV TSLLNASSDK FVADLWKDVD RIVGLDQMAK MTESSLPSAS
651  KTKKGMFRTV GQLYKEQLGK LMTTLRNTTP NFVRCIIPNH EKRSGKLDAF
701  LVLEQLRCNG VLEGIRICRQ GFPNRIVFQE FRQRYEILAA NAIPKGFMDG
751  KQACILMIKA LELDPNLYRI GQSKIFFRTG VLAHLEEERD LKITDVIMAF
801  QAMCRGYLAR KAFAKRQQQL TAMKVIQRNC AAYLKLRNWQ WWRLF
```

FIG. 14

SEQUENCE LISTING

<160> NUMBER OF SEQ ID NOS: 17

<210> SEQ ID NO 1
<211> LENGTH: 5835
<212> TYPE: DNA
<213> ORGANISM: Homo sapiens

<400> SEQUENCE: 1

```
atggcgcaga agggccaact cagtgacgat gagaagttcc tctttgtgga caaaaacttc      60
atcaacagcc cagtggccca ggctgactgg gccgccaaga gactcgtctg ggtcccctcg     120
gagaagcagg gcttcgaggc agccagcatt aaggaggaga aggggggatga ggtggttgtg     180 gagctggtgg agaatggcaa gaaggtcacg gttgggaaag atgacatcca gaagatgaac     240
ccacccaagt tctccaaggt ggaggacatg gcggagctga cgtgcctcaa cgaagcctcc     300
```

-continued

```
gtgctacaca acctgaggga gcggtacttc tcagggctaa tatatacgta ctctggcctc      360
ttctgcgtgg tggtcaaccc ctataaacac ctgcccatct actcggagaa gatcgtcgac      420
atgtacaagg gcaagaagag gcacgagatg ccgcctcaca tctacgccat cgcagacacg      480
gcctaccgga gcatgcttca agatcgggag gaccagtcca ttctatgcac aggcgagtct      540
ggagccggga aaaccgaaaa caccaagaag gtcattcagt acctggccgt ggtggcctcc      600
tcccacaagg gcaagaaaga cacaagtatc acgcaaggcc catcttttgc ctacggagag      660
ctggaaaagc agcttctaca agcaaacccg attctggagg ctttcggcaa cgccaaaaca      720
gtgaagaacg acaactcctc acgattcggc aaattcatcc gcatcaactt cgacgtcacg      780
ggttacatcg tgggagccaa cattgagacc tatctgctag aaaaatcacg ggcaattcgc      840
caagccagag acgagaggac attccacatc ttttactaca tgattgctgg agccaaggag      900
aagatgagaa gtgacttgct tttggagggc ttcaacaact acaccttcct ctccaatggc      960
tttgtgccca tcccagcagc ccaggatgat gagatgttcc aggaaaccgt ggaggccatg     1020
gcaatcatgg gtttcagcga ggaggagcag ctatccatat tgaaggtggt atcatcggtc     1080
ctgcagcttg gaaatatcgt cttcaagaag gaaagaaaca cagaccaggc gtccatgcca     1140
gataacacag ctgctcagaa agtttgccac ctcatgggaa ttaatgtgac agatttcacc     1200
agatccatcc tcactcctcg tatcaaggtt gggcgagatg tggtacagaa agctcagaca     1260
aaagaacagg ctgactttgc tgtagaggct ttggccaagg caacatatga gcgccttttc     1320
cgctggatac tcacccgcgt gaacaaagcc ctggacaaga cccatcggca aggggcttcc     1380
ttcctgggga tcctggatat agctggattt gagatctttg aggtgaactc cttcgagcag     1440
ctgtgcatca actacaccaa cgagaagctg cagcagctct tcaaccacac catgttcatc     1500
ctggagcagg aggagtacca gcgcgagggc atcgagtgga acttcatcga ctttgggctg     1560
gacctacagc cctgcatcga gctcatcgag cgaccgaaca ccctccagg tgtgctggcc      1620
ctgctggacg aggaatgctg gttccccaaa gccacggaca agtctttcgt ggagaagctg     1680
tgcacggagc agggcagcca ccccaagttc cagaagccca agcagctcaa ggacaagact     1740
gagttctcca tcatccatta tgctgggaag gtggactata atgcgagtgc ctggctgacc     1800
aagaatatgg acccgctgaa tgacaacgtg acttccctgc tcaatgcctc ctccgacaag     1860
tttgtggccg acctgtggaa ggacgtggac cgcatcgtgg gcctggacca gatggccaag     1920
atgacggaga gctcgctgcc cagcgcctcc aagaccaaga agggcatgtt ccgcacagtg     1980
gggcagctgt acaaggagca gctgggcaag ctgatgacca cgctacgcaa caccacgccc     2040
aacttcgtgc gctgcatcat ccccaaccac gagaagaggt ccggcaagct ggatgcgttc     2100
ctggtgctga gcagctgcg gtgcaatggg gtgctggaag gcattcgcat ctgccggcag     2160
ggcttcccca accggatcgt cttccaggag ttccgccaac gctacgagat cctggcggcg     2220
aatgccatcc ccaaaggctt catggacggg aagcaggcct gcattctcat gatcaaagcc     2280
ctggaacttg accccaactt atacaggata gggcagagca aaatcttctt ccgaactggc     2340
gtcctggccc acctagagga ggagcgagat ttgaagatca ccgatgtcat catggccttc     2400
caggcgatgt gtcgtggcta cttggccaga aaggcttttg ccaagaggca gcagcagctg     2460
accgccatga aggtgattca gaggaactgc gccgcctacc tcaagctgcg gaactggcag     2520
tggtggaggc ttttcaccaa agtgaagcca ctgctgcagg tgacacggca ggaggaggag     2580
atgcaggcca aggaggatga actgcagaag accaaggagc ggcagcagaa ggcagagaat     2640
gagcttaagg agctggaaca gaagcactcg cagctgaccg aggagaagaa cctgctacag     2700
```

```
gaacagctgc aggcagagac agagctgtat gcagaggctg aggagatgcg ggtgcggctg    2760
gcggccaaga agcaggagct ggaggagata ctgcatgaga tggaggcccg cctggaggag    2820
gaggaagaca ggggccagca gctacaggct gaaaggaaga agatggccca gcagatgctg    2880
gaccttgaag aacagctgga ggaggaggaa gctgccaggc agaagctgca acttgagaag    2940
gtcacggctg aggccaagat caagaaactg gaggatgaga tcctggtcat ggatgatcag    3000
aacaataaac tatcaaaaga acgaaaactc cttgaggaga ggattagtga cttaacgaca    3060
aatcttgcag aagaggaaga aaaggccaag aatcttacca agctgaaaaa caagcatgaa    3120
tctatgattt cagaactgga agtgcggcta aagaaggaag agaagagccg acaggagctg    3180
gagaagctga acggaagct ggaggtgat gccagcgact ccacgagca gatcgctgac    3240
```

| | | |
|---|---|---|
| acagccaaag agaatgagaa gaaagccaag agcttggaag cagacctcat gcagctacaa | | 5100 |
| gaggacctcg ccgccgctga gagggctcgc aaacaagcgg acctcgagaa ggaggaactg | | 5160 |
| gcagaggagc tggccagtag cctgtcggga aggaacgcac tccaggacga gaagcgccgc | | 5220 |
| ctggaggccc ggatcgccca gctggaggag gagctggagg aggagcaggg caacatggag | | 5280 |
| gccatgagcg accgggtccg caaagccaca cagcaggccg agcagctcag caacgagctg | | 5340 |
| gccacagagc gcagcacggc ccagaagaat gagagtgccc ggcagcagct cgagcggcag | | 5400 |
| aacaaggagc tccggagcaa gctccacgag atggaggggg ccgtcaagtc caagttcaag | | 5460 |
| tccaccatcg cggcgctgga ggccaagatt gcacagctgg aggagcaggt cgagcaggag | | 5520 |
| gccagagaga acaggcggc caccaagtcg ctgaagcaga agacaagaa gctgaaggaa | | 5580 |
| atcttgctgc aggtggagga cgagcgcaag atggccgagc agtacaagga gcaggcagag | | 5640 |
| aaaggcaatg ccagggtcaa gcagctcaag aggcagctgg aggaggcaga ggaggagtcc | | 5700 |
| cagcgcatca cgccaaccg caggaagctg cagcgggagc tggatgaggc cacggagagc | | 5760 |
| aacgaggcca tgggccgcga ggtgaacgca ctcaagagca agctcagagg gccccccca | | 5820 |
| caggaaactt cgcag | | 5835 |

<210> SEQ ID NO 2
<211> LENGTH: 1945
<212> TYPE: PRT
<213> ORGANISM: Homo sapiens

<400> SEQUENCE: 2

Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
            20                  25                  30

Lys Arg Leu Val Trp Val Pro Ser Glu Lys Gln Gly Phe Glu Ala Ala
        35                  40                  45

Ser Ile Lys Glu Glu Lys Gly Asp Glu Val Val Val Glu Leu Val Glu
    50                  55                  60

Asn Gly Lys Lys Val Thr Val Gly Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Arg Glu Arg Tyr Phe Ser Gly
            100                 105                 110

Leu Ile Tyr Thr Tyr Ser Gly Leu Phe Cys Val Val Val Asn Pro Tyr
        115                 120                 125

Lys His Leu Pro Ile Tyr Ser Glu Lys Ile Val Asp Met Tyr Lys Gly
    130                 135                 140

Lys Lys Arg His Glu Met Pro Pro His Ile Tyr Ala Ile Ala Asp Thr
145                 150                 155                 160

Ala Tyr Arg Ser Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
            180                 185                 190

Gln Tyr Leu Ala Val Val Ala Ser Ser His Lys Gly Lys Lys Asp Thr
        195                 200                 205

Ser Ile Thr Gln Gly Pro Ser Phe Ala Tyr Gly Glu Leu Glu Lys Gln
    210                 215                 220

Leu Leu Gln Ala Asn Pro Ile Leu Glu Ala Phe Gly Asn Ala Lys Thr

-continued

```
            225                 230                 235                 240
    Val Lys Asn Asp Asn Ser Ser Arg Phe Gly Lys Phe Ile Arg Ile Asn
                            245                 250                 255

Phe Asp Val Thr Gly Tyr Ile Val Gly Ala Asn Ile Glu Thr Tyr Leu
                260                 265                 270

Leu Glu Lys Ser Arg Ala Ile Arg Gln Ala Arg Asp Glu Arg Thr Phe
                275                 280                 285

His Ile Phe Tyr Tyr Met Ile Ala Gly Ala Lys Glu Lys Met Arg Ser
                290                 295                 300

Asp Leu Leu Leu Glu Gly Phe Asn Asn Tyr Thr Phe Leu Ser Asn Gly
    305                 310                 315                 320

Phe Val Pro Ile Pro Ala Ala Gln Asp Glu Met Phe Gln Glu Thr
                325                 330                 335

Val Glu Ala Met Ala Ile Met Gly Phe Ser Glu Glu Glu Gln Leu Ser
                340                 345                 350

Ile Leu Lys Val Val Ser Ser Val Leu Gln Leu Gly Asn Ile Val Phe
                355                 360                 365

Lys Lys Glu Arg Asn Thr Asp Gln Ala Ser Met Pro Asp Asn Thr Ala
                370                 375                 380

Ala Gln Lys Val Cys His Leu Met Gly Ile Asn Val Thr Asp Phe Thr
    385                 390                 395                 400

Arg Ser Ile Leu Thr Pro Arg Ile Lys Val Gly Arg Asp Val Val Gln
                    405                 410                 415

Lys Ala Gln Thr Lys Glu Gln Ala Asp Phe Ala Val Glu Ala Leu Ala
                420                 425                 430

Lys Ala Thr Tyr Glu Arg Leu Phe Arg Trp Ile Leu Thr Arg Val Asn
                435                 440                 445

Lys Ala Leu Asp Lys Thr His Arg Gln Gly Ala Ser Phe Leu Gly Ile
                450                 455                 460

Leu Asp Ile Ala Gly Phe Glu Ile Phe Glu Val Asn Ser Phe Glu Gln
    465                 470                 475                 480

Leu Cys Ile Asn Tyr Thr Asn Glu Lys Leu Gln Gln Leu Phe Asn His
                    485                 490                 495

Thr Met Phe Ile Leu Glu Gln Glu Glu Tyr Gln Arg Glu Gly Ile Glu
                500                 505                 510

Trp Asn Phe Ile Asp Phe Gly Leu Asp Leu Gln Pro Cys Ile Glu Leu
                515                 520                 525

Ile Glu Arg Pro Asn Asn Pro Pro Gly Val Leu Ala Leu Leu Asp Glu
                530                 535                 540

Glu Cys Trp Phe Pro Lys Ala Thr Asp Lys Ser Phe Val Glu Lys Leu
    545                 550                 555                 560

Cys Thr Glu Gln Gly Ser His Pro Lys Phe Gln Lys Pro Lys Gln Leu
                    565                 570                 575

Lys Asp Lys Thr Glu Phe Ser Ile Ile His Tyr Ala Gly Lys Val Asp
                580                 585                 590

Tyr Asn Ala Ser Ala Trp Leu Thr Lys Asn Met Asp Pro Leu Asn Asp
                595                 600                 605

Asn Val Thr Ser Leu Leu Asn Ala Ser Ser Asp Lys Phe Val Ala Asp
                610                 615                 620

Leu Trp Lys Asp Val Asp Arg Ile Val Gly Leu Asp Gln Met Ala Lys
    625                 630                 635                 640

Met Thr Glu Ser Ser Leu Pro Ser Ala Ser Lys Thr Lys Lys Gly Met
                    645                 650                 655
```

```
Phe Arg Thr Val Gly Gln Leu Tyr Lys Glu Gln Leu Gly Lys Leu Met
            660                 665                 670

Thr Thr Leu Arg Asn Thr Thr Pro Asn Phe Val Arg Cys Ile Ile Pro
        675                 680                 685

Asn His Glu Lys Arg Ser Gly Lys Leu Asp Ala Phe Leu Val Leu Glu
    690                 695                 700

Gln Leu Arg Cys Asn Gly Val Leu Glu Gly Ile Arg Ile Cys Arg Gln
705                 710                 715                 720

Gly Phe Pro Asn Arg Ile Val Phe Gln Glu Phe Arg Gln Arg Tyr Glu
                725                 730                 735

Ile Leu Ala Ala Asn Ala Ile Pro Lys Gly Phe Met Asp Gly Lys Gln
            740                 745                 750

Ala Cys Ile Leu Met Ile Lys Ala Leu Glu Leu Asp Pro Asn Leu Tyr
        755                 760                 765

Arg Ile Gly Gln Ser Lys Ile Phe Phe Arg Thr Gly Val Leu Ala His
    770                 775                 780

Leu Glu Glu Glu Arg Asp Leu Lys Ile Thr Asp Val Ile Met Ala Phe
785                 790                 795                 800

Gln Ala Met Cys Arg Gly Tyr Leu Ala Arg Lys Ala Phe Ala Lys Arg
                805                 810                 815

Gln Gln Gln Leu Thr Ala Met Lys Val Ile Gln Arg Asn Cys Ala Ala
            820                 825                 830

Tyr Leu Lys Leu Arg Asn Trp Gln Trp Trp Arg Leu Phe Thr Lys Val
        835                 840                 845

Lys Pro Leu Leu Gln Val Thr Arg Gln Glu Glu Met Gln Ala Lys
    850                 855                 860

Glu Asp Glu Leu Gln Lys Thr Lys Glu Arg Gln Gln Lys Ala Glu Asn
865                 870                 875                 880

Glu Leu Lys Glu Leu Glu Gln Lys His Ser Gln Leu Thr Glu Glu Lys
                885                 890                 895

Asn Leu Leu Gln Glu Gln Leu Gln Ala Glu Thr Glu Leu Tyr Ala Glu
            900                 905                 910

Ala Glu Glu Met Arg Val Arg Leu Ala Ala Lys Lys Gln Glu Leu Glu
        915                 920                 925

Glu Ile Leu His Glu Met Glu Ala Arg Leu Glu Glu Glu Asp Arg
    930                 935                 940

Gly Gln Gln Leu Gln Ala Glu Arg Lys Lys Met Ala Gln Gln Met Leu
945                 950                 955                 960

Asp Leu Glu Glu Gln Leu Glu Glu Glu Ala Ala Arg Gln Lys Leu
                965                 970                 975

Gln Leu Glu Lys Val Thr Ala Glu Ala Lys Ile Lys Lys Leu Glu Asp
            980                 985                 990

Glu Ile Leu Val Met Asp Asp Gln Asn Asn Lys Leu Ser Lys Glu Arg
        995                 1000                1005

Lys Leu Leu Glu Glu Arg Ile Ser Asp Leu Thr Thr Asn Leu Ala
    1010                1015                1020

Glu Glu Glu Glu Lys Ala Lys Asn Leu Thr Lys Leu Lys Asn Lys
    1025                1030                1035

His Glu Ser Met Ile Ser Glu Leu Glu Val Arg Leu Lys Lys Glu
    1040                1045                1050

Glu Lys Ser Arg Gln Glu Leu Glu Lys Leu Lys Arg Lys Leu Glu
    1055                1060                1065
```

-continued

```
Gly Asp Ala Ser Asp Phe His Glu Gln Ile Ala Asp Leu Gln Ala
    1070                1075                1080

Gln Ile Ala Glu Leu Lys Met Gln Leu Ala Lys Lys Glu Glu Glu
    1085                1090                1095

Leu Gln Ala Ala Leu Ala Arg Leu Asp Asp Glu Ile Ala Gln Lys
    1100                1105                1110

Asn Asn Ala Leu Lys Lys Ile Arg Glu Leu Glu Gly His Ile Ser
    1115                1120                1125

Asp Leu Gln Glu Asp Leu Asp Ser Glu Arg Ala Ala Arg Asn Lys
    1130                1135                1140

Ala Glu Lys Gln Lys Arg Asp Leu Gly Glu Glu Leu Glu Ala Leu
    1145                1150                1155

Lys Thr Glu Leu Glu Asp Thr Leu Asp Ser Thr Ala Thr Gln Gln
    1160                1165                1170

Glu Leu Arg Ala Lys Arg Glu Gln Glu Val Thr Val Leu Lys Lys
    1175                1180                1185

Ala Leu Asp Glu Glu Thr Arg Ser His Glu Ala Gln Val Gln Glu
    1190                1195                1200

Met Arg Gln Lys His Ala Gln Ala Val Glu Glu Leu Thr Glu Gln
    1205                1210                1215

Leu Glu Gln Phe Lys Arg Ala Lys Ala Asn Leu Asp Lys Asn Lys
    1220                1225                1230

Gln Thr Leu Glu Lys Glu Asn Ala Asp Leu Ala Gly Glu Leu Arg
    1235                1240                1245

Val Leu Gly Gln Ala Lys Gln Glu Val Glu His Lys Lys Lys Lys
    1250                1255                1260

Leu Glu Ala Gln Val Gln Glu Leu Gln Ser Lys Cys Ser Asp Gly
    1265                1270                1275

Glu Arg Ala Arg Ala Glu Leu Asn Asp Lys Val His Lys Leu Gln
    1280                1285                1290

Asn Glu Val Glu Ser Val Thr Gly Met Leu Asn Glu Ala Glu Gly
    1295                1300                1305

Lys Ala Ile Lys Leu Ala Lys Asp Val Ala Ser Leu Ser Ser Gln
    1310                1315                1320

Leu Gln Asp Thr Gln Glu Leu Leu Gln Glu Glu Thr Arg Gln Lys
    1325                1330                1335

Leu Asn Val Ser Thr Lys Leu Arg Gln Leu Glu Glu Glu Arg Asn
    1340                1345                1350

Ser Leu Gln Asp Gln Leu Asp Glu Glu Met Glu Ala Lys Gln Asn
    1355                1360                1365

Leu Glu Arg His Ile Ser Thr Leu Asn Ile Gln Leu Ser Asp Ser
    1370                1375                1380

Lys Lys Lys Leu Gln Asp Phe Ala Ser Thr Val Glu Ala Leu Glu
    1385                1390                1395

Glu Gly Lys Lys Arg Phe Gln Lys Glu Ile Glu Asn Leu Thr Gln
    1400                1405                1410

Gln Tyr Glu Glu Lys Ala Ala Ala Tyr Asp Lys Leu Glu Lys Thr
    1415                1420                1425

Lys Asn Arg Leu Gln Gln Glu Leu Asp Asp Leu Val Val Asp Leu
    1430                1435                1440

Asp Asn Gln Arg Gln Leu Val Ser Asn Leu Glu Lys Lys Gln Arg
    1445                1450                1455

Lys Phe Asp Gln Leu Leu Ala Glu Glu Lys Asn Ile Ser Ser Lys
```

-continued

```
            1460                1465                1470

Tyr Ala Asp Glu Arg Asp Arg Ala Glu Ala Glu Arg Glu Lys
        1475                1480                1485

Glu Thr Lys Ala Leu Ser Leu Ala Arg Ala Leu Glu Glu Ala Leu
        1490                1495                1500

Glu Ala Lys Glu Glu Leu Glu Arg Thr Asn Lys Met Leu Lys Ala
        1505                1510                1515

Glu Met Glu Asp Leu Val Ser Ser Lys Asp Val Gly Lys Asn
        1520                1525                1530

Val His Glu Leu Glu Lys Ser Lys Arg Ala Leu Glu Thr Gln Met
        1535                1540                1545

Glu Glu Met Lys Thr Gln Leu Glu Glu Leu Glu Asp Glu Leu Gln
        1550                1555                1560

Ala Thr Glu Asp Ala Lys Leu Arg Leu Glu Val Asn Met Gln Ala
        1565                1570                1575

Leu Lys Gly Gln Phe Glu Arg Asp Leu Gln Ala Arg Asp Glu Gln
        1580                1585                1590

Asn Glu Glu Lys Arg Arg Gln Leu Gln Arg Gln Leu His Glu Tyr
        1595                1600                1605

Glu Thr Glu Leu Glu Asp Glu Arg Lys Gln Arg Ala Leu Ala Ala
        1610                1615                1620

Ala Ala Lys Lys Lys Leu Glu Gly Asp Leu Lys Asp Leu Glu Leu
        1625                1630                1635

Gln Ala Asp Ser Ala Ile Lys Gly Arg Glu Glu Ala Ile Lys Gln
        1640                1645                1650

Leu Arg Lys Leu Gln Ala Gln Met Lys Asp Phe Gln Arg Glu Leu
        1655                1660                1665

Glu Asp Ala Arg Ala Ser Arg Asp Glu Ile Phe Ala Thr Ala Lys
        1670                1675                1680

Glu Asn Glu Lys Lys Ala Lys Ser Leu Glu Ala Asp Leu Met Gln
        1685                1690                1695

Leu Gln Glu Asp Leu Ala Ala Ala Glu Arg Ala Arg Lys Gln Ala
        1700                1705                1710

Asp Leu Glu Lys Glu Glu Leu Ala Glu Glu Leu Ala Ser Ser Leu
        1715                1720                1725

Ser Gly Arg Asn Ala Leu Gln Asp Glu Lys Arg Arg Leu Glu Ala
        1730                1735                1740

Arg Ile Ala Gln Leu Glu Glu Glu Leu Glu Glu Glu Gln Gly Asn
        1745                1750                1755

Met Glu Ala Met Ser Asp Arg Val Arg Lys Ala Thr Gln Gln Ala
        1760                1765                1770

Glu Gln Leu Ser Asn Glu Leu Ala Thr Glu Arg Ser Thr Ala Gln
        1775                1780                1785

Lys Asn Glu Ser Ala Arg Gln Gln Leu Glu Arg Gln Asn Lys Glu
        1790                1795                1800

Leu Arg Ser Lys Leu His Glu Met Glu Gly Ala Val Lys Ser Lys
        1805                1810                1815

Phe Lys Ser Thr Ile Ala Ala Leu Glu Ala Lys Ile Ala Gln Leu
        1820                1825                1830

Glu Glu Gln Val Glu Gln Glu Ala Arg Glu Lys Gln Ala Ala Thr
        1835                1840                1845

Lys Ser Leu Lys Gln Lys Asp Lys Lys Leu Lys Glu Ile Leu Leu
        1850                1855                1860
```

```
Gln Val Glu Asp Glu Arg Lys Met Ala Glu Gln Tyr Lys Glu Gln
    1865                1870                1875
Ala Glu Lys Gly Asn Ala Arg Val Lys Gln Leu Lys Arg Gln Leu
    1880                1885                1890
Glu Glu Ala Glu Glu Ser Gln Arg Ile Asn Ala Asn Arg Arg
    1895                1900                1905
Lys Leu Gln Arg Glu Leu Asp Glu Ala Thr Glu Ser Asn Glu Ala
    1910                1915                1920
Met Gly Arg Glu Val Asn Ala Leu Lys Ser Lys Leu Arg Gly Pro
    1925                1930                1935
Pro Pro Gln Glu Thr Ser Gln
    1940            1945

<210> SEQ ID NO 3
<211> LENGTH: 5937
<212> TYPE: DNA
<213> ORGANISM: Homo sapiens

<400> SEQUENCE: 3
atggcgcaga agggccaact cagtgacgat gagaagttcc tctttgtgga caaaaacttc      60
atcaacagcc cagtgcccca ggctgactgg ccgccaaga  gactcgtctg gtcccctcg     120 gagaagcagg gcttcgaggc agccagcatt aaggaggaga aggggatga ggtggttgtg     180 gagctggtgg agaatggcaa gaaggtcacg gttgggaaag atgacatcca  gaagatgaac     240
ccacccaagt tctccaaggt ggaggacatg gcggagctga cgtgcctcaa cgaagcctcc     300
gtgctacaca acctgaggga gcggtacttc tcagggctaa tatatacgta ctctggcctc     360
ttctgcgtgt tggtcaaccc ctataaacac ctgcccatct actcggagaa gatcgtcgac     420
atgtacaagg gcaagaagag gcacgagatg ccgcctcaca tctacgccat cgcagacacg     480
gcctaccgga gcatgcttca agatcgggag gaccagtcca ttctatgcac aggcgagtct     540
ggagccggga aaaccgaaaa caccaagaag gtcattcagt acctggccgt ggtggcctcc     600
tcccacaagg gcaagaaaga cacaagtatc acgcaaggcc atcttttgc ctacggagag     660 ctggaaaagc agcttctaca agcaaacccg attctggagg ctttcggcaa cgccaaaaca     720
gtgaagaacg acaactcctc acgattcggc aaattcatcc gcatcaactt cgacgtcacg     780
ggttacatcg tgggagccaa cattgagacc tatctgctag aaaaatcacg ggcaattcgc     840
caagccagag acgagaggac attccacatc ttttactaca tgattgctgg agccaaggag     900
aagatgagaa gtgacttgct tttggagggc ttcaacaact acaccttcct ctccaatggc     960
tttgtgccca tcccagcagc ccaggatgat gagatgttcc aggaaaccgt ggaggccatg    1020
gcaatcatgg gtttcagcga ggaggagcag ctatccatat tgaaggtggt atcatcggtc    1080
ctgcagcttg gaaatatcgt cttcaagaag gaaagaaaca cagaccaggc gtccatgcca    1140
gataacacag ctgctcagaa agtttgccac ctcatgggaa ttaatgtgac agatttcacc    1200
agatccatcc tcactcctcg tatcaaggtt gggcgagatg tggtacagaa agctcagaca    1260
aaagaacagg ctgactttgc tgtagaggct ttggccaagg caacatatga gcgccttttc    1320
cgctggatac tcacccgcgt gaacaaagcc tggacaaga  cccatcggca aggggcttcc    1380
ttcctgggga tcctggatat agctggatt  gagatctttg aggtgaactc cttcgagcag    1440
ctgtgcatca actacaccaa cgagaagctg cagcagctct tcaaccacac catgttcatc    1500
ctggagcagg aggagtacca gcgcgagggc atcgagtgga cttcatcga ctttgggctg    1560
```

```
gacctacagc cctgcatcga gctcatcgag cgaccgaaca accctccagg tgtgctggcc    1620
ctgctggacg aggaatgctg gttccccaaa gccacggaca agtctttcgt ggagaagctg    1680
tgcacggagc agggcagcca ccccaagttc cagaagccca agcagctcaa ggacaagact    1740
gagttctcca tcatccatta tgctgggaag gtggactata atgcgagtgc ctggctgacc    1800
aagaatatgg acccgctgaa tgacaacgtg acttccctgc tcaatgcctc ctccgacaag    1860
tttgtggccg acctgtggaa ggacgtggac cgcatcgtgg gcctggacca gatggccaag    1920
atgacggaga gctcgctgcc cagcgcctcc aagaccaaga agggcatgtt ccgcacagtg    1980
gggcagctgt acaaggagca gctgggcaag ctgatgacca cgctacgcaa caccacgccc    2040
aacttcgtgc gctgcatcat ccccaaccac gagaagaggt ccggcaagct ggatgcgttc    2100
ctggtgctgg agcagctgcg cgtgcaatgg gtgctggaag gcattcgcat ctgccggcag    2160
ggcttcccca accggatcgt cttccaggag ttccgccaac gctacgagat cctggcggcg    2220
aatgccatcc ccaaaggctt catggacggg aagcaggcct gcattctcat gatcaaagcc    2280
ctggaacttg accccaactt atacaggata gggcagagca aaatcttctt ccgaactggc    2340
gtcctggccc acctagagga ggagcgagat ttgaagatca ccgatgtcat catggccttc    2400
caggcgatgt gtcgtggcta cttggccaga aaggcttttg ccaagaggca gcagcagctg    2460
accgccatga aggtgattca gaggaactgc gccgcctacc tcaagctgcg gaactggcag    2520
tggtggaggc ttttcaccaa agtgaagcca ctgctgcagg tgacacggca ggaggaggag    2580
atgcaggcca aggaggatga actgcagaag accaaggagc ggcagcagaa ggcagagaat    2640
gagcttaagg agctggaaca gaagcactcg cagctgaccg aggagaagaa cctgctacag    2700
gaacagctgc aggcagagac agagctgtat gcagaggctg aggagatgcg ggtgcggctg    2760
gcggccaaga gcaggagct ggaggagata ctgcatgaga tggaggcccg cctggaggag    2820
gaggaagaca ggggccagca gctacaggct gaaaggaaga gatggcccca gcagatgctg    2880
gaccttgaag aacagctgga ggaggaggaa gctgccaggc agaagctgca acttgagaag    2940
gtcacggctg aggccaagat caagaaactg gaggatgaga tcctggtcat ggatgatcag    3000
aacaataaac tatcaaaaga acgaaaactc cttgaggaga ggattagtga cttaacgaca    3060
aatcttgcag aagaggaaga aaaggccaag aatcttacca agctgaaaaa caagcatgaa    3120
tctatgattt cagaactgga agtgcggcta agaaggaag agaagagccg acaggagctg    3180
gagaagctga acggaagct ggagggtgat gccagcgact ccacgagca gatcgctgac    3240 ctccaggcgc agatcgcaga gctcaagatg cagctggcca agaaggagga ggagctgcag    3300
gcggccctgg ccaggcttga cgatgaaatc gctcagaaga caatgccct gaagaagatc    3360 cgggagctgg agggccacat ctcagacctc caggaggacc tggactcaga gcgggccgcc    3420
aggaacaagg ctgaaaagca gaagcgagac ctcggcgagg agctggaggc cctaaagaca    3480
gagctggaag acacactgga cagcacagcc actcagcagg agctcagggc caagagggag    3540
caggaggtga cggtgctgaa gaaggccctg gatgaagaga cgcggtccca tgaggctcag    3600
gtccaggaga tgaggcagaa acacgcacag gcggtggagg agctcacaga gcagcttgag    3660
cagttcaaga gggccaaggc gaacctagac aagaataagc agacgctgga gaaagagaac    3720
gcagacctgg ccgggagct gcgggtcctg ggccaggcca agcaggaggt ggaacataag    3780
aagaagaagc tggaggcgca ggtgcaggag ctgcagtcca agtgcagcga tgggagcgg    3840 gcccgggcgg agctcaatga caaagtccac aagctgcaga atgaagttga gagcgtcaca    3900
gggatgctta acgaggccga ggggaaggcc attaagctgg ccaaggacgt ggcgtccctc    3960
```

```
agttcccagc tccaggacac ccaggagctg cttcaagaag aaacccggca gaagctcaac    4020
gtgtctacga agctgcgcca gctggaggag gagcggaaca gcctgcaaga ccagctggac    4080
gaggagatgg aggccaagca gaacctggag cgccacatct ccactctcaa catccagctc    4140
tccgactcga agaagaagct gcaggacttt gccagcaccg tggaagctct ggaagagggg    4200
aagaagaggt tccagaagga gatcgagaac ctcacccagc agtacgagga aaggcggcc    4260 gcttatgata aactggaaaa gaccaagaac aggcttcagc aggagctgga cgacctggtt    4320
gttgatttgg acaaccagcg gcaactcgtg tccaacctgg aaaagaagca gaggaaattt    4380
gatcagttgt tagccgagga gaaaaacatc tcttccaaat acgcggatga gagggacaga    4440
gctgaggcag aagccaggga aaggaaaacc aaggccctgt ccctggctcg ggcccttgaa    4500
gaggccttgg aagccaaaga ggaactcgag cggaccaaca aaatgctcaa agccgaaatg    4560
gaagacctgg tcagctccaa ggatgacgtg gcaagaacg tccatgagct ggagaagtcc    4620
aagcgggccc tggagaccca gatggaggag atgaagacgc agctggaaga gctggaggac    4680
gagctgcaag ccacggagga cgccaaactg cggctggaag tcaacatgca ggcgctcaag    4740
ggccagttcg aaagggatct ccaagcccgg gacgagcaga atgaggagaa gaggaggcaa    4800
ctgcagagac agcttcacga gtatgagacg gaactggaag acgagcgaaa gcaacgtgcc    4860
ctggcagctg cagcaaagaa gaagctggaa ggggacctga agacctgga gcttcaggcc    4920 gactctgcca tcaagggggag ggaggaagcc atcaagcagc tacgcaaact gcaggctcag    4980
atgaaggact ttcaaagaga gctggaagat gcccgtgcct ccagagatga gatctttgcc    5040
acagccaaag agaatgagaa gaaagccaag agcttggaag cagacctcat gcagctacaa    5100
gaggacctcg ccgccgctga gagggctcgc aaacaagcgg acctcgagaa ggaggaactg    5160
gcagaggagc tggccagtag cctgtcggga aggaacgcac tccaggacga gaagcgccgc    5220
ctggaggccc ggatcgccca gctggaggag gagctgagg aggagcaggg caacatggag    5280
gccatgagcg accgggtccg caaagccaca cagcaggccg agcagctcag caacgagctg    5340
gccacagagc gcagcacggc ccagaagaat gagagtgccc ggcagcagct cgagcggcag    5400
aacaaggagc tccggagcaa gctccacgag atggaggggg ccgtcaagtc caagttcaag    5460
tccaccatcg cggcgctgga ggccaagatt gcacagctgg aggagcaggt cgagcaggag    5520
gccagagaga acaggcggc caccaagtcg ctgaagcaga agacaagaa gctgaaggaa    5580 atcttgctgc aggtggagga cgagcgcaag atggccgagc agtacaagga gcaggcagag    5640
aaaggcaatg ccagggtcaa gcagctcaag aggcagctgg aggaggcaga ggaggagtcc    5700
cagcgcatca cgccaaccg caggaagctg cagcgggagc tggatgaggc cacggagagc    5760
aacgaggcca tgggccgcga ggtgaacgca ctcaagagca agctcaggcg aggaaacgag    5820
acctctttcg ttccttctag aaggtctgga ggacgtagga ttattgaaaa tgcagatggt    5880
tctgaggagg aaacggacac tcgagacgca gacttcaatg gaaccaaggc cagtgaa      5937
```

<210> SEQ ID NO 4
<211> LENGTH: 1979
<212> TYPE: PRT
<213> ORGANISM: Homo sapiens

<400> SEQUENCE: 4

```
Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
```

-continued

```
                20                  25                  30
Lys Arg Leu Val Trp Val Pro Ser Glu Lys Gln Gly Phe Glu Ala Ala
            35                  40                  45
Ser Ile Lys Glu Glu Lys Gly Asp Glu Val Val Glu Leu Val Glu
        50                  55                  60
Asn Gly Lys Lys Val Thr Val Gly Lys Asp Asp Ile Gln Lys Met Asn
65                  70                  75                  80
Pro Pro Lys Phe Ser Lys Val Glu Asp Met Ala Glu Leu Thr Cys Leu
                85                  90                  95
Asn Glu Ala Ser Val Leu His Asn Leu Arg Glu Arg Tyr Phe Ser Gly
            100                 105                 110
Leu Ile Tyr Thr Tyr Ser Gly Leu Phe Cys Val Val Asn Pro Tyr
        115                 120                 125
Lys His Leu Pro Ile Tyr Ser Glu Lys Ile Val Asp Met Tyr Lys Gly
    130                 135                 140
Lys Lys Arg His Glu Met Pro Pro His Ile Tyr Ala Ile Ala Asp Thr
145                 150                 155                 160
Ala Tyr Arg Ser Met Leu Gln Asp Arg Glu Asp Gln Ser Ile Leu Cys
                165                 170                 175
Thr Gly Glu Ser Gly Ala Gly Lys Thr Glu Asn Thr Lys Lys Val Ile
            180                 185                 190
Gln Tyr Leu Ala Val Val Ala Ser Ser His Lys Gly Lys Lys Asp Thr
        195                 200                 205
Ser Ile Thr Gln Gly Pro Ser Phe Ala Tyr Gly Glu Leu Glu Lys Gln
    210                 215                 220
Leu Leu Gln Ala Asn Pro Ile Leu Glu Ala Phe Gly Asn Ala Lys Thr
225                 230                 235                 240
Val Lys Asn Asp Asn Ser Ser Arg Phe Gly Lys Phe Ile Arg Ile Asn
                245                 250                 255
Phe Asp Val Thr Gly Tyr Ile Val Gly Ala Asn Ile Glu Thr Tyr Leu
            260                 265                 270
Leu Glu Lys Ser Arg Ala Ile Arg Gln Ala Arg Asp Glu Arg Thr Phe
        275                 280                 285
His Ile Phe Tyr Tyr Met Ile Ala Gly Ala Lys Glu Lys Met Arg Ser
    290                 295                 300
Asp Leu Leu Leu Glu Gly Phe Asn Asn Tyr Thr Phe Leu Ser Asn Gly
305                 310                 315                 320
Phe Val Pro Ile Pro Ala Ala Gln Asp Asp Glu Met Phe Gln Glu Thr
                325                 330                 335
Val Glu Ala Met Ala Ile Met Gly Phe Ser Glu Glu Glu Gln Leu Ser
            340                 345                 350
Ile Leu Lys Val Val Ser Ser Val Leu Gln Leu Gly Asn Ile Val Phe
        355                 360                 365
Lys Lys Glu Arg Asn Thr Asp Gln Ala Ser Met Pro Asp Asn Thr Ala
    370                 375                 380
Ala Gln Lys Val Cys His Leu Met Gly Ile Asn Val Thr Asp Phe Thr
385                 390                 395                 400
Arg Ser Ile Leu Thr Pro Arg Ile Lys Val Gly Arg Asp Val Val Gln
                405                 410                 415
Lys Ala Gln Thr Lys Glu Gln Ala Asp Phe Ala Val Glu Ala Leu Ala
            420                 425                 430
Lys Ala Thr Tyr Glu Arg Leu Phe Arg Trp Ile Leu Thr Arg Val Asn
        435                 440                 445
```

-continued

```
Lys Ala Leu Asp Lys Thr His Arg Gln Gly Ala Ser Phe Leu Gly Ile
    450                 455                 460
Leu Asp Ile Ala Gly Phe Glu Ile Phe Glu Val Asn Ser Phe Glu Gln
465                 470                 475                 480
Leu Cys Ile Asn Tyr Thr Asn Glu Lys Leu Gln Gln Leu Phe Asn His
                485                 490                 495
Thr Met Phe Ile Leu Glu Gln Glu Tyr Gln Arg Glu Gly Ile Glu
            500                 505                 510
Trp Asn Phe Ile Asp Phe Gly Leu Asp Leu Gln Pro Cys Ile Glu Leu
            515                 520                 525
Ile Glu Arg Pro Asn Asn Pro Pro Gly Val Leu Ala Leu Leu Asp Glu
    530                 535                 540
Glu Cys Trp Phe Pro Lys Ala Thr Asp Lys Ser Phe Val Glu Lys Leu
545                 550                 555                 560
Cys Thr Glu Gln Gly Ser His Pro Lys Phe Gln Lys Pro Lys Gln Leu
                565                 570                 575
Lys Asp Lys Thr Glu Phe Ser Ile Ile His Tyr Ala Gly Lys Val Asp
            580                 585                 590
Tyr Asn Ala Ser Ala Trp Leu Thr Lys Asn Met Asp Pro Leu Asn Asp
    595                 600                 605
Asn Val Thr Ser Leu Leu Asn Ala Ser Ser Asp Lys Phe Val Ala Asp
    610                 615                 620
Leu Trp Lys Asp Val Asp Arg Ile Val Gly Leu Asp Gln Met Ala Lys
625                 630                 635                 640
Met Thr Glu Ser Ser Leu Pro Ser Ala Ser Lys Thr Lys Lys Gly Met
                645                 650                 655
Phe Arg Thr Val Gly Gln Leu Tyr Lys Glu Gln Leu Gly Lys Leu Met
            660                 665                 670
Thr Thr Leu Arg Asn Thr Thr Pro Asn Phe Val Arg Cys Ile Ile Pro
    675                 680                 685
Asn His Glu Lys Arg Ser Gly Lys Leu Asp Ala Phe Leu Val Leu Glu
    690                 695                 700
Gln Leu Arg Cys Asn Gly Val Leu Glu Gly Ile Arg Ile Cys Arg Gln
705                 710                 715                 720
Gly Phe Pro Asn Arg Ile Val Phe Gln Glu Phe Arg Gln Arg Tyr Glu
                725                 730                 735
Ile Leu Ala Ala Asn Ala Ile Pro Lys Gly Phe Met Asp Gly Lys Gln
            740                 745                 750
Ala Cys Ile Leu Met Ile Lys Ala Leu Glu Leu Asp Pro Asn Leu Tyr
    755                 760                 765
Arg Ile Gly Gln Ser Lys Ile Phe Phe Arg Thr Gly Val Leu Ala His
    770                 775                 780
Leu Glu Glu Glu Arg Asp Leu Lys Ile Thr Asp Val Ile Met Ala Phe
785                 790                 795                 800
Gln Ala Met Cys Arg Gly Tyr Leu Ala Arg Lys Ala Phe Ala Lys Arg
                805                 810                 815
Gln Gln Gln Leu Thr Ala Met Lys Val Ile Gln Arg Asn Cys Ala Ala
            820                 825                 830
Tyr Leu Lys Leu Arg Asn Trp Gln Trp Trp Arg Leu Phe Thr Lys Val
    835                 840                 845
Lys Pro Leu Leu Gln Val Thr Arg Gln Glu Glu Met Gln Ala Lys
850                 855                 860
```

-continued

```
Glu Asp Glu Leu Gln Lys Thr Lys Glu Arg Gln Gln Lys Ala Glu Asn
865                 870                 875                 880

Glu Leu Lys Glu Leu Glu Gln Lys His Ser Gln Leu Thr Glu Glu Lys
                885                 890                 895

Asn Leu Leu Gln Glu Gln Leu Gln Ala Glu Thr Glu Leu Tyr Ala Glu
            900                 905                 910

Ala Glu Glu Met Arg Val Arg Leu Ala Ala Lys Lys Gln Glu Leu Glu
        915                 920                 925

Glu Ile Leu His Glu Met Glu Ala Arg Leu Glu Glu Glu Asp Arg
    930                 935                 940

Gly Gln Gln Leu Gln Ala Glu Arg Lys Lys Met Ala Gln Gln Met Leu
945                 950                 955                 960

Asp Leu Glu Glu Gln Leu Glu Glu Glu Ala Ala Arg Gln Lys Leu
                965                 970                 975

Gln Leu Glu Lys Val Thr Ala Glu Ala Lys Ile Lys Lys Leu Glu Asp
            980                 985                 990

Glu Ile Leu Val Met Asp Asp Gln  Asn Asn Lys Leu Ser  Lys Glu Arg
        995                1000                 1005

Lys Leu  Leu Glu Glu Arg Ile  Ser Asp Leu Thr Thr  Asn Leu Ala
    1010                1015                 1020

Glu Glu  Glu Glu Lys Ala Lys  Asn Leu Thr Lys Leu  Lys Asn Lys
    1025                1030                 1035

His Glu  Ser Met Ile Ser Glu  Leu Glu Val Arg Leu  Lys Lys Glu
    1040                1045                 1050

Glu Lys  Ser Arg Gln Glu Leu  Glu Lys Leu Lys Arg  Lys Leu Glu
    1055                1060                 1065

Gly Asp  Ala Ser Asp Phe His  Glu Gln Ile Ala Asp  Leu Gln Ala
    1070                1075                 1080

Gln Ile  Ala Glu Leu Lys Met  Gln Leu Ala Lys Lys  Glu Glu Glu
    1085                1090                 1095

Leu Gln  Ala Ala Leu Ala Arg  Leu Asp Asp Glu Ile  Ala Gln Lys
    1100                1105                 1110

Asn Asn  Ala Leu Lys Lys Ile  Arg Glu Leu Glu Gly  His Ile Ser
    1115                1120                 1125

Asp Leu  Gln Glu Asp Leu Asp  Ser Glu Arg Ala Ala  Arg Asn Lys
    1130                1135                 1140

Ala Glu  Lys Gln Lys Arg Asp  Leu Gly Glu Glu Leu  Glu Ala Leu
    1145                1150                 1155

Lys Thr  Glu Leu Glu Asp Thr  Leu Asp Ser Thr Ala  Thr Gln Gln
    1160                1165                 1170

Glu Leu  Arg Ala Lys Arg Glu  Gln Glu Val Thr Val  Leu Lys Lys
    1175                1180                 1185

Ala Leu  Asp Glu Glu Thr Arg  Ser His Glu Ala Gln  Val Gln Glu
    1190                1195                 1200

Met Arg  Gln Lys His Ala Gln  Ala Val Glu Glu Leu  Thr Glu Gln
    1205                1210                 1215

Leu Glu  Gln Phe Lys Arg Ala  Lys Ala Asn Leu Asp  Lys Asn Lys
    1220                1225                 1230

Gln Thr  Leu Glu Lys Glu Asn  Ala Asp Leu Ala Gly  Glu Leu Arg
    1235                1240                 1245

Val Leu  Gly Gln Ala Lys Gln  Glu Val Glu His Lys  Lys Lys Lys
    1250                1255                 1260

Leu Glu  Ala Gln Val Gln Glu  Leu Gln Ser Lys Cys  Ser Asp Gly
```

```
                     1265                    1270                    1275
Glu Arg  Ala Arg Ala Glu  Leu Asn Asp Lys Val  His Lys Leu Gln
    1280                    1285                    1290

Asn Glu  Val Glu Ser Val  Thr Gly Met Leu Asn  Glu Ala Glu Gly
    1295                    1300                    1305

Lys Ala  Ile Lys Leu Ala  Lys Asp Val Ala Ser  Leu Ser Ser Gln
    1310                    1315                    1320

Leu Gln  Asp Thr Gln Glu  Leu Leu Gln Glu Glu  Thr Arg Gln Lys
    1325                    1330                    1335

Leu Asn  Val Ser Thr Lys  Leu Arg Gln Leu Glu  Glu Glu Arg Asn
    1340                    1345                    1350

Ser Leu  Gln Asp Gln Leu  Asp Glu Glu Met Glu  Ala Lys Gln Asn
    1355                    1360                    1365

Leu Glu  Arg His Ile Ser  Thr Leu Asn Ile Gln  Leu Ser Asp Ser
    1370                    1375                    1380

Lys Lys  Lys Leu Gln Asp  Phe Ala Ser Thr Val  Glu Ala Leu Glu
    1385                    1390                    1395

Glu Gly  Lys Lys Arg Phe  Gln Lys Glu Ile Glu  Asn Leu Thr Gln
    1400                    1405                    1410

Gln Tyr  Glu Glu Lys Ala  Ala Tyr Asp Lys Leu  Glu Lys Thr
    1415                    1420                    1425

Lys Asn  Arg Leu Gln Gln  Glu Leu Asp Asp Leu  Val Val Asp Leu
    1430                    1435                    1440

Asp Asn  Gln Arg Gln Leu  Val Ser Asn Leu Glu  Lys Lys Gln Arg
    1445                    1450                    1455

Lys Phe  Asp Gln Leu Leu  Ala Glu Glu Lys Asn  Ile Ser Ser Lys
    1460                    1465                    1470

Tyr Ala  Asp Glu Arg Asp  Arg Ala Glu Ala Glu  Ala Arg Glu Lys
    1475                    1480                    1485

Glu Thr  Lys Ala Leu Ser  Leu Ala Arg Ala Leu  Glu Glu Ala Leu
    1490                    1495                    1500

Glu Ala  Lys Glu Glu Leu  Glu Arg Thr Asn Lys  Met Leu Lys Ala
    1505                    1510                    1515

Glu Met  Glu Asp Leu Val  Ser Ser Lys Asp Asp  Val Gly Lys Asn
    1520                    1525                    1530

Val His  Glu Leu Glu Lys  Ser Lys Arg Ala Leu  Glu Thr Gln Met
    1535                    1540                    1545

Glu Glu  Met Lys Thr Gln  Leu Glu Glu Leu Glu  Asp Glu Leu Gln
    1550                    1555                    1560

Ala Thr  Glu Asp Ala Lys  Leu Arg Leu Glu Val  Asn Met Gln Ala
    1565                    1570                    1575

Leu Lys  Gly Gln Phe Glu  Arg Asp Leu Gln Ala  Arg Asp Glu Gln
    1580                    1585                    1590

Asn Glu  Glu Lys Arg Arg  Gln Leu Gln Arg Gln  Leu His Glu Tyr
    1595                    1600                    1605

Glu Thr  Glu Leu Glu Asp  Glu Arg Lys Gln Arg  Ala Leu Ala Ala
    1610                    1615                    1620

Ala Ala  Lys Lys Lys Leu  Glu Gly Asp Leu Lys  Asp Leu Glu Leu
    1625                    1630                    1635

Gln Ala  Asp Ser Ala Ile  Lys Gly Arg Glu Glu  Ala Ile Lys Gln
    1640                    1645                    1650

Leu Arg  Lys Leu Gln Ala  Gln Met Lys Asp Phe  Gln Arg Glu Leu
    1655                    1660                    1665
```

Glu Asp Ala Arg Ala Ser Arg Asp Glu Ile Phe Ala Thr Ala Lys
    1670                1675                1680

Glu Asn Glu Lys Lys Ala Lys Ser Leu Glu Ala Asp Leu Met Gln
    1685                1690                1695

Leu Gln Glu Asp Leu Ala Ala Ala Glu Arg Ala Arg Lys Gln Ala
    1700                1705                1710

Asp Leu Glu Lys Glu Glu Leu Ala Glu Glu Leu Ala Ser Ser Leu
    1715                1720                1725

Ser Gly Arg Asn Ala Leu Gln Asp Glu Lys Arg Arg Leu Glu Ala
    1730                1735                1740

Arg Ile Ala Gln Leu Glu Glu Glu Leu Glu Glu Glu Gln Gly Asn
    1745                1750                1755

Met Glu Ala Met Ser Asp Arg Val Arg Lys Ala Thr Gln Gln Ala
    1760                1765                1770

Glu Gln Leu Ser Asn Glu Leu Ala Thr Glu Arg Ser Thr Ala Gln
    1775                1780                1785

Lys Asn Glu Ser Ala Arg Gln Gln Leu Glu Arg Gln Asn Lys Glu
    1790                1795                1800

Leu Arg Ser Lys Leu His Glu Met Glu Gly Ala Val Lys Ser Lys
    1805                1810                1815

Phe Lys Ser Thr Ile Ala Ala Leu Glu Ala Lys Ile Ala Gln Leu
    1820                1825                1830

Glu Glu Gln Val Glu Gln Glu Ala Arg Glu Lys Gln Ala Ala Thr
    1835                1840                1845

Lys Ser Leu Lys Gln Lys Asp Lys Lys Leu Lys Glu Ile Leu Leu
    1850                1855                1860

Gln Val Glu Asp Glu Arg Lys Met Ala Glu Gln Tyr Lys Glu Gln
    1865                1870                1875

Ala Glu Lys Gly Asn Ala Arg Val Lys Gln Leu Lys Arg Gln Leu
    1880                1885                1890

Glu Glu Ala Glu Glu Glu Ser Gln Arg Ile Asn Ala Asn Arg Arg
    1895                1900                1905

Lys Leu Gln Arg Glu Leu Asp Glu Ala Thr Glu Ser Asn Glu Ala
    1910                1915                1920

Met Gly Arg Glu Val Asn Ala Leu Lys Ser Lys Leu Arg Arg Gly
    1925                1930                1935

Asn Glu Thr Ser Phe Val Pro Ser Arg Arg Ser Gly Gly Arg Arg
    1940                1945                1950

Val Ile Glu Asn Ala Asp Gly Ser Glu Glu Thr Asp Thr Arg
    1955                1960                1965

Asp Ala Asp Phe Asn Gly Thr Lys Ala Ser Glu
    1970                1975

<210> SEQ ID NO 5
<211> LENGTH: 2097
<212> TYPE: DNA
<213> ORGANISM: Homo sapiens

<400> SEQUENCE: 5
atggcgcaga agggccaact cagtgacgat gagaagttcc tctttgtgga caaaaacttc      60
atcaacagcc cagtggccca ggctgactgg gccgccaaga gactcgtctg ggtcccctcg     120
gagaagcagg gcttcgaggc agccagcatt aaggaggaga aggggatgga ggtggttgtg     180
gagctggtgg agaatggcaa gaaggtcacg gttgggaaag atgacatcca gaagatgaac     240

-continued

```
ccacccaagt ctccaaggt ggaggacatg gcggagctga cgtgcctcaa cgaagcctcc      300
gtgctacaca acctgaggga gcggtacttc tcagggctaa tatatacgta ctctggcctc      360
ttctgcgtgg tggtcaaccc ctataaacac ctgcccatct actcggagaa gatcgtcgac      420
atgtacaagg gcaagaagag gcacgagatg ccgcctcaca tctacgccat cgcagacacg      480
gcctaccgga gcatgcttca agatcgggag gaccagtcca ttctatgcac aggcgagtct      540
ggagccggga aaaccgaaaa caccaagaag gtcattcagt acctggccgt ggtggcctcc      600
tcccacaagg gcaagaaaga cacaagtatc acgcaaggcc catcttttgc ctacggagag      660
ctggaaaagc agcttctaca agcaaacccg attctggagg ctttcggcaa cgccaaaaca      720
gtgaagaacg acaactcctc acgattcggc aaattcatcc gcatcaactt cgacgtcacg      780
ggttacatcg tgggagccaa cattgagacc tatctgctag aaaaatcacg ggcaattcgc      840
caagccagag acgagaggac attccacatc ttttactaca tgattgctgg agccaaggag      900
aagatgagaa gtgacttgct tttggagggc ttcaacaact acaccttcct ctccaatggc      960
tttgtgccca tcccagcagc ccaggatgat gagatgttcc aggaaaccgt ggaggccatg     1020
gcaatcatgg gtttcagcga ggaggagcag ctatccatat tgaaggtggt atcatcggtc     1080
ctgcagcttg gaaatatcgt cttcaagaag gaaagaaaca cagaccaggc gtccatgcca     1140
gataacacag ctgctcagaa agtttgccac ctcatgggaa ttaatgtgac agatttcacc     1200
agatccatcc tcactcctcg tatcaaggtt gggcgagatg tggtacagaa agctcagaca     1260
aaagaacagg ctgactttgc tgtagaggct ttggccaagg caacatatga gcgccttttc     1320
cgctggatac tcacccgcgt gaacaaagcc ctggacaaga cccatcggca aggggcttcc     1380
ttcctgggga tcctggatat agctggattt gagatctttg aggtgaactc cttcgagcag     1440
ctgtgcatca actacaccaa cgagaagctg cagcagctct tcaaccacac catgttcatc     1500
ctggagcagg aggagtacca gcgcgagggc atcgagtgga acttcatcga ctttgggctg     1560
gacctacagc cctgcatcga gctcatcgag cgaccgaaca accctccagg tgtgctggcc     1620
ctgctggaca aggaatgctg gttccccaaa gccacggaca agtctttcgt ggagaagctg     1680
tgcacggagc agggcagcca ccccaagttc cagaagccca gcagctcaa ggacaagact     1740
gagttctcca tcatccatta tgctgggaag gtggactata tgcgagtgc ctggctgacc     1800
aagaatatgg acccgctgaa tgacaacgtg acttccctgc tcaatgcctc ctccgacaag     1860
tttgtggccg acctgtggaa ggacgtggac cgcatcgtgg gcctggacca gatggccaag     1920
atgacggaga gctcgctgcc cagcgcctcc aagaccaaga agggcatgtt ccgcacagtg     1980
gggcagctgt acaaggagca gctgggcaag ctgatgacca cgctacgcaa caccacgccc     2040
aacttcgtgc gctgcatcat ccccaaccac gagaagaggt ccggcaagct ggatgcg       2097
```

<210> SEQ ID NO 6
<211> LENGTH: 699
<212> TYPE: PRT
<213> ORGANISM: Homo sapiens

<400> SEQUENCE: 6

```
Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
            20                  25                  30

Lys Arg Leu Val Trp Val Pro Ser Glu Lys Gln Gly Phe Glu Ala Ala
        35                  40                  45
```

-continued

```
Ser Ile Lys Glu Glu Lys Gly Asp Glu Val Val Glu Leu Val Glu
         50                  55                  60

Asn Gly Lys Lys Val Thr Val Gly Lys Asp Asp Ile Gln Lys Met Asn
 65                  70                  75                  80

Pro Pro Lys Phe Ser Lys Val Glu Asp Met Ala Glu Leu Thr Cys Leu
                 85                  90                  95

Asn Glu Ala Ser Val Leu His Asn Leu Arg Glu Arg Tyr Phe Ser Gly
                100                 105                 110

Leu Ile Tyr Thr Tyr Ser Gly Leu Phe Cys Val Val Asn Pro Tyr
        115                 120                 125

Lys His Leu Pro Ile Tyr Ser Glu Lys Ile Val Asp Met Tyr Lys Gly
        130                 135                 140

Lys Lys Arg His Glu Met Pro Pro His Ile Tyr Ala Ile Ala Asp Thr
145                 150                 155                 160

Ala Tyr Arg Ser Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
                180                 185                 190

Gln Tyr Leu Ala Val Val Ala Ser Ser His Lys Gly Lys Lys Asp Thr
        195                 200                 205

Ser Ile Thr Gln Gly Pro Ser Phe Ala Tyr Gly Glu Leu Glu Lys Gln
        210                 215                 220

Leu Leu Gln Ala Asn Pro Ile Leu Glu Ala Phe Gly Asn Ala Lys Thr
225                 230                 235                 240

Val Lys Asn Asp Asn Ser Ser Arg Phe Gly Lys Phe Ile Arg Ile Asn
                245                 250                 255

Phe Asp Val Thr Gly Tyr Ile Val Gly Ala Asn Ile Glu Thr Tyr Leu
                260                 265                 270

Leu Glu Lys Ser Arg Ala Ile Arg Gln Ala Arg Asp Glu Arg Thr Phe
        275                 280                 285

His Ile Phe Tyr Tyr Met Ile Ala Gly Ala Lys Glu Lys Met Arg Ser
        290                 295                 300

Asp Leu Leu Leu Glu Gly Phe Asn Asn Tyr Thr Phe Leu Ser Asn Gly
305                 310                 315                 320

Phe Val Pro Ile Pro Ala Ala Gln Asp Asp Glu Met Phe Gln Glu Thr
                325                 330                 335

Val Glu Ala Met Ala Ile Met Gly Phe Ser Glu Glu Glu Gln Leu Ser
                340                 345                 350

Ile Leu Lys Val Val Ser Ser Val Leu Gln Leu Gly Asn Ile Val Phe
        355                 360                 365

Lys Lys Glu Arg Asn Thr Asp Gln Ala Ser Met Pro Asp Asn Thr Ala
        370                 375                 380

Ala Gln Lys Val Cys His Leu Met Gly Ile Asn Val Thr Asp Phe Thr
385                 390                 395                 400

Arg Ser Ile Leu Thr Pro Arg Ile Lys Val Gly Arg Asp Val Val Gln
                405                 410                 415

Lys Ala Gln Thr Lys Glu Gln Ala Asp Phe Ala Val Glu Ala Leu Ala
                420                 425                 430

Lys Ala Thr Tyr Glu Arg Leu Phe Arg Trp Ile Leu Thr Arg Val Asn
        435                 440                 445

Lys Ala Leu Asp Lys Thr His Arg Gln Gly Ala Ser Phe Leu Gly Ile
        450                 455                 460
```

```
Leu Asp Ile Ala Gly Phe Glu Ile Phe Glu Val Asn Ser Phe Glu Gln
465                 470                 475                 480

Leu Cys Ile Asn Tyr Thr Asn Glu Lys Leu Gln Gln Leu Phe Asn His
            485                 490                 495

Thr Met Phe Ile Leu Glu Gln Glu Glu Tyr Gln Arg Glu Gly Ile Glu
        500                 505                 510

Trp Asn Phe Ile Asp Phe Gly Leu Asp Leu Gln Pro Cys Ile Glu Leu
    515                 520                 525

Ile Glu Arg Pro Asn Asn Pro Pro Gly Val Leu Ala Leu Leu Asp Glu
530                 535                 540

Glu Cys Trp Phe Pro Lys Ala Thr Asp Lys Ser Phe Val Glu Lys Leu
545                 550                 555                 560

Cys Thr Glu Gln Gly Ser His Pro Lys Phe Gln Lys Pro Lys Gln Leu
                565                 570                 575

Lys Asp Lys Thr Glu Phe Ser Ile Ile His Tyr Ala Gly Lys Val Asp
            580                 585                 590

Tyr Asn Ala Ser Ala Trp Leu Thr Lys Asn Met Asp Pro Leu Asn Asp
        595                 600                 605

Asn Val Thr Ser Leu Leu Asn Ala Ser Ser Asp Lys Phe Val Ala Asp
    610                 615                 620

Leu Trp Lys Asp Val Asp Arg Ile Val Gly Leu Asp Gln Met Ala Lys
625                 630                 635                 640

Met Thr Glu Ser Ser Leu Pro Ser Ala Ser Lys Thr Lys Lys Gly Met
                645                 650                 655

Phe Arg Thr Val Gly Gln Leu Tyr Lys Glu Gln Leu Gly Lys Leu Met
            660                 665                 670

Thr Thr Leu Arg Asn Thr Thr Pro Asn Phe Val Arg Cys Ile Ile Pro
        675                 680                 685

Asn His Glu Lys Arg Ser Gly Lys Leu Asp Ala
    690                 695

<210> SEQ ID NO 7
<211> LENGTH: 2316
<212> TYPE: DNA
<213> ORGANISM: Homo sapiens

<400> SEQUENCE: 7
atggcgcaga agggccaact cagtgacgat gagaagttcc tctttgtgga caaaaacttc      60
atcaacagcc cagtggccca ggctgactgg gccgccaaga ctcgtctg ggtcccctcg      120 gagaagcagg gcttcgaggc agccagcatt aaggaggaga aggggaatga ggtggttgtg      180 agctggtgg agaatggcaa gaaggtcacg gttgggaaag atgacatcca agaagatgaac      240 ccacccaagt tctccaaggt ggaggacatg gcggagctga cgtgcctcaa cgaagcctcc      300
gtgctacaca acctgaggga gcggtactt caagggctaa tatactgta ctctggcctc      360 ttctgcgtgg tggtcaaccc ctataaacac ctgcccatct actcggagaa gatcgtcgac      420
atgtacaagg gcaagaagag gcacgagatg ccgcctcaca tctacgccat cgcagacacg      480
gcctaccgga gcatgcttca gatcgggag gaccagtcca ttctatgcac aggcgagtct      540
ggagccggga aaaccgaaaa caccaagaag gtcattcagt acctggccgt ggtggcctcc      600
tcccacaagg gcaagaaaga cacaagtatc acgcaaggcc atcttttgc ctacggagag      660 ctggaaaagc agcttctaca agcaaacccg attctggagg ctttcggcaa cgccaaaaca      720
gtgaagaacg acaactcctc acgattcggc aaattcatcc gcatcaactt cgacgtcacg      780
```

-continued

```
ggttacatcg tgggagccaa cattgagacc tatctgctag aaaaatcacg ggcaattcgc    840
caagccagag acgagaggac attccacatc ttttactaca tgattgctgg agccaaggag    900
aagatgagaa gtgacttgct tttggagggc ttcaacaact acaccttcct ctccaatggc    960
tttgtgccca tcccagcagc ccaggatgat gagatgttcc aggaaaccgt ggaggccatg   1020
gcaatcatgg gtttcagcga ggaggagcag ctatccatat tgaaggtggt atcatcggtc   1080
ctgcagcttg gaaatatcgt cttcaagaag gaaagaaaca cagaccaggc gtccatgcca   1140
gataacacag ctgctcagaa agtttgccac ctcatgggaa ttaatgtgac agatttcacc   1200
agatccatcc tcactcctcg tatcaaggtt gggcgagatg tggtacagaa agctcagaca   1260
aaagaacagg ctgactttgc tgtagaggct ttggccaagg caacatatga gcgcctttc    1320 cgctggatac tcacccgcgt gaacaaagcc ctggacaaga cccatcggca aggggcttcc   1380
ttcctgggga tcctggatat agctggattt gagatctttg aggtgaactc cttcgagcag   1440
ctgtgcatca actacaccaa cgagaagctg cagcagctct tcaaccacac catgttcatc   1500
ctggagcagg aggagtacca gcgcgagggc atcgagtgga acttcatcga ctttgggctg   1560
gacctacagc cctgcatcga gctcatcgag cgaccgaaca acctccagg tgtgctggcc    1620 ctgctggacg aggaatgctg gttccccaaa gccacggaca agtctttcgt ggagaagctg   1680
tgcacggagc agggcagcca ccccaagttc cagaagccca agcagctcaa ggacaagact   1740
gagttctcca tcatccatta tgctgggaag gtggactata atgcgagtgc ctggctgacc   1800
aagaatatgg acccgctgaa tgacaacgtg acttccctgc tcaatgcctc ctccgacaag   1860
tttgtggccg acctgtggaa ggacgtggac cgcatcgtgg gcctggacca gatggccaag   1920
atgacggaga gctcgctgcc cagcgcctcc aagaccaaga agggcatgtt ccgcacagtg   1980
gggcagctgt acaaggagca gctgggcaag ctgatgacca cgctacgcaa caccacgccc   2040
aacttcgtgc gctgcatcat ccccaaccac gagaagaggt ccggcaagct ggatgcgttc   2100
ctggtgctgg agcagctgcg gtgcaatggg gtgctggaag gcattcgcat ctgccggcag   2160
ggcttcccca accggatcgt cttccaggag ttccgccaac gctacagagat cctggcggcg   2220 aatgccatcc ccaaaggctt catggacggg aagcaggcct gcattctcat gatcaaagcc   2280
ctggaacttg accccaactt atacaggata gggcag                              2316
```

<210> SEQ ID NO 8
<211> LENGTH: 772
<212> TYPE: PRT
<213> ORGANISM: Homo sapiens

<400> SEQUENCE: 8

```
Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
            20                  25                  30

Lys Arg Leu Val Trp Val Pro Ser Glu Lys Gln Gly Phe Glu Ala Ala
        35                  40                  45

Ser Ile Lys Glu Glu Lys Gly Asp Glu Val Val Val Glu Leu Val Glu
    50                  55                  60

Asn Gly Lys Lys Val Thr Val Gly Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Arg Glu Arg Tyr Phe Ser Gly
```

-continued

```
                    100                 105                 110
Leu Ile Tyr Thr Tyr Ser Gly Leu Phe Cys Val Val Asn Pro Tyr
            115                 120                 125
Lys His Leu Pro Ile Tyr Ser Glu Lys Ile Val Asp Met Tyr Lys Gly
        130                 135                 140
Lys Lys Arg His Glu Met Pro Pro His Ile Tyr Ala Ile Ala Asp Thr
145                 150                 155                 160
Ala Tyr Arg Ser Met Leu Gln Asp Arg Glu Asp Gln Ser Ile Leu Cys
                165                 170                 175
Thr Gly Glu Ser Gly Ala Gly Lys Thr Glu Asn Thr Lys Lys Val Ile
                180                 185                 190
Gln Tyr Leu Ala Val Val Ala Ser His Lys Gly Lys Lys Asp Thr
            195                 200                 205
Ser Ile Thr Gln Gly Pro Ser Phe Ala Tyr Gly Glu Leu Glu Lys Gln
    210                 215                 220
Leu Leu Gln Ala Asn Pro Ile Leu Glu Ala Phe Gly Asn Ala Lys Thr
225                 230                 235                 240
Val Lys Asn Asp Asn Ser Ser Arg Phe Gly Lys Phe Ile Arg Ile Asn
                245                 250                 255
Phe Asp Val Thr Gly Tyr Ile Val Gly Ala Asn Ile Glu Thr Tyr Leu
            260                 265                 270
Leu Glu Lys Ser Arg Ala Ile Arg Gln Ala Arg Asp Glu Arg Thr Phe
        275                 280                 285
His Ile Phe Tyr Tyr Met Ile Ala Gly Ala Lys Glu Lys Met Arg Ser
    290                 295                 300
Asp Leu Leu Leu Glu Gly Phe Asn Asn Tyr Thr Phe Leu Ser Asn Gly
305                 310                 315                 320
Phe Val Pro Ile Pro Ala Ala Gln Asp Asp Glu Met Phe Gln Glu Thr
                325                 330                 335
Val Glu Ala Met Ala Ile Met Gly Phe Ser Glu Glu Gln Leu Ser
            340                 345                 350
Ile Leu Lys Val Val Ser Ser Val Leu Gln Leu Gly Asn Ile Val Phe
        355                 360                 365
Lys Lys Glu Arg Asn Thr Asp Gln Ala Ser Met Pro Asp Asn Thr Ala
    370                 375                 380
Ala Gln Lys Val Cys His Leu Met Gly Ile Asn Val Thr Asp Phe Thr
385                 390                 395                 400
Arg Ser Ile Leu Thr Pro Arg Ile Lys Val Gly Arg Asp Val Val Gln
                405                 410                 415
Lys Ala Gln Thr Lys Glu Gln Ala Asp Phe Ala Val Glu Ala Leu Ala
            420                 425                 430
Lys Ala Thr Tyr Glu Arg Leu Phe Arg Trp Ile Leu Thr Arg Val Asn
        435                 440                 445
Lys Ala Leu Asp Lys Thr His Arg Gln Gly Ala Ser Phe Leu Gly Ile
    450                 455                 460
Leu Asp Ile Ala Gly Phe Glu Ile Phe Glu Val Asn Ser Phe Glu Gln
465                 470                 475                 480
Leu Cys Ile Asn Tyr Thr Asn Glu Lys Leu Gln Gln Leu Phe Asn His
                485                 490                 495
Thr Met Phe Ile Leu Glu Gln Glu Glu Tyr Gln Arg Glu Gly Ile Glu
            500                 505                 510
Trp Asn Phe Ile Asp Phe Gly Leu Asp Leu Gln Pro Cys Ile Glu Leu
        515                 520                 525
```

```
Ile Glu Arg Pro Asn Asn Pro Pro Gly Val Leu Ala Leu Leu Asp Glu
    530                 535                 540
Glu Cys Trp Phe Pro Lys Ala Thr Asp Lys Ser Phe Val Glu Lys Leu
545                 550                 555                 560
Cys Thr Glu Gln Gly Ser His Pro Lys Phe Gln Lys Pro Lys Gln Leu
                565                 570                 575
Lys Asp Lys Thr Glu Phe Ser Ile Ile His Tyr Ala Gly Lys Val Asp
            580                 585                 590
Tyr Asn Ala Ser Ala Trp Leu Thr Lys Asn Met Asp Pro Leu Asn Asp
        595                 600                 605
Asn Val Thr Ser Leu Leu Asn Ala Ser Ser Asp Lys Phe Val Ala Asp
    610                 615                 620
Leu Trp Lys Asp Val Asp Arg Ile Val Gly Leu Asp Gln Met Ala Lys
625                 630                 635                 640
Met Thr Glu Ser Ser Leu Pro Ser Ala Ser Lys Thr Lys Lys Gly Met
                645                 650                 655
Phe Arg Thr Val Gly Gln Leu Tyr Lys Glu Gln Leu Gly Lys Leu Met
            660                 665                 670
Thr Thr Leu Arg Asn Thr Thr Pro Asn Phe Val Arg Cys Ile Ile Pro
        675                 680                 685
Asn His Glu Lys Arg Ser Gly Lys Leu Asp Ala Phe Leu Val Leu Glu
    690                 695                 700
Gln Leu Arg Cys Asn Gly Val Leu Glu Gly Ile Arg Ile Cys Arg Gln
705                 710                 715                 720
Gly Phe Pro Asn Arg Ile Val Phe Gln Glu Phe Arg Gln Arg Tyr Glu
                725                 730                 735
Ile Leu Ala Ala Asn Ala Ile Pro Lys Gly Phe Met Asp Gly Lys Gln
            740                 745                 750
Ala Cys Ile Leu Met Ile Lys Ala Leu Glu Leu Asp Pro Asn Leu Tyr
        755                 760                 765
Arg Ile Gly Gln
    770

<210> SEQ ID NO 9
<211> LENGTH: 2547
<212> TYPE: DNA
<213> ORGANISM: Homo sapiens

<400> SEQUENCE: 9
atggcgcaga agggccaact cagtgacgat gagaagttcc tctttgtgga caaaaacttc    60
atcaacagcc cagtggccca ggctgactgg gccgccaaga ctcgtctg ggtcccctcg     120 gagaagcagg gcttcgaggc agccagcatt aaggaggaga aggggatga ggtggttgtg    180 gagctggtgg agaatggcaa gaaggtcacg gttgggaaag atgacatcca agatgaac    240 ccacccaagt tctccaaggt ggaggacatg gcggagctga cgtgcctcaa cgaagcctcc    300
gtgctacaca acctgaggga gcggtacttc tcagggctaa tatatacgta ctctggcctc    360
ttctgcgtgg tggtcaaccc ctataaacac ctgcccatct actcggagaa gatcgtcgac    420
atgtacaagg gcaagaagag gcacgagatg ccgcctcaca tctacgccat cgcagacacg    480
gcctaccgga gcatgcttca agatcgggag gaccagtcca ttctatgcac aggcgagtct    540
ggagccggga aaaccgaaaa caccaagaag gtcattcagt acctggccgt ggtggcctcc    600
tcccacaagg gcaagaaaga cacaagtatc acgcaaggcc atctttttgc ctacggagag    660
```

-continued

```
ctggaaaagc agcttctaca agcaaacccg attctggagg ctttcggcaa cgccaaaaca    720
gtgaagaacg acaactcctc acgattcggc aaattcatcc gcatcaactt cgacgtcacg    780
ggttacatcg tgggagccaa cattgagacc tatctgctag aaaaatcacg ggcaattcgc    840
caagccagag acgagaggac attccacatc ttttactaca tgattgctgg agccaaggag    900
aagatgagaa gtgacttgct tttggagggc ttcaacaact acaccttcct ctccaatggc    960
tttgtgccca tcccagcagc ccaggatgat gagatgttcc aggaaaccgt ggaggccatg   1020
gcaatcatgg gtttcagcga ggaggagcag ctatccatat tgaaggtggt atcatcggtc   1080
ctgcagcttg gaaatatcgt cttcaagaag gaaagaaaca cagaccaggc gtccatgcca   1140
gataacacag ctgctcagaa agtttgccac ctcatgggaa ttaatgtgac agatttcacc   1200
agatccatcc tcactcctcg tatcaaggtt gggcgagatg tggtacagaa agctcagaca   1260
aaagaacagg ctgactttgc tgtagaggct ttggccaagg caacatatga gcgcctttc    1320 cgctggatac tcacccgcgt gaacaaagcc tggacaagac ccatcggca agggcttcc    1380 ttcctgggga tcctggatat agctggattt gagatctttg aggtgaactc cttcgagcag   1440
ctgtgcatca actacaccaa cgagaagctg cagcagctct tcaaccacac catgttcatc   1500
ctggagcagg aggagtacca gcgcgagggc atcgagtgga acttcatcga ctttgggctg   1560
gacctacagc cctgcatcga gctcatcgag cgaccgaaca accctccagg tgtgctggcc   1620
ctgctggacg aggaatgctg gttccccaaa gccacggaca agtctttcgt ggagaagctg   1680
tgcacggagc agggcagcca ccccaagttc cagaagccca gcagctcaa ggacaagact   1740 gagttctcca tcatccatta tgctgggaag gtggactata atgcgagtgc ctggctgacc   1800
aagaatatgg acccgctgaa tgacaacgtg acttccctgc tcaatgcctc ctccgacaag   1860
tttgtggccg acctgtggaa ggacgtggac cgcatcgtgg gcctggacca gatggccaag   1920
atgacggaga gctcgctgcc cagcgcctcc aagaccaaga agggcatgtt ccgcacagtg   1980
gggcagctgt acaaggagca gctgggcaag ctgatgacca cgctacgcaa caccacgccc   2040
aacttcgtgc gctgcatcat ccccaaccac gagaagaggt ccggcaagct ggatgcgttc   2100
ctggtgctgg agcagctgcg gtgcaatggg gtgctggaag gcattcgcat ctgccggcag   2160
ggcttcccca accggatcgt cttccaggag ttccgccaac gctacgagat cctggcggcg   2220
aatgccatcc ccaaaggctt catggacggg aagcaggcct gcattctcat gatcaaagcc   2280
ctggaacttg accccaactt atacaggata gggcagagca aaatcttctt ccgaactggc   2340
gtcctggccc acctagagga ggagcgagat ttgaagatca ccgatgtcat catggccttc   2400
caggcgatgt gtcgtggcta cttggccaga aaggcttttg ccaagaggca gcagcagctg   2460
accgccatga aggtgattca gaggaactgc gccgcctacc tcaagctgcg gaactggcag   2520
tggtggaggc ttttcaccaa agtgaag                                      2547
```

```
<210> SEQ ID NO 10
<211> LENGTH: 849
<212> TYPE: PRT
<213> ORGANISM: Homo sapiens

<400> SEQUENCE: 10
```

Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
            20                  25                  30

Lys Arg Leu Val Trp Val Pro Ser Glu Lys Gln Gly Phe Glu Ala Ala

-continued

```
             35                  40                  45
Ser Ile Lys Glu Glu Lys Gly Asp Glu Val Val Glu Leu Val Glu
         50                  55                  60
Asn Gly Lys Lys Val Thr Val Gly Lys Asp Asp Ile Gln Lys Met Asn
 65                  70                  75                  80
Pro Pro Lys Phe Ser Lys Val Glu Asp Met Ala Glu Leu Thr Cys Leu
                 85                  90                  95
Asn Glu Ala Ser Val Leu His Asn Leu Arg Glu Arg Tyr Phe Ser Gly
            100                 105                 110
Leu Ile Tyr Thr Tyr Ser Gly Leu Phe Cys Val Val Asn Pro Tyr
        115                 120                 125
Lys His Leu Pro Ile Tyr Ser Glu Lys Ile Val Asp Met Tyr Lys Gly
        130                 135                 140
Lys Lys Arg His Glu Met Pro Pro His Ile Tyr Ala Ile Ala Asp Thr
145                 150                 155                 160
Ala Tyr Arg Ser Met Leu Gln Asp Arg Glu Asp Gln Ser Ile Leu Cys
                165                 170                 175
Thr Gly Glu Ser Gly Ala Gly Lys Thr Glu Asn Thr Lys Lys Val Ile
            180                 185                 190
Gln Tyr Leu Ala Val Val Ala Ser Ser His Lys Gly Lys Lys Asp Thr
        195                 200                 205
Ser Ile Thr Gln Gly Pro Ser Phe Ala Tyr Gly Glu Leu Glu Lys Gln
        210                 215                 220
Leu Leu Gln Ala Asn Pro Ile Leu Glu Ala Phe Gly Asn Ala Lys Thr
225                 230                 235                 240
Val Lys Asn Asp Asn Ser Ser Arg Phe Gly Lys Phe Ile Arg Ile Asn
                245                 250                 255
Phe Asp Val Thr Gly Tyr Ile Val Gly Ala Asn Ile Glu Thr Tyr Leu
            260                 265                 270
Leu Glu Lys Ser Arg Ala Ile Arg Gln Ala Arg Asp Glu Arg Thr Phe
        275                 280                 285
His Ile Phe Tyr Tyr Met Ile Ala Gly Ala Lys Glu Lys Met Arg Ser
        290                 295                 300
Asp Leu Leu Leu Glu Gly Phe Asn Asn Tyr Thr Phe Leu Ser Asn Gly
305                 310                 315                 320
Phe Val Pro Ile Pro Ala Ala Gln Asp Asp Glu Met Phe Gln Glu Thr
                325                 330                 335
Val Glu Ala Met Ala Ile Met Gly Phe Ser Glu Glu Gln Leu Ser
            340                 345                 350
Ile Leu Lys Val Val Ser Ser Val Leu Gln Leu Gly Asn Ile Val Phe
        355                 360                 365
Lys Lys Glu Arg Asn Thr Asp Gln Ala Ser Met Pro Asp Asn Thr Ala
        370                 375                 380
Ala Gln Lys Val Cys His Leu Met Gly Ile Asn Val Thr Asp Phe Thr
385                 390                 395                 400
Arg Ser Ile Leu Thr Pro Arg Ile Lys Val Gly Arg Asp Val Val Gln
                405                 410                 415
Lys Ala Gln Thr Lys Glu Gln Ala Asp Phe Ala Val Glu Ala Leu Ala
            420                 425                 430
Lys Ala Thr Tyr Glu Arg Leu Phe Arg Trp Ile Leu Thr Arg Val Asn
        435                 440                 445
Lys Ala Leu Asp Lys Thr His Arg Gln Gly Ala Ser Phe Leu Gly Ile
        450                 455                 460
```

```
Leu Asp Ile Ala Gly Phe Glu Ile Phe Glu Val Asn Ser Phe Glu Gln
465                 470                 475                 480

Leu Cys Ile Asn Tyr Thr Asn Glu Lys Leu Gln Gln Leu Phe Asn His
                485                 490                 495

Thr Met Phe Ile Leu Glu Gln Glu Glu Tyr Gln Arg Glu Gly Ile Glu
            500                 505                 510

Trp Asn Phe Ile Asp Phe Gly Leu Asp Leu Gln Pro Cys Ile Glu Leu
        515                 520                 525

Ile Glu Arg Pro Asn Asn Pro Pro Gly Val Leu Ala Leu Leu Asp Glu
    530                 535                 540

Glu Cys Trp Phe Pro Lys Ala Thr Asp Lys Ser Phe Val Glu Lys Leu
545                 550                 555                 560

Cys Thr Glu Gln Gly Ser His Pro Lys Phe Gln Lys Pro Lys Gln Leu
                565                 570                 575

Lys Asp Lys Thr Glu Phe Ser Ile Ile His Tyr Ala Gly Lys Val Asp
            580                 585                 590

Tyr Asn Ala Ser Ala Trp Leu Thr Lys Asn Met Asp Pro Leu Asn Asp
        595                 600                 605

Asn Val Thr Ser Leu Leu Asn Ala Ser Ser Asp Lys Phe Val Ala Asp
    610                 615                 620

Leu Trp Lys Asp Val Asp Arg Ile Val Gly Leu Asp Gln Met Ala Lys
625                 630                 635                 640

Met Thr Glu Ser Ser Leu Pro Ser Ala Ser Lys Thr Lys Lys Gly Met
                645                 650                 655

Phe Arg Thr Val Gly Gln Leu Tyr Lys Glu Gln Leu Gly Lys Leu Met
            660                 665                 670

Thr Thr Leu Arg Asn Thr Thr Pro Asn Phe Val Arg Cys Ile Ile Pro
        675                 680                 685

Asn His Glu Lys Arg Ser Gly Lys Leu Asp Ala Phe Leu Val Leu Glu
    690                 695                 700

Gln Leu Arg Cys Asn Gly Val Leu Glu Gly Ile Arg Ile Cys Arg Gln
705                 710                 715                 720

Gly Phe Pro Asn Arg Ile Val Phe Gln Glu Phe Arg Gln Arg Tyr Glu
                725                 730                 735

Ile Leu Ala Ala Asn Ala Ile Pro Lys Gly Phe Met Asp Gly Lys Gln
            740                 745                 750

Ala Cys Ile Leu Met Ile Lys Ala Leu Glu Leu Asp Pro Asn Leu Tyr
        755                 760                 765

Arg Ile Gly Gln Ser Lys Ile Phe Phe Arg Thr Gly Val Leu Ala His
    770                 775                 780

Leu Glu Glu Glu Arg Asp Leu Lys Ile Thr Asp Val Ile Met Ala Phe
785                 790                 795                 800

Gln Ala Met Cys Arg Gly Tyr Leu Ala Arg Lys Ala Phe Ala Lys Arg
                805                 810                 815

Gln Gln Gln Leu Thr Ala Met Lys Val Ile Gln Arg Asn Cys Ala Ala
            820                 825                 830

Tyr Leu Lys Leu Arg Asn Trp Gln Trp Trp Arg Leu Phe Thr Lys Val
        835                 840                 845

Lys

<210> SEQ ID NO 11
<211> LENGTH: 2556
<212> TYPE: DNA
```

<213> ORGANISM: Homo sapiens

<400> SEQUENCE: 11

| | | | | | |
|---|---|---|---|---|---|
| atggcgcaga | agggccaact | cagtgacgat | gagaagttcc | tctttgtgga | caaaaacttc       60 |
| atcaacagcc | cagtggccca | ggctgactgg | gccgccaaga | gactcgtctg | ggtcccctcg      120 |
| gagaagcagg | gcttcgaggc | agccagcatt | aaggaggaga | aggggatga | ggtggttgtg      180 |
| gagctggtgg | agaatggcaa | gaaggtcacg | gttgggaaag | atgacatcca | agagatgaac      240 |
| ccacccaagt | tctccaaggt | ggaggacatg | gcggagctga | cgtgcctcaa | cgaagcctcc      300 |
| gtgctacaca | acctgaggga | gcggtacttc | tcagggctaa | tatatacgta | ctctggcctc      360 |
| ttctgcgtgg | tggtcaaccc | ctataaacac | ctgcccatct | actcggagaa | gatcgtcgac      420 |
| atgtacaagg | caagaagag | gcacgagatg | ccgcctcaca | tctacgccat | cgcagacacg      480 |
| gcctaccgga | gcatgcttca | agatcgggag | gaccagtcca | ttctatgcac | aggcgagtct      540 |
| ggagccggga | aaaccgaaaa | caccaagaag | gtcattcagt | acctggccgt | ggtggcctcc      600 |
| tcccacaagg | gcaagaaaga | cacaagtatc | acgcaaggcc | catcttttgc | ctacggagag      660 |
| ctggaaaagc | agcttctaca | agcaaacccg | attctggagg | ctttcggcaa | cgccaaaaca      720 |
| gtgaagaacg | acaactcctc | acgattcggc | aaattcatcc | gcatcaactt | cgacgtcacg      780 |
| ggttacatcg | tgggagccaa | cattgagacc | tatctgctag | aaaaatcacg | gcaattcgc       840 |
| caagccagag | acgagaggac | attccacatc | ttttactaca | tgattgctgg | agccaaggag      900 |
| aagatgagaa | gtgacttgct | tttggagggc | ttcaacaact | acaccttcct | ctccaatggc      960 |
| tttgtgccca | tcccagcagc | ccaggatgat | gagatgttcc | aggaaaccgt | ggaggccatg     1020 |
| gcaatcatgg | gtttcagcga | ggaggagcag | ctatccatat | tgaaggtggt | atcatcggtc     1080 |
| ctgcagcttg | gaaatatcgt | cttcaagaag | gaaagaaaca | cagaccaggc | gtccatgcca     1140 |
| gataacacag | ctgctcagaa | agtttgccac | ctcatgggaa | ttaatgtgac | agatttcacc     1200 |
| agatccatcc | tcactcctcg | tatcaaggtt | gggcgagatg | tggtacagaa | agctcagaca     1260 |
| aaagaacagg | ctgactttgc | tgtagaggct | ttggccaagg | caacatatga | gcgccttttc     1320 |
| cgctggatac | tcacccgcgt | gaacaaagcc | ctggacaaga | cccatcggca | aggggcttcc     1380 |
| ttcctgggga | tcctggatat | agctggattt | gagatctttg | aggtgaactc | cttcgagcag     1440 |
| ctgtgcatca | actacaccaa | cgagaagctg | cagcagctct | tcaaccacac | catgttcatc     1500 |
| ctggagcagg | aggagtacca | gcgcgaggc | atcgagtgga | acttcatcga | ctttgggctg     1560 |
| gacctacagc | cctgcatcga | gctcatcgag | cgaccgaaca | accctccagg | tgtgctggcc     1620 |
| ctgctggacg | aggaatgctg | gttccccaaa | gccacggaca | gtctttcgt | ggagaagctg     1680 |
| tgcacggagc | agggcagcca | ccccaagttc | cagaagccca | agcagctcaa | ggacaagact     1740 |
| gagttctcca | tcatccatta | tgctgggaag | gtggactata | tgcgagtgc | ctggctgacc     1800 |
| aagaatatgg | acccgctgaa | tgacaacgtg | acttccctgc | tcaatgcctc | ctccgacaag     1860 |
| tttgtggccg | acctgtggaa | ggacgtggac | cgcatcgtgg | gcctggacca | gatggccaag     1920 |
| atgacggaga | gctcgctgcc | cagcgcctcc | aagaccaaga | agggcatgtt | ccgcacagtg     1980 |
| gggcagctgt | acaaggagca | gctgggcaag | ctgatgacca | cgctacgcaa | caccacgccc     2040 |
| aacttcgtgc | gctgcatcat | ccccaaccac | gagaagaggt | ccggcaagct | ggatgcgttc     2100 |
| ctggtgctgg | agcagctgcg | gtgcaatggg | gtgctggaag | gcattcgcat | ctgccggcag     2160 |
| ggcttccca | accggatcgt | cttccaggag | ttccgccaac | gctacgagat | cctgcggcg     2220 |
| aatgccatcc | ccaaaggctt | catggacggg | aagcaggcct | gcattctcat | gatcaaagcc     2280 |

-continued

```
ctggaacttg accccaactt atacaggata gggcagagca aaatcttctt ccgaactggc    2340
gtcctggccc acctagagga ggagcgagat ttgaagatca ccgatgtcat catggccttc    2400
caggcgatgt gtcgtggcta cttggccaga aaggcttttg ccaagaggca gcagcagctg    2460
accgccatga aggtgattca gaggaactgc gccgcctacc tcaagctgcg gaactggcag    2520
tggtggaggc ttttcaccaa agtgaagcca ctgctg                             2556
```

<210> SEQ ID NO 12
<211> LENGTH: 852
<212> TYPE: PRT
<213> ORGANISM: Homo sapiens

<400> SEQUENCE: 12

```
Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
            20                  25                  30

Lys Arg Leu Val Trp Val Pro Ser Glu Lys Gln Gly Phe Glu Ala Ala
        35                  40                  45

Ser Ile Lys Glu Glu Lys Gly Asp Glu Val Val Val Glu Leu Val Glu
    50                  55                  60

Asn Gly Lys Lys Val Thr Val Gly Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Arg Glu Arg Tyr Phe Ser Gly
            100                 105                 110

Leu Ile Tyr Thr Tyr Ser Gly Leu Phe Cys Val Val Val Asn Pro Tyr
        115                 120                 125

Lys His Leu Pro Ile Tyr Ser Glu Lys Ile Val Asp Met Tyr Lys Gly
    130                 135                 140

Lys Lys Arg His Glu Met Pro Pro His Ile Tyr Ala Ile Ala Asp Thr
145                 150                 155                 160

Ala Tyr Arg Ser Met Leu Gln Asp Arg Glu Asp Gln Ser Ile Leu Cys
                165                 170                 175

Thr Gly Glu Ser Gly Ala Gly Lys Thr Glu Asn Thr Lys Lys Val Ile
            180                 185                 190

Gln Tyr Leu Ala Val Val Ala Ser Ser His Lys Gly Lys Lys Asp Thr
        195                 200                 205

Ser Ile Thr Gln Gly Pro Ser Phe Ala Tyr Gly Glu Leu Glu Lys Gln
    210                 215                 220

Leu Leu Gln Ala Asn Pro Ile Leu Glu Ala Phe Gly Asn Ala Lys Thr
225                 230                 235                 240

Val Lys Asn Asp Asn Ser Ser Arg Phe Gly Lys Phe Ile Arg Ile Asn
                245                 250                 255

Phe Asp Val Thr Gly Tyr Ile Val Gly Ala Asn Ile Glu Thr Tyr Leu
            260                 265                 270

Leu Glu Lys Ser Arg Ala Ile Arg Gln Ala Arg Asp Glu Arg Thr Phe
        275                 280                 285

His Ile Phe Tyr Tyr Met Ile Ala Gly Ala Lys Glu Lys Met Arg Ser
    290                 295                 300

Asp Leu Leu Leu Glu Gly Phe Asn Asn Tyr Thr Phe Leu Ser Asn Gly
305                 310                 315                 320
```

-continued

```
Phe Val Pro Ile Pro Ala Ala Gln Asp Asp Glu Met Phe Gln Glu Thr
                325                 330                 335
Val Glu Ala Met Ala Ile Met Gly Phe Ser Glu Glu Glu Gln Leu Ser
            340                 345                 350
Ile Leu Lys Val Val Ser Ser Val Leu Gln Leu Gly Asn Ile Val Phe
        355                 360                 365
Lys Lys Glu Arg Asn Thr Asp Gln Ala Ser Met Pro Asp Asn Thr Ala
    370                 375                 380
Ala Gln Lys Val Cys His Leu Met Gly Ile Asn Val Thr Asp Phe Thr
385                 390                 395                 400
Arg Ser Ile Leu Thr Pro Arg Ile Lys Val Gly Arg Asp Val Val Gln
                405                 410                 415
Lys Ala Gln Thr Lys Glu Gln Ala Asp Phe Ala Val Glu Ala Leu Ala
            420                 425                 430
Lys Ala Thr Tyr Glu Arg Leu Phe Arg Trp Ile Leu Thr Arg Val Asn
        435                 440                 445
Lys Ala Leu Asp Lys Thr His Arg Gln Gly Ala Ser Phe Leu Gly Ile
    450                 455                 460
Leu Asp Ile Ala Gly Phe Glu Ile Phe Glu Val Asn Ser Phe Glu Gln
465                 470                 475                 480
Leu Cys Ile Asn Tyr Thr Asn Glu Lys Leu Gln Gln Leu Phe Asn His
                485                 490                 495
Thr Met Phe Ile Leu Glu Gln Glu Glu Tyr Gln Arg Glu Gly Ile Glu
            500                 505                 510
Trp Asn Phe Ile Asp Phe Gly Leu Asp Leu Gln Pro Cys Ile Glu Leu
        515                 520                 525
Ile Glu Arg Pro Asn Asn Pro Pro Gly Val Leu Ala Leu Leu Asp Glu
    530                 535                 540
Glu Cys Trp Phe Pro Lys Ala Thr Asp Lys Ser Phe Val Glu Lys Leu
545                 550                 555                 560
Cys Thr Glu Gln Gly Ser His Pro Lys Phe Gln Lys Pro Lys Gln Leu
                565                 570                 575
Lys Asp Lys Thr Glu Phe Ser Ile Ile His Tyr Ala Gly Lys Val Asp
            580                 585                 590
Tyr Asn Ala Ser Ala Trp Leu Thr Lys Asn Met Asp Pro Leu Asn Asp
        595                 600                 605
Asn Val Thr Ser Leu Leu Asn Ala Ser Ser Asp Lys Phe Val Ala Asp
    610                 615                 620
Leu Trp Lys Asp Val Asp Arg Ile Val Gly Leu Asp Gln Met Ala Lys
625                 630                 635                 640
Met Thr Glu Ser Ser Leu Pro Ser Ala Ser Lys Thr Lys Lys Gly Met
                645                 650                 655
Phe Arg Thr Val Gly Gln Leu Tyr Lys Glu Gln Leu Gly Lys Leu Met
            660                 665                 670
Thr Thr Leu Arg Asn Thr Thr Pro Asn Phe Val Arg Cys Ile Ile Pro
        675                 680                 685
Asn His Glu Lys Arg Ser Gly Lys Leu Asp Ala Phe Leu Val Leu Glu
    690                 695                 700
Gln Leu Arg Cys Asn Gly Val Leu Glu Gly Ile Arg Ile Cys Arg Gln
705                 710                 715                 720
Gly Phe Pro Asn Arg Ile Val Phe Gln Glu Phe Arg Gln Arg Tyr Glu
                725                 730                 735
Ile Leu Ala Ala Asn Ala Ile Pro Lys Gly Phe Met Asp Gly Lys Gln
```

```
                740             745             750
Ala Cys Ile Leu Met Ile Lys Ala Leu Glu Leu Asp Pro Asn Leu Tyr
        755                 760                 765
Arg Ile Gly Gln Ser Lys Ile Phe Phe Arg Thr Gly Val Leu Ala His
        770                 775                 780
Leu Glu Glu Arg Asp Leu Lys Ile Thr Asp Val Ile Met Ala Phe
785                 790                 795                 800
Gln Ala Met Cys Arg Gly Tyr Leu Ala Arg Lys Ala Phe Ala Lys Arg
                805                 810                 815
Gln Gln Gln Leu Thr Ala Met Lys Val Ile Gln Arg Asn Cys Ala Ala
                820                 825                 830
Tyr Leu Lys Leu Arg Asn Trp Gln Trp Trp Arg Leu Phe Thr Lys Val
        835                 840                 845
Lys Pro Leu Leu
        850

<210> SEQ ID NO 13
<211> LENGTH: 2535
<212> TYPE: DNA
<213> ORGANISM: Homo sapiens

<400> SEQUENCE: 13
atggcgcaga agggccaact cagtgacgat gagaagttcc tctttgtgga caaaaacttc     60
atcaacagcc cagtggccca ggctgactgg ccgccaaga  gactcgtctg ggtcccctcg    120
gagaagcagg gcttcgaggc agccagcatt aaggaggaga aggggggatga ggtggttgtg    180 gagctggtgg agaatggcaa gaaggtcacg gttgggaaag atgacatcca gaagatgaac    240
ccacccaagt tctccaaggt ggaggacatg gcggagctga cgtgcctcaa cgaagcctcc    300
gtgctacaca acctgaggga gcggtacttc tcagggctaa tatatacgta ctctggcctc    360
ttctgcgtgt tggtcaaccc ctataaaaca ctgcccatct actcggagaa gatcgtcgac    420
atgtacaagg gcaagaagag gcacgagatg ccgcctcaca tctacgccat cgcagacacg    480
gcctaccgga gcatgcttca gatcgggag gaccagtcca ttctatgcac aggcgagtct    540
ggagccggga aaaccgaaaa caccaagaag gtcattcagt acctggccgt ggtggcctcc    600
tcccacaagg gcaagaaaga cacaagtatc acgggagagc tggaaaagca gcttctacaa    660
gcaaacccga ttctggaggc tttcggcaac gccaaaacag tgaagaacga caactcctca    720
cgattcggca aattcatccg catcaacttc gacgtcacgg gttacatcgt gggagccaac    780
attgagacct atctgctaga aaaatcacgg gcaattcgcc aagccagaga cgagaggaca    840
ttccacatct tttactacat gattgctgga gccaaggaga gatgagaag  tgacttgctt    900 ttggagggct tcaacaacta caccttcctc tccaatggct tgtgcccat  cccagcagcc    960 caggatgatg agatgttcca ggaaaccgtg gaggccatgg caatcatggg tttcagcgag   1020
gaggagcagc tatccatatt gaaggtggta tcatcggtcc tgcagcttgg aaatatcgtc   1080
ttcaagaagg aaagaaacac agaccaggcg tccatgccag ataacacagc tgctcagaaa   1140
gtttgccacc tcatgggaat taatgtgaca gatttcacca gatccatcct cactcctcgt   1200
atcaaggttg ggcgagatgt ggtacagaaa gctcagacaa agaacaggc  tgactttgct   1260 gtagaggctt tggccaaggc aacatatgag cgccttttcc gctggatact cacccgcgtg   1320
aacaaagccc tggacaagac ccatcggcaa ggggcttcct tcctgggat  cctggatata   1380 gctggatttg agatctttga ggtgaactcc ttcgagcagc tgtgcatcaa ctacaccaac   1440
```

-continued

```
gagaagctgc agcagctctt caaccacacc atgttcatcc tggagcagga ggagtaccag    1500
cgcgagggca tcgagtggaa cttcatcgac tttgggctgg acctacagcc ctgcatcgag    1560
ctcatcgagc gaccgaacaa ccctccaggt gtgctggccc tgctggacga ggaatgctgg    1620
ttccccaaag ccacggacaa gtctttcgtg gagaagctgt gcacggagca gggcagccac    1680
cccaagttcc agaagcccaa gcagctcaag gacaagactg agttctccat catccattat    1740
gctgggaagg tggactataa tgcgagtgcc tggctgacca agaatatgga cccgctgaat    1800
gacaacgtga cttccctgct caatgcctcc tccgacaagt tgtggccga cctgtggaag    1860 gacgtggacc gcatcgtggg cctggaccag atggccaaga tgacgagag ctcgctgccc    1920 agcgcctcca agaccaagaa gggcatgttc cgcacagtgg ggcagctgta caaggagcag    1980
ctgggcaagc tgatgaccac gctacgcaac accacgccca acttcgtgcg ctgcatcatc    2040
cccaaccacg agaagaggtc cggcaagctg gatgcgttcc tggtgctgga gcagctgcgg    2100
tgcaatgggg tgctggaagg cattcgcatc tgccggcagg gcttccccaa ccggatcgtc    2160
ttccaggagt tccgccaacg ctacgagatc ctggcggcga atgccatccc caaaggcttc    2220
atggacggga gcaggcctg cattctcatg atcaaagccc tggaacttga ccccaactta    2280
tacaggatag ggcagagcaa aatcttcttc cgaactggcg tcctggccca cctagaggag    2340
gagcgagatt tgaagatcac cgatgtcatc atggccttcc aggcgatgtg tcgtggctac    2400
ttggccagaa aggcttttgc caagaggcag cagcagctga ccgccatgaa ggtgattcag    2460
aggaactgcg ccgcctacct caagctgcgg aactggcagt ggtggaggct tttcaccaaa    2520
gtgaagccac tgctg                                                    2535
```

<210> SEQ ID NO 14
<211> LENGTH: 699
<212> TYPE: PRT
<213> ORGANISM: Homo sapiens

<400> SEQUENCE: 14

```
Met Ala Gln Lys Gly Gln Leu Ser Asp Asp Glu Lys Phe Leu Phe Val
1               5                   10                  15

Asp Lys Asn Phe Ile Asn Ser Pro Val Ala Gln Ala Asp Trp Ala Ala
            20                  25                  30

Lys Arg Leu Val Trp Val Pro Ser Glu Lys Gln Gly Phe Glu Ala Ala
        35                  40                  45

Ser Ile Lys Glu Glu Lys Gly Asp Glu Val Val Glu Leu Val Glu
    50                  55                  60

Asn Gly Lys Lys Val Thr Val Gly Lys Asp Asp Ile Gln Lys Met Asn
65                  70                  75                  80

Pro Pro Lys Phe Ser Lys Val Glu Asp Met Ala Glu Leu Thr Cys Leu
                85                  90                  95

Asn Glu Ala Ser Val Leu His Asn Leu Arg Glu Arg Tyr Phe Ser Gly
            100                 105                 110

Leu Ile Tyr Thr Tyr Ser Gly Leu Phe Cys Val Val Val Asn Pro Tyr
        115                 120                 125

Lys His Leu Pro Ile Tyr Ser Glu Lys Ile Val Asp Met Tyr Lys Gly
    130                 135                 140

Lys Lys Arg His Glu Met Pro Pro His Ile Tyr Ala Ile Ala Asp Thr
145                 150                 155                 160

Ala Tyr Arg Ser Met Leu Gln Asp Arg Glu Asp Gln Ser Ile Leu Cys
                165                 170                 175
```

```
Thr Gly Glu Ser Gly Ala Gly Lys Thr Glu Asn Thr Lys Lys Val Ile
                180                 185                 190

Gln Tyr Leu Ala Val Val Ala Ser Ser His Lys Gly Lys Lys Asp Thr
            195                 200                 205

Ser Ile Thr Gln Gly Pro Ser Phe Ala Tyr Gly Glu Leu Glu Lys Gln
        210                 215                 220

Leu Leu Gln Ala Asn Pro Ile Leu Glu Ala Phe Gly Asn Ala Lys Thr
225                 230                 235                 240

Val Lys Asn Asp Asn Ser Ser Arg Phe Gly Lys Phe Ile Arg Ile Asn
                245                 250                 255

Phe Asp Val Thr Gly Tyr Ile Val Gly Ala Asn Ile Glu Thr Tyr Leu
            260                 265                 270

Leu Glu Lys Ser Arg Ala Ile Arg Gln Ala Arg Asp Glu Arg Thr Phe
        275                 280                 285

His Ile Phe Tyr Tyr Met Ile Ala Gly Ala Lys Glu Lys Met Arg Ser
        290                 295                 300

Asp Leu Leu Leu Glu Gly Phe Asn Asn Tyr Thr Phe Leu Ser Asn Gly
305                 310                 315                 320

Phe Val Pro Ile Pro Ala Ala Gln Asp Asp Glu Met Phe Gln Glu Thr
                325                 330                 335

Val Glu Ala Met Ala Ile Met Gly Phe Ser Glu Glu Glu Gln Leu Ser
            340                 345                 350

Ile Leu Lys Val Val Ser Ser Val Leu Gln Leu Gly Asn Ile Val Phe
        355                 360                 365

Lys Lys Glu Arg Asn Thr Asp Gln Ala Ser Met Pro Asp Asn Thr Ala
    370                 375                 380

Ala Gln Lys Val Cys His Leu Met Gly Ile Asn Val Thr Asp Phe Thr
385                 390                 395                 400

Arg Ser Ile Leu Thr Pro Arg Ile Lys Val Gly Arg Asp Val Val Gln
                405                 410                 415

Lys Ala Gln Thr Lys Glu Gln Ala Asp Phe Ala Val Glu Ala Leu Ala
            420                 425                 430

Lys Ala Thr Tyr Glu Arg Leu Phe Arg Trp Ile Leu Thr Arg Val Asn
        435                 440                 445

Lys Ala Leu Asp Lys Thr His Arg Gln Gly Ala Ser Phe Leu Gly Ile
    450                 455                 460

Leu Asp Ile Ala Gly Phe Glu Ile Phe Glu Val Asn Ser Phe Glu Gln
465                 470                 475                 480

Leu Cys Ile Asn Tyr Thr Asn Glu Lys Leu Gln Gln Leu Phe Asn His
                485                 490                 495

Thr Met Phe Ile Leu Glu Gln Glu Glu Tyr Gln Arg Glu Gly Ile Glu
            500                 505                 510

Trp Asn Phe Ile Asp Phe Gly Leu Asp Leu Gln Pro Cys Ile Glu Leu
        515                 520                 525

Ile Glu Arg Pro Asn Asn Pro Pro Gly Val Leu Ala Leu Leu Asp Glu
    530                 535                 540

Glu Cys Trp Phe Pro Lys Ala Thr Asp Lys Ser Phe Val Glu Lys Leu
545                 550                 555                 560

Cys Thr Glu Gln Gly Ser His Pro Lys Phe Gln Lys Pro Lys Gln Leu
                565                 570                 575

Lys Asp Lys Thr Glu Phe Ser Ile Ile His Tyr Ala Gly Lys Val Asp
            580                 585                 590

Tyr Asn Ala Ser Ala Trp Leu Thr Lys Asn Met Asp Pro Leu Asn Asp
```

-continued

```
                595                 600                 605
Asn Val Thr Ser Leu Leu Asn Ala Ser Ser Asp Lys Phe Val Ala Asp
        610                 615                 620

Leu Trp Lys Asp Val Asp Arg Ile Val Gly Leu Asp Gln Met Ala Lys
625                 630                 635                 640

Met Thr Glu Ser Ser Leu Pro Ser Ala Ser Lys Thr Lys Lys Gly Met
                645                 650                 655

Phe Arg Thr Val Gly Gln Leu Tyr Lys Glu Gln Leu Gly Lys Leu Met
                660                 665                 670

Thr Thr Leu Arg Asn Thr Thr Pro Asn Phe Val Arg Cys Ile Ile Pro
        675                 680                 685

Asn His Glu Lys Arg Ser Gly Lys Leu Asp Ala
        690                 695

<210> SEQ ID NO 15
<211> LENGTH: 7
<212> TYPE: PRT
<213> ORGANISM: Homo sapiens

<400> SEQUENCE: 15

Gln Gly Pro Ser Phe Ala Tyr
1               5

<210> SEQ ID NO 16
<211> LENGTH: 8
<212> TYPE: PRT
<213> ORGANISM: Homo sapiens

<400> SEQUENCE: 16

Cys Thr Glu Gln Gly Ser His Pro
1               5

<210> SEQ ID NO 17
<211> LENGTH: 21
<212> TYPE: DNA
<213> ORGANISM: Homo sapiens

<400> SEQUENCE: 17
caaggcccat cttttgccta c                                              21
```

HUMAN SMOOTH MUSCLE MYOSIN HEAVY CHAIN

CROSS-REFERENCE TO RELATED APPLICATION

This application is the U.S. National Stage of International Application No. PCT/US02/25563, filed Aug. 9, 2002, which is a continuation-in-part of U.S. application Ser. No. 09/927,597, filed Aug. 10, 2001, now U.S. Pat. No. 6,974,688, which is incorporated by reference in its entirety for all purposes.

FIELD OF THE INVENTION

The invention relates to the identification, purification, and isolation of a novel polynucleotides encoding a human protein, termed hSMMyHC, that is the human smooth muscle myosin heavy chain. The invention relates to polynucleotides encoding hSMMyHC polypeptides, hSMMyHC polynucleotides which specifically hybridize to a naturally-occurring hSMMyHC gene or mRNA sequence, oligonucleotide primers for amplifying a naturally-occurring hSMMyHC gene or mRNA sequence, substantially purified hSMMyHC polypeptides and polynucleotides, methods and compositions for detecting hSMMyHC polypeptides and polynucleotides, methods and compositions for identifying agents which modulate hSMMyHC functional interactions and/or activities, and methods of treating or preventing disease by modulating hSMMyHC functional interactions or activities.

BACKGROUND OF THE INVENTION

Smooth muscle cells form the contractile element found in involuntary contractile organs such as the gastrointestinal tract, the urogenital tract, the vasculature, and the small airways of the lung. Smooth muscle is capable of slow, sustained contractions that require less energy to maintain than other muscle types.

Smooth muscle cells are quite different from either skeletal or cardiac muscle cells, beginning with their smaller size. Additionally, no striations are seen in smooth muscle cells, and high-resolution microscopy reveals that smooth muscle cells lack the sarcomeric organization of other muscle cell types. The thick (myosin) and thin (actin) filaments are dispersed throughout the cytoplasm of smooth muscle cells, in contrast to the well-organized parallel bundles seen in skeletal and cardiac sarcomeres. This unique organization has the advantage of allowing smooth muscle cells to contract to less than ⅕ of their resting lengths (L0), compared with ½ L0 for cardiac cells.

The contractile apparatus of smooth muscle cells consists of thick filaments of smooth muscle myosin and thin filaments of actin coated with the smooth muscle isoform of tropomyosin. As in other muscle types, the level of intracellular free calcium regulates force production in smooth muscle. The molecular mechanism by which calcium controls force production is different in smooth muscle than in striated muscle.

Primary control of smooth muscle myosin activity is via calcium-dependent phosphorylation of myosin, changing inactive thick filaments into an active conformation that can interact with actin and produce force. This differs from skeletal and cardiac muscle, where regulation occurs at the level of actin thin filaments. In these tissues, tropomyosin and the regulatory troponin complex decorate actin filaments and control access to myosin binding sites, and thus force production, in a calcium-sensitive manner. In smooth muscle, there is evidence suggesting that some degree of thin filament regulation occurs in smooth muscle cells, but the regulatory proteins are different (caldesmon, calponin) and their role has been less well defined than for the troponin complex in skeletal and cardiac muscle.

Myosin is present in all muscle and non-muscle cells. Of the ten distinct classes of myosin in human cells, myosin-II is the form responsible for contraction of skeletal, cardiac, and smooth muscle. This form of myosin is significantly different in amino acid composition and in overall structure from myosins in the other nine distinct classes (Goodson and Spudich, 1993). Myosin-II consists of two globular head domains, called Subfragment-1 or S1, linked together by a long— helical coiled—coiled tail. Proteolysis of myosin generates either S1 or heavy meromyosin (HMM, a two-headed form with a truncated tail), depending on conditions. S1 contains the ATPase and actin-binding properties of the molecule. S1 has been shown to be sufficient to move actin filaments in vitro, and is therefore clearly the motor domain of the molecule.

Although myosin II isoforms from various tissues differ in a number of biological properties, they all share the same basic molecular structure as a dimer of two heavy chains (approximately 200 kDa) noncovlantly associated with two pairs of light chains (approximately 20 and 17 kDa). The two globular amino-terminal heads are tethered together by the carboxyl-terminal alpha-helical coiled-coil that forms a tail. The tails are involved in the assembly of myosin molecules into filaments, whereas the heads contain an actin-activated $Mg^{2+}$-ATPase activity. Each myosin head can be divided by three protease-sensitive regions into peptides of approximately 25, 50, and 20 kDa. The more amino-terminal 25 kDa-50 kDa junction is close to the ATP binding region, whereas the actin-binding domain is near the 50 kDa-20 kDa junction.

The high-resolution crystal structure for skeletal S1 is known in both its putative pre-stroke and post-stroke states. The crystal structure of the recombinant chicken smooth muscle myosin motor domain has also been determined. S1 consists of a globular actin binding and nucleotide binding region known as the catalytic domain. This domain is attached at its carboxy-terminus to an alpha-helix that has two light chains of ~20 kDa each wrapped around it. This light-chain binding domain of S1 is known as the lever arm. Upon transitioning from the pre-stroke to the post-stroke state of the S1, the lever arm swings through an angle of ~90 degrees about a fulcrum point in the catalytic domain near the nucleotide-binding site. The "power stroke" is driven by the hydrolysis of ATP.

The other end of the myosin molecule is an alpha-helical coiled-coiled tail involved in self assembly of myosin molecules into bipolar thick filaments. These thick filaments interdigitate between thinner actin filaments, and the two filament systems slide past one another during contraction of the muscle. This filament sliding mechanism involves conformational changes in the myosin heads causing them to walk along the thin actin filaments at the expense of ATP hydrolysis.

Activation of smooth muscle myosin is via phosphorylation of the 20 kDa myosin light chain by myosin light chain kinase (MLCK). Calcium sensitivity is achieved by the absolute requirement for having a Ca2+-calmodulin complex bound to MLCK. An increase in intracellular calcium drives formation of a calcium-calmodulin complex, which is then competent to bind to MLCK and stimulate phosphorylation. When calcium levels fall, the intracellular concentration of the Ca2+-calmodulin complex drops and more Ca2+-calmodulin dissociates from MLCK, causing inactivation. Counterbalancing the action of MLCK is myosin phosphatase, which dephosphorylates the 20 kDa myosin light chain and inactivates myosin.

Myosin heavy chain (MyHC) has been studied at the molecular level in striated muscle, where each isoform is encoded by a different member of a multigene family. In contrast, smooth muscle myosin heavy chain isoforms are produced by alternate splicing of a single gene. Of particular interest is the splice varriant that occurs in the myosin head, at the 25/50 kDa junction. B-isoforms contain an extra seven amino acid. insert at this junction; this insertion doubles the rate of ATP hydrolysis as well as the velocity of actin filaments in an in vitro motility assay over that of A-isoforms lacking the insert. Interestingly, although A- and B-isoforms are co-expressed in several smooth muscle types, there appears to be preferential expression of particular isoforms in different tissues. For example, the slower A-isoform predominates in vascular tissue, while the faster B-isoform is the major species in visceral tissues like bladder and intestine. This correlates with the much lower maximal speed of shortening seen for aortic versus intestinal smooth muscle.

In addition to this N-terminal diversity, there is also splice site variation in the C-terminal tail of the heavy chain, producing the SM-1 and SM-2 isoforms. The SM-2 isoform contains 9 unique amino acids, whereas the SM-1 isoform contains 43 unique amino acids at the C-terminus. The functional consequences of these C-terminal variations remain unclear, but expression studies indicate that there is differential expression in developing smooth muscle and cultured cells. SM-1 is expressed first in fetal rabbit development, followed by SM-2 expression in late fetal or early neonatal development. Studies of SM-1 and SM-2 isoform composition in different smooth muscle tissues have not established clear tissue expression patterns.

Although the art has provided some structural and functional data regarding certain non-primate homologs of SMMyHC genes, mRNAs, and encoded proteins, there is a need in the art for primate, and particularly human, SMMyHC isoform polynucleotide sequences, peptide sequences, isoform proteins, antibodies thereto, and the like, as well as methods employing the aforesaid. The present invention provides those embodiments and others useful to those skilled in the art.

The references discussed herein are provided solely for their disclosure prior to the filing date of the present application and are each incorporated herein by reference. Nothing herein is to be construed as an admission that the inventors are not entitled to antedate such disclosure by virtue of prior invention.

SUMMARY OF THE INVENTION

The present invention relates to novel human smooth muscle myosin heavy chain (hSMMyHC) proteins and encoding polynucleotides.

Accordingly, an embodiment of the invention involves the formation of a purified and/or isolated primate hSMMyHC protein and fragments thereof.

In an embodiment, the hSMMyHC polypeptides have the amino acid sequence of SEQ ID NO:4, SEQ ID NO:6, SEQ ID NO:8, SEQ ID NO:10, or SEQ ID NO:12, or a substantially identical mutein, homolog, fragment, analog, or fusion protein thereof.

In an aspect, the hSMMyHC protein comprises the polypeptide encoded by SEQ ID NO:1; SEQ ID NO:3; SEQ ID NO:5; SEQ ID NO:7, SEQ ID NO:9, SEQ ID NO:11, or SEQ ID NO:13; or a substantially identical mutein, homolog, fragment, analog, or fusion protein thereof.

The invention provides muteins comprising a hSMMyHC S1 domain comprising an amino acid sequence having an amino acid substitution, addition, and/or deletion as compared to a naturally-occurring hSMMyHC protein (e.g., a naturally-occurring hSMMyHC protein obtained from a non-pathological mammalian specimen). In a variation, the invention provides hSMMyHC fragments comprising a S1 or RLC binding domain (or fragments thereof), preferably S1, wherein said fragments comprise a naturally-occurring hSM-MyHC amino acid sequence and exhibit binding to ATP and/or actin, or wherein such fragments comprise an amino acid substitution, addition, or deletion relative to the naturally-occurring hSMMyHC polypeptide sequence and which substantially lack binding to actin or ATP, and/or have activity as a hSMMyHC competitive antagonist and/or enhance actin-myosin contractile activity or block actin-myosin contractile activity of endogenous hSMMyHC protein.

In an aspect, the invention provides recombinant proteins comprising an hSMMyHC sequence and an additional linked amino acid sequence in the form of a fusion protein. In an aspect, the invention provides deletion variants of hSM-MyHC wherein up to 90 percent or more of the fall-length hSMMyHC sequence is deleted but the deletion variant retains a detectable biochemical property (e.g., ATPase function, actin binding, etc.) and is structurally distinguishable from a corresponding fragment of a non-primate homolog of hSMMyHC. In an aspect the invention provides sequence variants of hSMMyHC wherein amino acid deletions, additions, and/or substitutions are present and wherein the sequence variant is not sequence identical to any known non-primate SMMyHC sequence of comparable length. In one aspect, the hSMMyHC protein comprises the amino acid sequence -QGPSFAY- (SEQ ID NO:15) (i.e., the insertion in the motor domain derived from the splice variant as described below).

The present invention provides compositions comprising recombinant and/or substantially purified hSMMyHC proteins and assay compositions comprising a hSMMyHC protein or variant thereof and a candidate agent which may modulate function of the hSMMyHC protein.

The invention also provides antibodies which bind to hSM-MyHC with an affinity of about at least $1 \times 10^7$ M$^{-1}$ and which lack specific high affinity binding for non-primate SMMyHC-related polypeptides.

Polynucleotide sequences encoding hSMMyHC polypeptides are provided. The characteristics of the cloned sequences are given, including the nucleotide and predicted amino acid sequences. Polynucleotides comprising these sequences can serve as templates for the recombinant expression of quantities of hSMMyHC polypeptides, such as full-length hSMMyHC. Many polynucleotides comprising these sequences can also serve as probes for nucleic acid hybridization.

The invention also provides host cells expressing hSM-MyHC polypeptides encoded by a polynucleotide other than a naturally-occurring hSMMyHC gene or homolog gene of the host cell (if present). Such a polynucleotide may be an expression vector.

The invention provides a method for identifying a candidate agent that modulates a detectable biochemical function of hSMMyHC in vitro. The present invention provides several novel methods and compositions for modulating hSM-MyHC activities and for screening for modulators of such activities. The invention also provides methods for identifying agents which modulate hSMMyHC activity in vivo.

The present invention also provides a method for diagnosing a disease in a human patient, wherein a diagnostic assay is used to determine if a predetermined pathogenomonic concentration of hSMMyHC polypeptide or its encoding mRNA is present in a biological sample from a human patient.

A further understanding of the nature and advantages of the invention will become apparent by reference to the remaining portions of the specification and drawings.

BRIEF DESCRIPTION OF THE DRAWINGS

FIG. 1(A-D) shows a cDNA sequence (SEQ ID NO:1) of a hSMMyHC variant.

FIG. 2(A-B) shows the amino acid sequence (SEQ ID NO:2) encoded by SEQ ID NO:1.

FIG. 3(A-D) shows a cDNA sequence (SEQ ID NO:3) of a hSMMyHC variant.

FIG. 4(A-B) shows the amino acid sequence (SEQ ID NO:4) encoded by SEQ ID NO:3.

FIG. 5(A-B) shows a cDNA sequence (SEQ ID NO:5) encoding a hSMMyHC variant having the sequence of amino acids 1-699 of SEQ ID NO:2.

FIG. 6 shows the amino acid sequence (SEQ ID NO:6) of a hSMMyHC variant having the sequence of amino acids 1-699 of SEQ ID NO:2.

FIG. 7(A-B) shows a cDNA sequence (SEQ ID NO:7) encoding a hSMMyHC variant having the sequence of amino acids 1-772 of SEQ ID NO:2.

FIG. 8 shows the amino acid sequence (SEQ ID NO:8) of a hSMMyHC variant having the sequence of amino acids 1-772 of SEQ ID NO:2.

FIG. 9(A-B) shows a cDNA sequence (SEQ ID NO:9) encoding a hSMMyHC variant having the sequence of amino acids 1-849 of SEQ ID NO:2.

FIG. 10 shows the amino acid sequence (SEQ ID NO:10) of a hSMMyHC variant having the sequence of amino acids 1-849 of SEQ ID NO:2.

FIG. 11(A-B) shows a cDNA sequence (SEQ ID NO:11) encoding a hSMMyHC variant having the sequence of amino acids 1-852 of SEQ ID NO:2.

FIG. 12 shows the amino acid sequence (SEQ ID NO:12) of a hSMMyHC variant having the sequence of amino acids 1-852 of SEQ ID NO:2.

FIG. 13(A-B) shows a cDNA sequence (SEQ ID NO:13) encoding a hSMMyHC variant having the sequence of amino acids 1-845 of SEQ ID NO:2.

FIG. 14 shows the amino acid sequence (SEQ ID NO:14) of a hSMMyHC variant having the sequence of amino acids 1-845 of SEQ ID NO:2.

DESCRIPTION OF THE PREFERRED EMBODIMENTS

I. General

Before the present proteins, nucleotide sequences, and methods are described, it is understood that this invention is not limited to the particular methodology, protocols, cell lines, vectors, and reagents described, as these may vary. It is also to he understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

As used herein, the twenty conventional amino acids and their abbreviations follow conventional usage (*Immunology—A Synthesis,* 2nd Edition, E. S. Golub and D. R. Gren, Eds., Sinauer Associates, Sunderland, Massachusetts (1991)). Stereoisomers (e.g., D-amino acids) of the twenty conventional amino acids, unnatural amino acids such as alpha-disubstituted amino acids, N-alkyl amino acids, lactic acid, and other unconventional amino acids may also be suitable components for polypeptides of the present invention. Examples of unconventional amino acids include: 4-hydroxyproline, gamma-carboxyglutamate, epsilon-N,N,N-trimethyllysine, epsilon-N-acetyllysine, O-phosphoserine, N-acetylserine, N-formylmethionine, 3-methylhistidine, 5-hydroxylysine, omega-N-methylarginine, and other similar amino acids and imino acids (e.g., 4-hydroxyproline). In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

"Actin polypeptide" is used herein as a generic term to refer to native protein, fragments, analogs, or fusions of actin, preferably mammal actin.

"Agent" or "candidate agent" is used herein to denote a chemical compound, a mixture of chemical compounds, an array of spatially localized compounds, a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues that modulates the activity of hSMMyHC. Agents are evaluated for potential activity by inclusion in screening assays described hereinbelow. Agents are evaluated for potential activity as specific protein interaction modulators and/or as specific modulators of protein or protein derivative catalytic activity and/or as specific modulators of the interactions between the protein of interest and potential accessory molecules required for protein catalysis (e.g., modulation of the interaction of the protein and ATP, $Mg^{+2}$, etc.) by inclusion in screening assays described hereinbelow. A preferred agent selectively modulates (i.e., inhibits or activates) a binding interaction between two predetermined polypeptides but does not substantially interfere with cell viability.

"Analog", "mutein" or "mutant" as used herein refers to polypeptides which are comprised of a segment of at least 10 amino acids that has substantial identity to a portion of the naturally occurring protein. For example, a hSMMyHC analog comprises a segment of at least 10 amino acids that has substantial identity to a hSMMyHC protein, such as the hSMMyHC protein of SEQ ID NO:2; preferably a deduced amino acid sequence of a primate hSMMyHC cDNA. Typically, analog polypeptides comprise a conservative amino acid substitution (or addition or deletion) with respect to the naturally-occurring sequence. Analogs typically are at least 20 amino acids long, preferably at least 50 amino acids long or longer, most usually being as long as full-length naturally-occurring protein. Some analogs may lack a biological activity but may still be employed for various uses, such as for raising antibodies to hSMMyHC epitopes, as an immunological reagent to detect and/or purify -hSMMyHC antibodies by affinity chromatography, or as a competitive or noncompetitive agonist, antagonist, or partial agonist of native hSMMyHC protein function.

"Asthma" is art recognized and includes the state in which excessive smooth muscle contraction of the airways in the lungs of a subject occurs.

"Cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

For identifying whether a nucleic acid or polypeptide is within the scope of the invention, the default parameters of the BLAST programs are suitable. The BLASTN program (for nucleotide sequences) uses as defaults a word length (W) of 11, an expectation (E) of 10, M=5, N=-4, and a comparison of both strands. For amino acid sequences, the BLASTP program uses as defaults a word length (W) of 3, an expectation (E) of 10, and the BLOSUM62 scoring matrix. The TBLATN program (using protein sequence for nucleotide sequence) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

The term "corresponds to" means that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

"Fragment" refers to a polypeptide that has an amino-terminal and/or carboxy-terminal deletion, but where the remaining amino acid sequence is identical to the corresponding positions in the sequence deduced from a full-length cDNA sequence (e.g., SEQ ID NO:2; SEQ ID NO:4; SEQ ID NO:6; SEQ ID NO:8, SEQ ID NO:10, SEQ ID NO:12, or SEQ ID NO:14). Fragments typically are at least 14 amino acids long, preferably at least 20 amino acids long, usually at least 50 amino acids long or longer, up to the length of a full-length naturally-occurring hSMMyHC polypeptide.

"hSMMyHC" refers to the human hSMMyHC gene and human hSMMyHC proteins, including isoforms thereof, unless otherwise identified; in its narrowest usage hSMMyHC refers to a hSMMyHC polynucleotide and polypeptide sequences having exact sequence identity with the coding sequences SEQ ID NO:1, SEQ ID NO:3, SEQ ID NO:5, SEQ ID NO:7, SEQ ID NO:9, SEQ ID NO:11, or SEQ ID NO:13; or the encoded sequences SEQ ID NO:2; SEQ ID NO:4; SEQ ID NO:6; SEQ ID NO:8, SEQ ID NO:10, SEQ ID NO:12, or SEQ ID NO:14.

"hSMMyHC antagonist" refers to agents which inhibit hSMMyHC activity and can produce a cell phenotype characteristic of cells having reduced or undetectable expression or function of hSMMyHC. Such antagonists typically will reduce contractility in a contractility assay employing hSMMyHC. In contradistinction, hSMMyHC agonists will enhance contractile activity and will usually increase actin-dependent and/or calcium-dependent ATP hydrolysis.

"hSMMyHC native protein" or "full-length hSMMyHC protein" refers to a full-length hSMMyHC polypeptide as shown herein (SEQ ID NO:2) or as naturally occurs in a primate species (e.g., human, simian, etc.).

"hSMMyHC polynucleotide" refers to a polynucleotide of at least 15 nucleotides wherein the polynucleotide comprises a segment of at least 15 nucleotides which: (1) are at least 55 percent identical to a naturally-occurring hSMMyHC mRNA sequence or its complement or to a naturally-occurring hSMMyHC genomic structural gene sequence (as described below), and/or (2) encode a hSMMyHC polypeptide. Due to the degeneracy of the genetic code, some hSMMyHC polynucleotides encoding a hSMMyHC polypeptide will be less than 55 percent identical to a naturally-occurring hSMMyHC polynucleotide. The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0). Similarly, some hSMMyHC polynucleotides which are suitable as hybridization probes, PCR primers, LCR amplimers, and the like will not encode a hSMMyHC polypeptide.

"hSMMyHC polypeptide" is a generic term referring to native protein, fragments, or analogs of hSMMyHC, or such fused to a second polypeptide sequence (e.g., an epitope tag, -gal, or other fusion). Hence, native hSMMyHC, fragments of hSMMyHC, and analogs of hSMMyHC, as well as hSMMyHC fusion proteins are species of the hSMMyHC polypeptide genus.

"Hypotension" is art recognized and includes the state in which insufficient smooth muscle contraction of a blood vessel occurs which results in hypotension in a subject.

"Hypertension" is art recognized and includes the state in which excessive smooth muscle contraction of a blood vessel occurs which results in hypertension in a subject.

"Incontinence" is art recognized and includes the state in which excessive smooth muscle contraction of the urinary tract occurs.

"Indicator composition" is intended to include any composition that can be used to screen and identify modulating agents. The indicator composition can be, for example, a smooth muscle cell, a smooth muscle cell extract, or a detergent-skinned smooth muscle fiber bundle system. The indicator composition can also be, for example, a biochemical preparations including actin filaments, enzyme systems, and the like. Methods for the preparation of intact smooth muscle cells or extracts from such cells are well known in the art and previously described (Glukhova et al. 1987. Tissue Cell 19:657-63; Childs et al. 1992. J. Biol. Chem. 267:22853-9, 1992; White et al. 1996. J. Biol. Chem. 271:15008-17). Methods for preparing Triton-skinned smooth muscle fiber bundles are also known in the art (Strauss et al. 1992. Am. J. Physiol. 262:1437-45; Van Eyk, J. E. et al. 1998. Circ. Res. 82:261-271).

The terms "interacting polypeptide segment" and "interacting polypeptide sequence" refer to a portion of a hybrid protein which can form a specific binding interaction with a portion of a second hybrid protein under suitable binding conditions. Generally, a portion of the first hybrid protein preferentially binds to a portion of the second hybrid protein forming a heterodimer or higher order heteromultimer comprising the first and second hybrid proteins; the binding portions of each hybrid protein are termed interacting polypeptide segments. Generally, interacting polypeptides can form heterodimers with a dissociation constant ($K_D$) of at least about $1 \times 10^3$ $M^{-1}$, usually at least $1 \times 10^4$ $M^{-1}$, typically at least $1 \times 10^5$ $M^{-1}$, preferably at least $1 \times 10^6$ $M^{-1}$ to $1 \times 10^7$ $M^{-1}$ or more, under suitable physiological conditions.

"Irritable bowel syndrome" is art recognized and includes the state in which excessive smooth muscle contraction of the gastrointestinal tract occurs.

"Label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides and glycoproteins are known in the art and may be used. Examples of labels for polypeptides include, but are not limited to, the following: radioisotopes (e.g., $^3H$, $^{14}C$, $^{35}S$, $^{125}I$, $^{131}I$), fluorescent labels (e.g., FITC, rhodamine, lanthanide phosphors), enzymatic labels (e.g., horseradish peroxidase, beta-galactosidase, luciferase, alkaline phosphatase), biotinyl groups, predetermined polypeptide epitopes recognized by a secondary reporter (e.g., leucine zipper pair sequences, binding sites for secondary antibodies, transcriptional activator polypeptide, metal binding domains, epitope tags). In some embodiments, labels are attached by spacer arms of various lengths to reduce potential steric hindrance.

"Menstrual cramps" are art recognized and include the state in which excessive smooth muscle contraction of the uterus occurs.

"Modulating smooth muscle contraction" is intended to include the capacity to inhibit or stimulate smooth muscle contraction to various levels, e.g., which allows for the treatment of targeted states. It is also intended to include the inducement of relaxation of smooth muscle, e.g., total relaxation, and the contraction of smooth muscle which is in relaxed state and it is desired to have the muscle in a more contracted state, e.g., the sphincter in esophageal reflux. The modulation can be complete inhibitor or partial inhibition. The modulation includes, modulation to the extent necessary or sufficient to treat the states described herein.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

"Normal blood" or "normal human blood" refers to blood from a healthy human individual who does not have an active disease or other disorder.

The terms "pathogenomonic concentration", "pathogenomonic amount", and "pathogenomonic staining pattern" refer to a concentration, amount, or localization pattern, respectively, of a hSMMyHC protein or mRNA in a sample, that indicates the presence of a pathological (e.g., asthmatic, hypertensive, etc.) condition or a predisposition to developing a disease. A pathogenomonic amount is an amount of a hSMMyHC protein or hSMMyHC mRNA in a cell or cellular sample that falls outside the range of normal clinical values that is established by prospective and/or retrospective statistical clinical studies. Generally, an individual having a disease will exhibit an amount of hSMMyHC protein or mRNA in a cell or tissue sample that is outside the range of concentrations that characterize normal, undiseased individuals; typically the pathogenomonic concentration is at least about one standard deviation outside the mean normal value, more usually it is at least about two standard deviations or more above the mean normal value. However, essentially all clinical diagnostic tests produce some percentage of false positives and false negatives. The sensitivity and selectivity of the diagnostic assay must be sufficient to satisfy the diagnostic objective and any relevant regulatory requirements. In general, the diagnostic methods of the invention are used to identify individuals as disease candidates, providing an additional parameter in a differential diagnosis of disease made by a competent health professional.

"Physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50-200 mM NaCl or KCl, pH 6.5-8.5, 20-45 C and 0.001-10 mM divalent cation (e.g., $Mg^{++}$, $Ca^{++}$); preferably about 150 mM NaCl or KCl, pH 7.2-7.6, 5 mM divalent cation, and often include 0.01-1.0 percent nonspecific protein (e.g., BSA). A non-ionic detergent (Tween, NP-40, Triton X-100) can often be present, usually at about 0.001 to 2%, typically 0.05-0.2% (v/v). Particular aqueous conditions may be selected by the practitioner according to conventional methods. For general guidance, the following buffered aqueous conditions may be applicable: 10-250 mM NaCl, 5-50 mM Tris HCl, pH 5-8, with optional addition of divalent cation(s) and/or metal chelators and/or nonionic detergents and/or membrane fractions and/or antifoam agents and/or scintillants.

"Premature labor" is art recognized. Tocolytic agents inhibit labor, slow down or halt the contractions of the uterus. Tocolytic agents used to treat premature labor and permit pregnancy to procede and so permit the fetus to gain in size and maturity before being born.

"Protein interaction inhibitor" refers to an agent which is identified by one or more screening method(s) of the invention as an agent which selectively inhibits protein-protein binding between a first interacting polypeptide and a second interacting polypeptide. Some protein interaction inhibitors may have therapeutic potential as drugs for human use and/or may serve as commercial reagents for laboratory research or bioprocess control. Protein interaction inhibitors which are candidate drugs are then tested further for activity in assays which are routinely used to predict suitability for use as human and veterinary drugs, including in vivo administration to non-human animals and often including administration to human in approved clinical trials.

"Recombinant" refers to hSMMyHC or other proteins produced by recombinant DNA techniques wherein the gene coding for protein is cloned by known recombinant DNA technology. For example, the human gene for hSMMyHC may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as SEQ ID NO:1, SEQ ID NO:3, SEQ ID NO:5, SEQ ID NO:7, SEQ ID NO:9, SEQ ID NO:11, or SEQ ID NO:13, or may comprise a complete cDNA or gene sequence. A full-length cDNA or gene sequence is defined as a polynucleotide containing the sequence(s) necessary to encode a complete protein product, including a translation initiation codon and a translation termination codon, unless linked to another encoding sequence in a format for production as a fusion protein. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of SEQ ID NO:1, SEQ ID NO:3, SEQ ID NO:5, SEQ ID NO:7, SEQ ID NO:9, SEQ ID NO:11, or SEQ ID NO:13.

"Smooth muscle" is intended to include smooth muscle sensitive to the agents of the present invention. Smooth muscle is sensitive to an agent if the agent modulates the contraction of the smooth muscle. Examples of smooth muscle include smooth muscle of a blood vessel, the airways of the lungs, the gastro-intestinal tract, the uterus, and the urinary tract.

"Specific hybridization" is defined herein as the formation of hybrids between a probe polynucleotide (e.g., a polynucleotide of the invention which may include substitutions, deletion, and/or additions) and a specific target polynucleotide wherein the probe preferentially hybridizes to the specific target such that, for example, a single band corresponding to one or more of the RNA species of hSMMyHC (or alternatively spliced mRNA species) can be identified on a Northern blot of RNA prepared from a suitable cell source (e.g., a somatic cell expressing hSMMyHC).

"Stringent" conditions are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent such as formamide, for example, 50% (v/v) formamide with 0.1% bovine serum alburmin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding moieties typically have an affinity for one another of at least $10^6$ M$^{-1}$. Preferred antibodies for use in diagnostics or therapeutics often have high affinities such as $10^7$, $10^8$, $10^9$ or $10^{10}$ M$^{-1}$.

"State" is art recognized and includes a disorder, disease or state characterized by the contraction of smooth muscle.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Substantially pure" means an object species is removed from its natural environment. Usually, the object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The nomenclature used hereafter and the laboratory procedures in cell culture, molecular genetics, and nucleic acid chemistry and hybridization described below may involve well known and commonly employed procedures in the art. Standard techniques are used for recombinant nucleic acid methods, polynucleotide synthesis, and microbial culture and transformation (e.g., electroporation, lipofection). The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y.

II. The Invention

Applicants are the first to provide new human smooth muscle myosins, the polynucleotide encoding them, and sequences thereof, for diagnosis, prevention, or treatment of vascular, pulmonary, reproductive, and immunological disorders.

A. Polypeptide

The present invention provides an isolated hSMMyHC polypeptide. Preferably, the polypeptide will comprise at least 50 contiguous amino acids of SEQ ID NO:2; SEQ ID NO:4; SEQ ID NO:6; SEQ ID NO:8; SEQ ID NO:10; SEQ ID NO:12; or SEQ ID NO:14. More preferably, the polypeptide comprises SEQ ID NO:2; SEQ ID NO:4; SEQ ID NO:6; SEQ ID NO:8; SEQ ID NO:10;, SEQ ID NO:12; or SEQ ID NO:14; or a substantially identical mutein, fragment, homolog, analog, or fusion protein thereof. According to a preferred embodiment, the polypeptide comprises the sequence —QGPSFAY—(i.e., SEQ ID NO:15; the insertion in the motor domain derived from the splice variant as described below). The polypeptides of this invention can also be fused in polypeptide linkage to a heterologous polypeptide sequence.

Another aspect of the invention provides a polypeptide comprising an amino acid sequence which has greater than 70% sequence identity with SEQ ID NO:2; SEQ ID NO:4; SEQ ID NO:6; SEQ ID NO:8, SEQ ID NO:10, SEQ ID NO:12, or SEQ ID NO:14; preferably, greater than 80%; more preferable, greater than 90%; more preferable greater than 95%; and in another embodiment, has 98 to 100% sequence identity with SEQ ID NO:2; SEQ ID NO:4; SEQ ID NO:6; SEQ ID NO:8, SEQ ID NO:10, SEQ DD NO:12, or SEQ ID NO:14. Some polypeptides of the invention specifically bind to polyclonal antibodies raised against and specifically binding two SEQ ID NO:2; SEQ ID NO:4; SEQ ID NO:6; SEQ ID NO:8, SEQ ID NO:10, SEQ ID NO:12, or SEQ ID NO:14.

The invention provides muteins comprising a hSMMyHC S1 domain comprising an amino acid sequence having an amino acid substitution, addition, and/or deletion as compared to a naturally-occurring hSMMyHC protein (e.g., a naturally-occurring hSMMyHC protein obtained from a non-pathological mammalian specimen). In a variation, the invention provides hSMMyHC fragments comprising a S1 or RLC binding domain (or fragments thereof), preferably S1, wherein said fragments comprise a naturally-occurring hSMMyHC amino acid sequence and exhibit binding to ATP and/or actin, or wherein such fragments comprise an amino acid substitution, addition, or deletion relative to the naturally-occurring hSMMyHC polypeptide sequence and which substantially lack binding to actin or ATP, and/or have activity as a hSMMyHC competitive antagonist and/or enhance actin-myosin contractile activity or block actin-myosin contractile activity of endogenous hSMMyHC protein.

Preferably, these amino acid sequences occur in the given order (in the amino-terminal to carboxy-terminal orientation) and may comprise other intervening and/or terminal sequences; generally such polypeptides are less than 1000 amino acids in length, more usually less than about 500 amino acids in lengths, and frequently approximately 849, 699, 772, 852, or 1979 amino acids in length.

The polypeptides of the present invention preferably will have a detectable biochemical property, including for example, ATPase function, the ability to bind actin, the ability to enhance actin-myosin contractile activity or the ability to block actin-myosin contractile activity of endogenous hSMMyHC protein.

The amino acid sequences of hSMMyHC polypeptides identified herein will enable those of skill in the art to produce polypeptides corresponding to hSMMyHC peptide sequences and sequence variants thereof. Such polypeptides may be produced in prokaryotic or eukaryotic host cells by expression of polynucleotides encoding a hSMMyHC peptide sequence (as described below), frequently as part of a larger polypeptide. Accordingly, the invention also provides host cells expressing hSMMyHC polypeptides encoded by a polynucleotide other than a naturally-occurring hSMMyHC gene or homolog gene of the host cell (if present). Such a polynucleotide may be an expression vector.

Alternatively, such peptides may be synthesized by chemical methods. Methods for expression of heterologous proteins in recombinant hosts, chemical synthesis of polypeptides, and in vitro translation are well known in the art and are described further in Maniatis et al., *Molecular Cloning: A Laboratory Manual* (1989), 2nd Ed., Cold Spring Harbor, N.Y.; Berger and Kimmel, *Methods in Enzymology, Volume 152. Guide to Molecular Cloning Techniques* (1987), Academic Press, Inc., San Diego, Calif.; Merrifield, J. (1969) *J. Am. Chem. Soc.* 91: 501; Chaiken I. M. (1981) *CRC Crit. Rev. Biochem.* 11: 255; Kaiser et al.(1989) *Science* 243: 187; Merrifield, B. (1986) *Science* 232: 342; Kent, S. B. H. (1988) *Ann. Rev. Biochem.* 57: 957; and Offord, R. E. (1980) *Semisynthetic Proteins*, Wiley Publishing).

Another embodiment involves the formation of hSMMyHC mutants wherein the native protein or fragment has at least one amino acid deleted or replaced by another amino acid and the mutants exhibits altered biological activity from the native protein or fragment. Moreover, in addition to hSMMyHC polypeptides consisting only of naturally-occurring amino acids, hSMMyHC peptidomimetics are also provided. For example, peptidomimetics can be suitable as drugs for inhibition of hSMMyHC function in contractility of smooth muscle tissues.

Peptide analogs are commonly used in the pharmaceutical industry as non-peptide drugs with properties analogous to those of the template peptide. These types of non-peptide compound are termed "peptide mimetics" or "peptidomimetics" (Fauchere, J. (1986) *Adv. Drug Res.* 15: 29; Veber and Freidinger (1985) *TINS* p.392; and Evans et al. (1987) *J. Med. Chem* 30: 1229) and are usually developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biological or pharmacological activity), such as human hSMMyHC, but have one or more peptide linkages optionally replaced by a linkage selected from the group consisting of: —$CH_2NH$—, —$CH_2S$—, —$CH_2$—$CH_2$—, —CH═CH— (cis and trans), —$COCH_2$—, —CH(OH)$CH_2$—, and —$CH_2SO$—, by methods known in the art and further described in the following references: Spatola, A. F. in "Chemistry and Biochemistry of Amino Acids, Peptides, and Proteins," B. Weinstein, eds., Marcel Dekker, New York, p. 267 (1983); Spatola, A. F., Vega Data (March 1983), Vol. 1, Issue 3, "Peptide Backbone Modifications" (general review); Morley, J. S., *Trends Pharm Sci* (1980) pp. 463-468 (general review); Hudson, D. et al., *Int J Pept Prot Res* (1979) 14:177-185 (—$CH_2NH$—, —$CH_2CH_2$—); Spatola, A. F. et al., *Life Sci* (1986) 38:1243-1249 (—$CH_2$—S); Hann, M. M., *J Chem Soc Perkin Trans I* (1982) 307-314 (—CH—CH—, cis and trans); Almquist, R. G. et al., *J Med Chem* (1980) 23:1392-1398 (—$COCH_2$—); Jennings-White, C. et al., *Tetrahedron Lett* (1982) 23:2533 (—$COCH_2$—); Szelke, M. et al., European Appln. EP 45665 (1982) CA: 97:39405 (1982) (—CH(OH)$CH_2$—); Holladay, M. W. et al., *Tetrahedron Lett* (1983) 24:4401-4404 (—C(OH)$CH_2$—); and Hruby, V. J., *Life Sci* (1982) 31:189-199 (—$CH_2$—S—). A particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macromolecules(s) to which the peptidomimetic binds to produce the therapeutic effect. Derivitization (e.g., labelling) of peptidomimetics should not substantially interfere with the desired biological or pharmacological activity of the peptidomimetic.

Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch (1992) *Ann. Rev. Biochem.* 61: 387); for example, by adding internal cysteine residues capable of forming intramolecular disulfide bridges which cyclize the peptide. Cyclic peptides comprising a sequence of BH1 and/or BH2 frequently are preferred.

Peptides and peptidomimetics can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal modifications such as amidation, as well as other terminal modifications, including cyclization, may be incorporated into various embodiments of the invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Such peptides or peptidomimetics may be used therapeutically to treat disease.

Production and Applications of Antibodies

Native hSMMyHC proteins, fragments thereof, or analogs thereof, may be used to immunize an animal for the production of specific antibodies. These antibodies may comprise a polyclonal antiserum or may comprise a monoclonal antibody produced by hybridoma cells. For general methods to prepare antibodies, see *Antibodies: A Laboratory Manual*, (1988) E. Harlow and D. Lane, Cold Spring Harbor Laboratory, Cold Spring Harbor, NY. For making human-specific antibodies, the resultant antibodies may be preadsorbed with non-primate SMMyHC species, which are typically immobilized on a support.

For example but not for limitation, a recombinantly produced fragment of hSMMyHC can be injected into a mouse along with an adjuvant following immunization protocols known to those of skill in the art so as to generate an immune response. Typically, approximately at least 1-50 μg of a hSMMyHC fragment or analog is used for the initial immunization, depending upon the length of the polypeptide. Alternatively or in combination with a recombinantly produced HSMMyHC polypeptide, a chemically synthesized peptide having a hSMMyHC sequence may be used as an immunogen to raise antibodies which bind a hSMMyHC protein, such as the native HSMMyHC polypeptide, a native human hSMMyHC polypeptide, a polypeptide comprising a hSMMyHC epitope, or a hSMMyHC fusion protein. Immunoglobulins which bind the recombinant fragment with a binding affinity of at least $1 \times 10^7$ M$^{-1}$ can be harvested from the immunized animal as an antiserum, and may be further purified by immunoaffinity chromatography or other means. Additionally, spleen cells are harvested from the immunized animal (typically rat or mouse) and fused to myeloma cells to produce a bank of antibody-secreting hybridoma cells. The bank of hybridomas can be screened for clones that secrete immunoglobulins which bind the recombinantly-produced hSMMyHC polypeptide (or chemically synthesized HSMMyHC polypeptide) with an affinity of at least $1 \times 10^6$ M$^{-1}$. Animals other than mice and rats may be used to raise antibodies; for example, goats, rabbits, sheep, and chickens may also be employed to raise antibodies reactive with a hSMMyHC protein. Transgenic mice having the capacity to produce human antibodies also may be immunized and used for a source of -hSMMyHC antiserum and/or for making monoclonal-secreting hybridomas (see, e.g., Lonberg et al., WO93/12227 (1993); Kucherlapati, WO 91/10741(1991)).

Bacteriophage antibody display libraries may also be screened for binding to a hSMMyHC polypeptide, such as a full-length hSMMyHC protein, a hSMMyHC fragment, or a fusion protein comprising a hSMMyHC polypeptide sequence comprising a hSMMyHC epitope (generally at least 5 contiguous amino acids). Generally such hSMMyHC peptides and the fusion protein portions consisting of hSMMyHC sequences for screening antibody libraries comprise about at least 3 to 5 contiguous amino acids of hSMMyHC, frequently at least 7 contiguous amino acids of hSMMyHC, usually comprise at least 10 contiguous amino acids of hSMMyHC, and most usually comprise a hSMMyHC sequence of at least 14 contiguous amino acids. Particularly preferred hSMMyHC epitopes are: -QGPSFAY-(SEQ ID NO:15) and -CTE-QGSHP-(SEQ ID NO:16).

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313). Typically, a bacteriophage antibody display library is screened with a hSMMyHC polypeptide that is immobilized (e.g., by covalent linkage to a chromatography resin to enrich for reactive phage by affinity chromatography) and/or labeled (e.g., to screen plaque or colony lifts).

HSMMyHC polypeptides which are useful as immunogens, for diagnostic detection of -hSMMyHC antibodies in a sample, for diagnostic detection and quantitation of hSMMyHC protein in a sample (e.g., by standardized competitive ELISA), or for screening a bacteriophage antibody display library, are suitably obtained in substantially pure form, that is, typically about 50 percent (w/w) or more purity, substantially free of interfering proteins and contaminants. Preferably, these polypeptides are isolated or synthesized in a purity of at least 80 percent (w/w) and, more preferably, in at least about 95 percent (w/w) purity, being substantially free of other proteins of humans, mice, or other contaminants.

For some applications of these antibodies, such as identifying immunocrossreactive proteins, the desired antiserum or monoclonal antibody(ies) is/are not monospecific. In these instances, it may be preferable to use a synthetic or recombinant fragment of HSMMyHC as an antigen rather than using the entire native protein. More specifically, where the object is to identify immunocrossreactive polypeptides that comprise a particular structural moiety, such as an actin-binding domain, it is preferable to use as an antigen a fragment corresponding to part or all of a commensurate structural domain in the hSMMyHC protein, often S1 domain.

If an antiserum is raised to a hSMMyHC fusion polypeptide, such as a fusion protein comprising a hSMMyHC immunogenic epitope fused to -galactosidase or glutathione S-transferase, the antiserum is preferably preadsorbed with the non-hSMMyHC fusion partner (e.g., -galactosidase or glutathione S-transferase) to deplete the antiserum of antibodies that react (i.e., specifically bind to) the non-hSMMyHC portion of the fusion protein that serves as the immunogen. Monoclonal or polyclonal antibodies which bind to the human and/or murine hSMMyHC protein can be used to detect the presence of human or murine hSMMyHC polypeptides in a sample, such as a Western blot of denatured protein (e.g., a nitrocellulose blot of an SDS-PAGE) obtained from a lymphocyte sample of a patient. Preferably quantitative detection is performed, such as by denistometric scanning and signal integration of a Western blot. The monoclonal or polyclonal antibodies will bind to the denatured HSMMyHC epitopes and may be identified visually or by other optical means with a labeled second antibody or labeled *Staphylococcus aureus* protein A by methods known in the art.

One use of such antibodies is to screen cDNA expression libraries, preferably containing cDNA derived from human or murine mRNA from various tissues, for identifying clones containing cDNA inserts which encode structurally-related, immunocrossreactive proteins, that are candidate novel HSMMyHC binding factors or hSMMyHC-related proteins. Such screening of cDNA expression libraries is well known in the art, and is further described in Young et al., *Proc. Natl. Acad. Sci. U.S.A.* 80:1194-1198 (1983)) as well as other published sources. Another use of such antibodies is to identify and/or purify immunocrossreactive proteins that are structurally or evolutionarily related to the native hSMMyHC protein or to the corresponding hSMMyHC fragment (e.g., functional domain, ATP-binding site, actin-binding site domain) used to generate the antibody. The anti-hSMMyHC antibodies of the invention can be used to measure levels of hSMMyHC protein in a cell or cell population, for example in a cell explant (e.g., lymphocyte sample) obtained from a patient.

Various other uses of such antibodies include therapeutic applications (e.g., as cationized antibodies or by targeted liposomal delivery) to treat hypertension, hypotension, heart disease, asthma, and the like.

An antiserum which can be utilized for this purpose can be obtained by conventional procedures. One exemplary procedure involves the immunization of a mammal, such as rabbits, which induces the formation of polyclonal antibodies against hSMMyHC. Monoclonal antibodies are also being generated from already immunized hamsters. This antibody can be used to detect the presence and level of the hSMMyHC protein.

It is also possible to use the proteins for the immunological detection of hSMMyHC and associations thereof with standard assays as well as assays using markers, which are radio-immunoassays or enzyme immunoassays.

The detection and determination of hSMMyHC has significant diagnostic importance. Thus these proteins and their antibodies can be employed as a marker to monitor, check or detect the course of disease.

Identification and Isolation of Proteins That Bind hSM-MyHC

Proteins that bind to hSMMyHC are potentially important regulatory proteins. Such proteins may be targets for novel antihypertensive agents or anti-inflammatory agents, immunomodulatory agents, asthma medicaments, and the like. These proteins are referred to herein as accessory proteins. Accessory proteins may be isolated by various methods known in the art.

Polypeptide Compositions

The present invention also provides compositions comprising recombinant and/or substantially purified hSMMyHC proteins. Such compositions typically comprise an aqueous buffer, a hSMMyHC protein which is present at a concentration of at least 1 pM in substantially purified form free of primate proteins other than myosin, actin, troponin, tropomyosin, caldesmon, calmodulin, and calponin, which may themselves be either present or absent in the composition. In an aspect, the composition further comprises ATP and optionally also comprises actin and/or myosin light chains; the optional actin and/or myosin light chain(s) may themselves be substantially purified and/or recombinant and are typically primate, preferably human, in origin.

B. Polynucleotides

In one aspect, the polynucleotides provided herein are defined by the proteins encoded thereby. A preferred embodiment of the invention is drawn to a polynucleotide encoding a hSMMyHC polypeptide, wherein the polypeptide has the following properties: (i) the polypeptide's activity includes ATPase function or the ability to bind actin; and (ii) the polypeptide has an amino acid sequence which has greater than 70% sequence identity with SEQ ID NO:2; SEQ ID NO:4; SEQ ID NO:6; SEQ ID NO:8, SEQ ID NO:10, SEQ ID NO:12, or SEQ ID NO:14; or a substantially identical mutein, fragment, homolog, analog, or fusion protein thereof; preferably, greater than 80%; more preferable, greater than 90%; more preferable greater than 95%; and in another embodiment, has 98 to 100% sequence identity with SEQ ID NO:2; SEQ ID NO:4; SEQ ID NO:6; SEQ ID NO:8, SEQ ID NO:10, SEQ ID NO:12, or SEQ ID NO:14; or a substantially identical mutein, fragment, analog, or fusion protein thereof.

In one embodiment, the polynucleotide encodes a hSMMyHC polypeptide having an amino acid sequence of SEQ ID NO:2; SEQ ID NO:4; SEQ ID NO:6; SEQ ID NO:8, SEQ ID NO:10, SEQ ID NO:12, or SEQ ID NO:14; or a substantially identical mutein, homolog, fragment, analog, or fusion protein thereof.

In one embodiment, the polynucleotide comprises a sequence which is greater than 55 or 60% sequence identity with SEQ ID NO:2; SEQ ID NO:4; SEQ ID NO:6; SEQ ID NO:8, SEQ ID NO:10, SEQ ID NO:12, or SEQ ID NO:14; preferably, greater than 70%; more preferably, greater than 80%; more preferably, greater than 90 or 95%; or, in another embodiment, has 98 or 100% sequence identity with SEQ ID NO:2; SEQ ID NO:4; SEQ ID NO:6; SEQ ID NO:8, SEQ ID NO:10, SEQ ID NO:12, or SEQ ID NO:14.

In another embodiment provided herein, the polynucleotide hybridizes under stringent conditions to a polynucleotide having a sequence or complementary sequence of SEQ ID NO:1, SEQ ID NO:3, SEQ ID NO:5, SEQ ID NO:7, SEQ ID NO:9, SEQ ID NO:11, or SEQ ID NO:13. The invention also includes polynucleotides that result from PCR amplification using a pair of upstream and downstream primers designed to have the sequence of or be complementary to a terminal segment of at least 20 nucleotides of a polynucleotide selected from SEQ ID NO:2; SEQ ID NO:4; SEQ ID NO:6; SEQ ID NO:8, SEQ ID NO:10, SEQ ID NO:12, or SEQ ID NO:14.

In another embodiment, the polynucleotide has the sequence of SEQ ID NO:1, SEQ ID NO:3, SEQ ID NO:5, SEQ ID NO:7, SEQ ID NO:9, SEQ ID NO:11, or SEQ ID NO:13.

As described further herein, when describing the polynucleotide in terms of SEQ ID NO:1, SEQ ID NO:3, SEQ DD NO:5, SEQ ID NO:7, SEQ ID NO:9, SEQ ID NO:11, or SEQ ID NO:13, the sequence identity may be slightly lower due to the degeneracy in the genetic code. The degeneracy of the genetic code gives a finite set of polynucleotide sequences encoding these amino acid sequences; this set of degenerate sequences may be readily generated by hand or by computer using commercially available software (Wisconsin Genetics Software Package Release 7.0).

Isolated hSMMyHC polynucleotides typically are less than approximately 10,000 nucleotides in length. HSM-MyHC polynucleotides may be short oligonucleotides (e.g., 20-100 bases long), such as for use as hybridization probes and PCR (or LCR) primers. HSMMyHC polynucleotide sequences may also comprise part of a larger polynucleotide (e.g., a cloning vector comprising a HSMMyHC clone) and may be fused, by polynucleotide linkage, in frame with another polynucleotide sequence encoding a different protein (e.g., glutathione S-transferase or -galactosidase) for encoding expression of a fusion protein. Typically, hSMMyHC polynucleotides comprise at least 25 consecutive nucleotides which are substantially identical to a naturally-occurring hSMMyHC sequence, more usually hSMMyHC polynucleotides comprise at least 50 to 100 consecutive nucleotides which are substantially identical to a naturally-occurring hSMMyHC sequence. However, it will be recognized by those of skill that the minimum length of a hSMMyHC polynucleotide required for specific hybridization to a hSM-MyHC target sequence will depend on several factors: G/C content, positioning of mismatched bases (if any), degree of uniqueness of the sequence as compared to the population of target polynucleotides, and chemical nature of the polynucleotide (e.g., methylphosphonate backbone, polyamide nucleic acid, phosphorothiolate, etc.), among others.

The human SMMyHC gene has 43 exons of which are 2 exons (6 and 42) whose expression is variable and controllable by alternative splicing. Forms lacking exon 6, encoding 7 amino acids in the N-terminus, are largely found in the vasculature, forms containing exon 6 are visceral. Forms lacking exon 42 (SM 1) are absent in fetal tissues; forms containing exon 42 (SM2) are more constitutively expressed. The sequence of all 4 possible splice variants are found in the Drawings.

The following numbering convention is employed herein:

| exon | pos in cDNA |
|------|-------------|
| 1 | 1 to: 58 |
| 2 | 59 to: 420 |
| 3 | 421 to: 577 |
| 4 | 578 to: 605 |
| 5 | 606 to: 708 |
| 6 | 709 to: 729 |
| 7 | 730 to: 822 |
| 8 | 823 to: 886 |
| 9 | 887 to: 985 |
| 10 | 986 to: 1129 |
| 11 | 1130 to: 1225 |
| 12 | 1226 to: 1344 |
| 13 | 1345 to: 1497 |
| 14 | 1498 to: 1671 |
| 15 | 1672 to: 1845 |
| 16 | 1846 to: 1960 |
| 17 | 1961 to: 2154 |
| 18 | 2155 to: 2276 |
| 19 | 2277 to: 2346 |
| 20 | 2347 to: 2507 |
| 21 | 2508 to: 2616 |
| 22 | 2617 to: 2748 |
| 23 | 2749 to: 2955 |
| 24 | 2956 to: 3093 |
| 25 | 3094 to: 3217 |
| 26 | 3218 to: 3389 |
| 27 | 3390 to: 3602 |
| 28 | 3603 to: 3747 |
| 29 | 3748 to: 3954 |
| 30 | 3955 to: 4059 |
| 31 | 4060 to: 4212 |
| 32 | 4213 to: 4461 |
| 33 | 4462 to: 4674 |
| 34 | 4675 to: 4887 |
| 35 | 4888 to: 5049 |
| 36 | 5050 to: 5178 |
| 37 | 5179 to: 5267 |
| 38 | 5268 to: 5391 |
| 39 | 5392 to: 5600 |
| 40 | 5601 to: 5709 |
| 41 | 5710 to: 5882 |
| 42 | 5883 to: 5921 |
| 43 | 5922 to: 6908 |

The invention also provides a polynucleotide (e.g., a DNA isolate) consisting essentially of a genomic DNA sequence encoding hSMMyHC and more particularly a composition consisting of cDNA molecules which encode the hSMMyHC protein.

Synthetic polynucleotide sequences may be constructed by chemical synthesis of oligonucleotides.

It is apparent to one of skill in the art that nucleotide substitutions, deletions, and additions may be incorporated into the polynucleotides of the invention. Nucleotide sequence variation may result from sequence polymorphisms of various hSMMyHC alleles, minor sequencing errors, and the like. However, such nucleotide substitutions, deletions, and additions should not substantially disrupt the ability of the polynucleotide to hybridize to one of the polynucleotide sequences SEQ ID NO:1, SEQ ID NO:3, SEQ ID NO:5, SEQ ID NO:7, SEQ ID NO:9, SEQ ID NO:11, or SEQ ID NO:13 under hybridization conditions that are sufficiently stringent to result in specific hybridization.

Polynucleotides encoding full-length hSMMyHC or fragments or analogs thereof, may include sequences that facilitate transcription (expression sequences) and translation of the coding sequences, such that the encoded polypeptide product is produced. Construction of such polynucleotides is well known in the art and is described further in Maniatis et al., *Molecular Cloning: A Laboratory Manual,* 2nd Ed. (1989), Cold Spring Harbor, N.Y. For example, but not for limitation, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector. A typical eukaryotic expression cassette will include a polynucleotide sequence encoding a hSMMyHC polypeptide linked downstream (i.e., in translational reading frame orientation; polynucleotide linkage) of a promoter such as the HSV tk promoter or the pgk (phosphoglycerate kinase) promoter, optionally linked to an enhancer and a downstream polyadenylation site (e.g., an SV40 large T Ag poly A addition site).

A variety of expression vector/host systems may be utilized to contain and express sequences encoding hSMMyHC. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORTI plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g. viral promoters or leader sequences) may be cloned into the vector. In mammalian cell systems, promoters from mammalian genes or from mammalian viruses are preferable. If it is necessary to generate a cell line that contains multiple copies of the sequence encoding hSMMyHC, vectors based on SV40 or EBV may be used with an appropriate selectable marker.

In bacterial systems, a number of expression vectors may be selected depending upon the use intended for hSMMyHC. For example, when large quantities of hSMMyHC are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding hSMMyHC may be ligated into the vector in frame with sequences for the amino-terminal Met and the subsequent 7 residues of.beta.-galactosidase so that a hybrid protein is produced; pIN vectors (Van Heeke, G. and S. M. Schuster (1989) J. Biol. Chem. 264:5503-5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will. In the yeast, *Saccharomyces cerevisiae*, a number of vectors containing constitutive or inducible promoters such as alpha factor, alcohol oxidase, and PGH may be used. For reviews, see Ausubel et al., (supra) and Grant et al. (1987) Methods Enzymol. 153:516-544.

In cases where plant expression vectors are used, the expression of sequences encoding hSMMyHC may be driven by any of a number of promoters. For example, viral promoters such as the 35S and 19S promoters of CaMV may be used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews (see, for example, Hobbs, S., or Murry, L. E. in McGraw Hill Yearbook of Science and Technology(1992) McGraw Hill, New York, N.Y.; pp. 191-196.

An insect system may also be used to express hSMMyHC. For example, in one such system, Autographa californica nuclear polyhedrosis virus (AcNPV) is used as a vector to express foreign genes in Spodoptera frugiperda cells or in Trichoplusia larvae. The sequences encoding hSMMyHC may be cloned into a non-essential region of the virus, such as the polyhedrin gene, and placed under control of the polyhedrin promoter. Successful insertion of hSMMyHC will render the polyhedrin gene inactive and produce recombinant virus lacking coat protein. The recombinant viruses may then be used to infect, for example, *S. frugiperda* cells or *Trichoplusia larvae* in which hSMMyHC may be expressed (Engelhard, E. K. et al. (1994) Proc. Nat. Acad. Sci. 91:3224-3227).

In mammalian host cells, a number of viral-based expression systems may be utilized. In cases where an adenovirus is used as an expression vector, sequences encoding hSM-MyHC may be ligated into an adenovirus transcription/translation complex consisting of the late promoter and tripartite leader sequence. Insertion in a non-essential E1 and E3 region of the viral genome may be used to obtain a viable virus which is capable of expressing hSMMyHC in infected host cells (Logan, J. and Shenk, T. (1984) Proc. Natl. Acad. Sci. 81:3655-14 3659). In addition, transcription enhancers, such as the Rous sarcoma virus (RSV) enhancer, may be used to increase expression in mammalian host cells. Human artificial chromosomes (HACs) may also be employed to deliver larger fragments of DNA than can be contained and expressed in a plasmid. HACs of 6 to 10 M are constructed and delivered via conventional delivery methods (liposomes, polycationic amino polymers, or vesicles) for therapeutic purposes.

Specific initiation signals may also be used to achieve more efficient translation of sequences encoding hSMMyHC. Such signals include the ATG initiation codon and adjacent sequences. In cases where sequences encoding hSMMyHC, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125-162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities, (e.g. CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express hSMMyHC may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223-32) and adenine phosphoribosyltransferase (Lowry, I. et al. (1980) Cell 22:817-23) genes which can be employed in tk.sup.- or aprt.sup.-cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567-70); npt, which confers resistance to the aminoglycosides, neomycin and G-418 (Colbere-Garapin, F. et al (1981) J. Mol. Biol. 150:1-14); and als or pat, which confer resistance to chlorsulfuron and phosphinotricin acetyltransferase, respectively (Murry, supra). Additional selectable genes have been described, for example, trpB, which allows cells-to utilize indole in place of tryptophan, or hisD, which allows cells to utilize histinol in place of histidine (Hartman, S. C. and R. C. Mulligan (1988) Proc. Natl. Acad. Sci. 85:8047-51). Recently, the use of visible markers has gained popularity with such markers as anthocyanins, .beta. glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121-131).

Although the presence/absence of marker gene expression suggests that the gene of interest is also present, its presence and expression may need to be confirmed. For example, if the sequence encoding hSMMyHC is inserted within a marker gene sequence, transformed cells containing sequences encoding hSMMyHC can be identified by the absence of marker gene function. Alternatively, a marker gene can be placed in tandem with a sequence encoding hSMMyHC under the control of a single promoter. Expression of the marker gene in response to induction or selection usually indicates expression of the tandem gene as well.

Additionally, where expression of a polypeptide is not desired, polynucleotides of this invention need not encode a functional protein. Polynucleotides of this invention may serve as hybridization probes and/or PCR primers (amplimers) and/or LCR oligomers for detecting hSMMyHC RNA or DNA sequences.

Polynucleotides comprising sequences of approximately 15-50 nucleotides, preferably about 18-25 nucleotides, corresponding to or complementary to SEQ ID NO:1, SEQ ID NO:3, SEQ ID NO:5, SEQ ID NO:7, SEQ ID NO:9, SEQ ID NO:11, or SEQ ID NO:13 can serve as PCR primers and/or hybridization probes for identifying and isolating germline genes corresponding to hSMMyHC. These germline genes may be human or may be from a related mammalian species, preferably rodents or primates. Such germline genes may be isolated by various methods conventional in the art, including, but not limited to, by hybridization screening of genomic libraries in bacteriophage or cosmid libraries, or by PCR amplification of genomic sequences using primers derived from SEQ ID NO:1, SEQ ID NO:3, SEQ ID NO:5, SEQ ID NO:7, SEQ ID NO:9, SEQ ID NO:11, or SEQ ID NO:13. Human genomic libraries are publicly available or may be constructed de novo from human DNA.

For such hybridization and PCR applications, the polynucleotides of the invention need not encode a functional polypeptide. Thus, polynucleotides of the invention may contain substantial deletions, additions, nucleotide substitutions and/or transpositions, so long as specific hybridization or specific amplification to a hSMMyHC sequence is retained.

More specifically, genomic or cDNA clones encoding hSMMyHC may be isolated from clone lines (e.g., available from Clontech, Palo Alto, Calif.) using hybridization probes designed on the basis of SEQ ID NO:1, SEQ ID NO:3, SEQ ID NO:5, SEQ ID NO:7, SEQ ID NO:9, SEQ ID NO:11, or SEQ ID NO:13 using conventional hybridization screening methods (e.g., Benton W D and Davis R W (1977) *Science* 196: 180; Goodspeed et al. (1989) *Gene* 76: 1). Where a cDNA clone is desired, clone libraries containing cDNA derived from somatic cell mRNA or other hSMMyHC-expressing cell mRNA are preferred.

For illustration and not for limitation, SEQ ID NO:1, SEQ ID NO:3, SEQ ID NO:5, SEQ ID NO:7, SEQ ID NO:9, SEQ ID NO:11, or SEQ ID NO:13 may be labeled and used as a hybridization probe to isolate genomic clones from a human or murine genomic clone library in EMBL4 or GEM11 (Promega Corporation, Madison, Wis.).

Suitable hybridization conditions for specific hybridization of these labeled probes to the human hSMMyHC cDNA or gene can be established empirically by performing a series of hybridizations and/or washing steps at several temperatures and/or ionic strength conditions; for example and not limitation, hybridization conditions comprising 50% formamide, 5×SSC or SSPE, 1-5× Denhardt's solution, 0.1-1% SDS, 100-200 µg sheared heterologous DNA or tRNA, 0-10% dextran sulfate, $1 \times 10^5$ to $1 \times 10^7$ cpm/ml of denatured probe with a specific activity of about $1 \times 10^8$ cpm/µg, and incubation at 42 C-37 C for about 6-36 hours is often a suitable initial point. Prehybridization conditions are essentially identical-except that probe is not included and incubation time is typically reduced. Washing conditions are typically 1-3×SSC, 0.1-1% SDS, 50-70 C with change of wash solution at about 5-30 minutes. For isolating human hSMMyHC polynucleotides with a hSMMyHC polynucleotide probe, it is often preferred to hybridize at approximately 39 C and to wash sequentially at the following step temperatures: room temperature, 37 C, 39 C, 42 C, 45 C, 50 C, 55 C, 60 C, 65 C, and 70 C, stopping after each step and monitoring the background probe signal (and optionally detecting signal by autoradiogram and/or phosphor imaging, if radiolabeled probe is used) and terminating the washing steps when suitable signal/noise ratio is achieved, as determined empirically.

Human and other primate hSMMyHC DNAs and genomic clones (i.e., cognate human and nonhuman genes) can be analogously isolated from various human or nonhuman cDNA and genomic clone libraries available in the art (e.g., Clontech, Palo Alto, Calif.) by using probes based on the sequences shown in the Drawings, with hybridization and washing conditions as known in the art.

Additionally, polymerase chain reaction (PCR) using primers based on SEQ ID NO:1, SEQ ID NO:3, SEQ ID NO:5, SEQ ID NO:7, SEQ ID NO:9, SEQ ID NO:11, or SEQ ID NO:13 may be used to amplify DNA fragments from genomic DNA, mRNA pools, or from cDNA clone libraries. U.S. Pat. Nos. 4,683,195 and 4,683,202 describe the PCR method. Additionally, PCR methods employing one primer that is based on the sequence data disclosed in FIG. 1 and a second primer that is not based on that sequence data may be used. For example, a second primer that is homologous to or complementary to a polyadenylation segment may be used.

Provided in the invention are polynucleotides comprising a segment encoding a hSMMyHC epitope or a multiplicity of hSMMyHC epitopes. A particularly preferred polynucleotide encoding a hSMMyHC epitope of the invention comprises the sequence -CAAGGCCCATCTTTTGCCTAC-(SEQ ID NO:17).

Polynucleotides encoding epitopes having substantial identity to these preferred epitopes are often employed. Such polynucleotides have a variety of uses, including as hSMMyHC probes, as templates for producing polypeptides comprising a hSMMyHC epitope whereby such proteins are hSMMyHC immunogens or commercial diagnostic reagents for standardizing a hSMMyHC immunoassay, as polynucleotide vaccines (immunogens) when fused to a secretory sequence for administering to an animal and making -hSMMyHC antisera and hybridomas.

In one aspect, the invention provides a hSMMyHC polynucleotide (e.g., as a primer or probe) affixed to a solid substrate, typically wherein the solid substrate has a plurality of polynucleotide species affixed thereto, in a spatially defined array whereby each cell typically contains a single polynucleotide species, with the array often comprising in excess of 1000 distinct polynucleotide species. The hSMMyHC polynucleotide is typically affixed by covalent linkage to the solid substrate. The solid substrate constitutes an array of polynucleotide probes and/or primers, aherein at least one member of the array is a hSMMyHC polynucleotide. Generally, the solid substrate will be less than 10 cm$^3$ and comprise at least 1024 positionally distinct polynucleotide species, at least one of which is a hSMMyHC polynucleotide. Such polynucleotides arrays on solid substrates (e.g., a polysilicon wafer) can be used for genotype determination, disease detection and diagnosis, therapeutic efficacy monitoring, or for sequencing (e.g., of a pool containing unknown polynucleotides; for sequencing a mammalian genome or cDNA library), or other like uses.

The invention provides a diagnostic kit for detecting a pathological condition, such as cancer, wherein the kit contains at least one hSMMyHC polynucleotide.

The invention provides a gene therapy method and compositions therefore, comprising a hSMMyHC polynucleotide, which can often be operably linked to polynucleotide sequences to drive expression (e.g., promoter, enhancer, etc.) or other components of a gene therapy vector or homologous recombination construct, according to method and materials known in the art. One variation comprises a hSMMyHC polynucleotide in a viral vector for gene therapy. A variation employs a hSMMyHC polynucleotide in a gene therapy delivery formulation (e.g., comprising cationic or neutral lipids, polylysine, polyarginine, or other delivery-enhancing vehicle); the hSMMyHC polynucleotide may be formulated with other polynucleotides for therapeutic benefit.

The invention also provides the use of a hSMMyHC polynucleotide to diagnose and/or treat disease, or to identify an individual based, in part, on their hSMMyHC genotype as defined by a allele-specific restriction site pattern or nucleotide sequence, or abundance of hSMMyHC mRNA transcripts or RNA splicing pattern variation.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H A Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; *PCR*, eds. McPherson, Quirkes, and Taylor, IRL Press, Oxford; and U.S. Pat. No. 4,683,202).

Automated Sequencing System

The invention, which includes disclosure of a hSMMyHC cDNA sequence, provides for the sequencing of a hSMMyHC polynucleotide, such as sequencing in an automated sequencing apparatus; such sequencing may comprise determination of sequences of other cDNA or gene sequences, such as from sequencing a pool of polynucleotide species, and usually comprises determination of the sequence(s) of the polynucleotide species, including hSMMyHC, if present, and generally involves analysis of the hSMMyHC sequence(s) and/or their abundance in the polynucleotide pool. The present invention allows the identification of hSMMyHC polynucleotide sequences in such automated sequencing methods, including sequence variants of hSMMyHC and naturally-occurring and/or pathological hSMMyHC alleles and sequences thereof.

C. Assays

Binding Assays

The polypeptides described herein, as well as fragments or analogs thereof can be used as reagents in binding assays to detect binding to actin, myosin light chain(s) and/or ATP for identifying agents that interfere with hSMMyHC function, said agents are thereby identified as candidate drugs which may be used, for example, to block contractility in asthma or hypertension. Thus, the invention provides screening assays for identifying agents which modulate (e.g., inhibit) binding of a hSMMyHC polypeptide to a human actin polypeptide and/or which modulate (e.g., inhibit) binding of a hSMMyHC polypeptide to ATP or to modulate ATP hydrolysis.

Typically, in vitro binding assays that measure binding of hSMMyHC employ native hSMMyHC that contains S1 domain or a fragment thereof. The hSMMyHC polypeptide may be linked to a solid substrate by any of various means known to those of skill in the art; such linkage may be non-covalent (e.g., binding to a highly charged surface such as Nylon 66) or may be by covalent bonding (e.g., typically by chemical linkage). HSMMyHC polypeptides can be labeled by incorporation of a radiolabeled amino acid or fluorescent label. The labeled hSMMyHC polypeptide is contacted with the immobilized actin, myosin light chain(s) under aqueous conditions that permit specific binding in control binding reactions with a binding affinity of about $1 \times 10^5$ $M^{-1}$ or greater (e.g., 10-250 mM NaCl or KCl and 5-100 mM Tris HCl pH 5-9, usually pH 6-8), generally including $Zn^{+2}$ and/or $Mn^{+2}$ and/or $Mg^{+2}$ in the nanomolar to micromolar range (1 nM to 999 µM). Specificity of binding is typically established by adding unlabeled competitor at various concentrations selected at the discretion of the practitioner. Examples of unlabeled protein competitors include, but are not limited to, the following: unlabeled hSMMyHC polypeptide, bovine serum albumin, and cellular protein extracts. Binding reactions wherein one or more agents are added are performed in parallel with a control binding reaction that does not include an agent. Agents which inhibit the specific binding of hSMMyHC polypeptides as compared to a control reaction, are identified as candidate hSMMyHC-modulating drugs.

Thus, the invention also provides assay compositions comprising a hSMMyHC protein or variant thereof and a candidate agent which may bind to the hSMMyHC protein. In an aspect, the assay composition will further include an indicator composition, ATP, actin, myosin light chain(s), troponin, tropomyosin, caldesmon, calmodulin, and/or calponin, and the like, preferably of primate origin, typically of human origin.

Functional Assays

Candidate agents can be screened to identify those capable of modulating the activity of the target protein. Such an assay can comprise the steps of combining the candidate agent with the target protein, as above, and determining an alteration in the biological activity of the target protein. Thus, in this embodiment, the candidate agent may both bind to the target protein or fragment thereof (although this may not be necessary), and alter its biological or biochemical activity as defined herein. The methods include both in vitro screening methods and in vivo screening of cells for alterations in cell cycle distribution, cell viability, or for the presence, morphology, activity, distribution, or amount of mitotic spindles, as are generally outlined above.

According to one embodiment, the invention provides a method for identifying a candidate agent that modulates a detectable biochemical function of hSMMyHC in vitro. The method comprises measuring said detectable function in a first assay mixture comprising hSMMyHC and a candidate agent to obtain a function measurement and comparing said function measurement to a second assay mixture substantially identical to said first assay mixture but lacking said candidate agent and optionally including a second candidate agent, and determining whether the function measurements significantly differ by statistical measurement and identifying a candidate agent producing a statistically significant difference as a candidate drug.

In a preferred embodiment, activity is measured by the methods disclosed in Ser. No. 09/314,464, filed May 18, 1999, entitled "Compositions and assay utilizing ADP or phosphate for detecting protein modulators", which is incorporated herein by reference in its entirety. More specifically, this assay detects modulators of any aspect of a motor function ranging from interaction with actin to hydrolysis of ATP. ADP or phosphate is used as the readout for protein activity.

There are a number of enzymatic assays known in the art which use ADP as a substrate. For example, kinase reactions such as pyruvate kinases are known. See, Nature 78:632 (1956) and Mol. Pharmacol. 6:31 (1970). This is a preferred method in that it allows the regeneration of ATP. In one embodiment, the level of activity of the enzymatic reaction is determined directly. In a preferred embodiment, the level of activity of the enzymatic reaction which uses ADP as a substrate is measured indirectly by being coupled to another reaction. For example, in one embodiment, the method further comprises a lactate dehydrogenase reaction under conditions which normally allow the oxidation of NADH, wherein said lactate dehydrogenase reaction is dependent on the pyruvate kinase reaction. Measurement of enzymatic reactions by coupling is known in the art. Furthermore, there are a number of reactions which utilize phosphate. Examples of such reactions include a purine nucleoside phosphorylase reaction. This reaction can be measured directly or indirectly. A particularly preferred embodiments utilizes the pyruvate kinase/lactate dehydrogenase system.

In one embodiment, the detection of the ADP or phosphate proceeds non-enzymatically, for example, by binding or reacting the ADP or phosphate with a detectable compound. For example, phosphomolybdate based assays may be used which involve conversion of free phosphate to a phosphomolybdate complex. One method of quantifying the phosphomolybdate is with malachite green. Alternatively, a fluorescently labeled form of a phosphate binding protein, such as the E. coli phosphate binding protein, can be used to measure phosphate by a shift in its fluorescence.

In addition, target protein activity can be examined by determining modulation of target protein in vitro using cultured cells. The cells are treated with a candidate agent and the effect of such agent on the cells is then determined either directly or by examining relevant surrogate markers. For example, characteristics such as mitotic spindle morphology and cell cycle distribution can be used to determine the effect.

Thus, in a preferred embodiment, the methods comprise combining a target protein and a candidate agent, and determining the effect of the candidate agent on the target protein. Generally a plurality of assay mixtures are run in parallel with different agent concentrations to obtain a differential response to the various concentrations. Typically, one of these concentrations serves as a negative control, i.e., at zero concentration or below the level of detection.

As will be appreciated by those in the art, the components may be added in buffers and reagents to assay target protein activity and give optimal signals. Since the methods allow kinetic measurements, the incubation periods can be optimized to give adequate detection signals over the background.

In a preferred embodiment, an antifoam or a surfactant is included in the assay mixture. Suitable antifoams include, but are not limited to, antifoam 289 (Sigma). Suitable surfactants include, but are not limited to, Tween, Tritons, including Triton X-100, saponins, and polyoxyethylene ethers. Generally, the antifoams, detergents, or surfactants are added at a range from about 0.01 ppm to about 10 ppm. A preferred assay design is also provided. In one aspect, the invention provides a multi-time-point (kinetic) assay, with at least two data points being preferred. In the case of multiple measurements, the absolute rate of the protein activity can be determined.

The invention provides assay compositions comprising a hSMMyHC protein or variant thereof and a candidate agent which may modulate function of the hSMMyHC protein. In an aspect, the assay composition will further include ATP, actin, myosin light chain(s), troponin, tropomyosin, caldesmon, calmodulin, and calponin, and the like, preferably of primate origin, typically of human origin.

Rational Drug Design

HSMMyHC polypeptides, especially those portions which form direct contacts with actin, can be used for rational drug design of candidate hSMMyHC-modulating agents. The substantially purified hSMMyHC and the identification of actin as a docking partner for hSMMyHC as provided herein permits production of substantially pure hSMMyHC/actin polypeptide complexes and substantially pure hSMMyHC/ATP polypeptide complexes. The disclosed sequences and protein sources provide data for computational models which can be used for protein X-ray crystallography or other structure analysis methods, such as the DOCK program (Kuntz et al (1982) *J. Mol. Biol.* 161: 269; Kuntz I D (1992) *Science* 257: 1078) and variants thereof. Potential therapeutic drugs may be designed rationally on the basis of structural information thus provided. In one embodimnent, such drugs are designed to prevent formation of a hSMMyHC:actin complex and/or to prevent formation of a hSMMyHC:ATP complex. Thus, the present invention may be used to design drugs, including drugs with a capacity to modulate the interaction of hSMMyHC with actin or ATP.

Diagnostics

The polynucleotides of the invention can be employed for diagnosis of pathological conditions or genetic disease that involve medical conditions related to hSMMyHC function, and more specifically conditions and diseases that involve alterations in the structure or abundance of a hSMMyHC polypeptide. For example, they can be employed as probes useful for the diagnosis of pathological conditions or genetic disease that involve asthma, hypertension, hypotension, pregnancy, pre-term labor, menstrual cramps, glaucoma, urinary incontinence, irritable bowel syndrome, bronchioconstriction, cardiac malfunction or other medical conditions related to hSMMyHC function.

More specifically, the polynucleotides can be used for diagnosis of disease states (e.g., smooth muscle dysfunction or atrophy) by detection of a hSMMyHC mRNA or rearrangements or amplification of the hSMMyHC gene in cells explanted from a patient, or detection of a pathogenomonic hSMMyHC allele (e.g., by RFLP or allele-specific PCR analysis). Typically, the detection will be by in situ hybridization using a labeled (e.g., $^{32}P$, $^{35}S$, $^{14}C$, $^{3}H$, fluorescent, biotinylated, digoxigeninylated) hSMMyHC polynucleotide, although Northern blotting, dot blotting, or solution hybridization on bulk RNA or poly $A^+$ RNA isolated from a cell sample may be used, as may PCR amplification using hSM-MyHC-specific primers. The detection of pathogenomonic rearrangements, deletion, or amplification of the hSMMyHC gene locus or closely linked loci in a cell sample will identify the presence of a pathological condition or a predisposition to developing a pathological condition (e.g., genetic disease).

The polynucleotides of the invention can be to perform tissue typing (i.e., identify tissues characterized by the expression of hSMMyHC mRNA or differential expression of splicing isoforms thereof), and the like. The sequences may also be used for detecting genomic hSMMyHC gene sequences in a DNA sample, (e.g., by RFLP analysis, PCR product length(s) distribution, etc.).

The present invention also provides a method for diagnosing a disease in a human patient, wherein a diagnostic assay (e.g., immunohistochemical staining of fixed cells by an antibody that specifically binds hSMMyHC polypeptides) is used to determine if a predetermined pathogenomonic concentration of hSMMyHC polypeptide or its encoding mRNA is present in a biological sample from a human patient; if the assay indicates the presence of hSMMyHC polypeptide or its encoding mRNA outside of the normal range (e.g., outside the predetermined pathogenomonic concentration range), the patient is diagnosed as having a disease condition or predisposition.

Thus, antibodies which bind to hSMMyHC can be used as diagnostic reagents to identify cells exhibiting altered hSM-MyHC function in a cellular sample from a patient (e.g., a smooth muscle tissue sample, a solid tissue biopsy), as commercial reagents to identify, isolate, and/or quantitate hSM-MyHC polypeptides in samples and histological specimens, and the like. Frequently, anti-hSMMyHC antibodies are included as diagnostic reagents for immunohistopathology staining of cellular samples in situ. Additionally, anti-hSM-MyHC antibodies may be used therapeutically by targeted delivery to cells (e.g., by cationization or by liposome or immunoliposome delivery).

The invention also involves the use of the protein hSM-MyHC or mutein or fragment thereof for performing immunochemical methods for the detection and determination of the protein or its associated proteins, in order to monitor cell contractility, differentiation, or motile function, or to detect or monitor the course of diseases.

Therapeutics

Another aspect of the invention pertains to a method of treating a subject having a state characterized by smooth muscle contraction. The method involves administering to a subject a therapeutically effective amount of a modulating agent, e.g., a hSMMyHC agonist or antagonist, such that treatment of the state characterized by smooth muscle contraction occurs. In one embodiment, the state is characterized by the contraction of smooth muscle having a high basal tone. In another embodiment, the state characterized by the contraction of smooth muscle involves a state characterized by abnormal or inappropriate contraction of smooth muscle. In yet another embodiment, the state characterized by the contraction of smooth muscle involves abnormal or inappropriate relaxation of smooth muscle. In yet another embodiment, the treatment of the state involves the reduction or inhibition of inappropriate smooth muscle contraction. Examples of states include asthma, hypertension, hypotension, pregnancy, preterm labor, menstrual cramps, glaucoma, urinary incontinence, irritable bowel syndrome, bronchioconstriction, cardiac malfunction or other medical conditions related to hSMMyHC function.

"Therapeutically effective amount" includes an amount effective, at dosages and for periods of time necessary, to achieve the desired level of smooth or cardiac muscle contraction. A therapeutically effective amount of a modulating agent, e.g., a hSMMyHC agonist or antagonist, may vary according to factors such as the disease state, age, and weight of the individual, and the ability of the modulating agent to elicit a desired level of muscle contraction or calcium sensitivity in the subject. Dosage regimens may be adjusted to provide the optimum therapeutic response. A therapeutically effective amount is also one in which any toxic or detrimental effects of the modulating agent are outweighed by the therapeutically beneficial effects. It is to be noted that dosage values may vary with the severity of the state to be alleviated. It is to be further understood that for any particular subject, specific dosage regimens should be adjusted over time according to the individual need and the professional judgment of the person administering or supervising the administration of the modulating agents.

A modulating agent can be administered to a subject by a variety of methods known in the art. The modulating agent can be provided in a manner such that it can be taken up by the cell or in a manner such that it can be converted to a form that can be readily taken up by the cell. In various embodiments, the modulating agent is administered in a formulation suitable for intravenous, intraperitoneal, subcutaneous, intramuscular, intravaginal, topical, transdermal or oral administration. The modulating agent is administered in a time release formulation (also referred to as a sustained-release formulation), for example in a composition which includes a slow release polymer, or a composition suitable for depot injection. The modulating agent can be prepared with carriers that will protect the inhibitor against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthocaters, polylactic acid and polylactic, polyglycolic copolymers (PLG). Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

When appropriately formulated, a modulating agent may be orally administered, for example, with an inert diluent or an assimilable edible carrier. The modulating agent may also be enclosed in a hard or soft shell gelatin capsule, compressed into tablets, or incorporated directly into the subject's diet. For oral therapeutic administration, the modulating agent may be incorporated with excipients and used in the form of ingestible tablets, buccal tablets, troches, capsules, elixirs, suspensions, syrups, wafers, and the like. The percentage of the modulating agent in the compositions and preparations may, of course, be varied. The amount of the modulating agent in such therapeutically useful compositions is such that a suitable dosage will be obtained.

To administer a modulating agent by other than parenteral administration, it may be necessary to coat the compound with, or co-administer the compound with, a material to prevent its inactivation. For example, the modulating agent may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. 1984. J. Neuroinmunol. 7:27). Pharmaceutically acceptable carriers include sterile aqueous solutions or dispersions and sterile powders for the extemporaneous preparation of sterile injectable solutions or dispersion The use of such media and agents for pharmaceutically active substances is well known in the art. Except insofar as any conventional media or agent is incompatible with the active compound, use thereof in the pharmaceutical compositions of the invention is contemplated.

Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

Prolonged absorption of the injectable compositions can be brought about by including in the composition an agent which delays absorption, for example, monostearate salts and gelatin. Sterile injectable solutions can be prepared by incorporating the modulating agent in the required amount in an appropriate solvent with one or a combination of ingredients enumerated above, as required, followed by filtered sterilization. Generally, dispersions are prepared by incorporating the modulating agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the modulating agent and the particular therapeutic effect to be achieved, and (b) the limitations inherent in the art of compounding such a modulating agent for the treatment of states described herein.

Other Uses

The proteins of the present invention and in particular their motor domains can be used for separation of a specific ligand from a heterologous mixtures in aqueous solution as described by Stewart (U.S. Pat. No. 5,830,659. In the system discussed by Stewart, a motor domain is linked to a ligand binding moiety, such as streptavidin. The chimeric proteins are placed into a loading chamber containing the heterogeneous mixtures which is coupled to a receiving chamber by a channel bearing immobilized, aligned microtubules. Addition of ATP to the loading chamber results in translocation of the motor domains, now attached non-covalently to the desired ligand via their ligand binding moiety, from the loading chamber to the receiving chamber. Hence, the ATP-driven motility activity of the motor domain results in separation of the desired ligand from the heterogeneous mixture.

The proteins of the invention and in particular their motor domains can also be used in the field of nanotechnology. Molecular motors have widespread application in the construction of nanoscale machines. Biomolecular motors have real-world application in the emerging nanotechnical arts. For example, a 1999 NASE study identifies multiple applications for nanoscale motors in the aerospace field. Motor domains can be used in the construction of rotors and other mechanical components (for review see Limberis and Stewart, Nanotechnology 11:47-51(2000)) as well as light-operated molecular shuttles useful for nanoscale switches and pumps.

Polynucleotides of the invention are also useful for inclusion on a GeneChip™ array or the like for use in expression monitoring (see U.S. Pat. No. 6,040,138,. EP 853, 679 and WO97/27317). Such arrays typically contain oligonucleotide or cDNA probes to allow detection of large numbers of mRNAs within a mixture. Many of the nucleic acids included in such arrays are from genes or ESTs that have not been well characterized. Such arrays are often used to compare expression profiles between different tissues or between different conditions of the same tissue (healthy vs. diseased or drug-treated vs. control) to identify differentially expressed transcripts. The differentially expressed transcripts are then useful e.g., for diagnosis of disease states, or to characterize responses of drugs. The nucleic acids of the invention can be included on GeneChip™ arrays or the like together with probes containing a variety of other genes.

All publications cited herein are incorporated by reference as if they were copied verbatim into the specification.

The foregoing disclosure contain examples which are given to illustrate the invention, but are not to be limiting thereof. All percentages given throughout the specification are based upon weight unless otherwise indicated. All protein molecular weights are based on mean average molecular weights unless otherwise indicated.

What is claimed is:

1. An isolated nucleic acid encoding a polypeptide, wherein the polypeptide has the following properties: (i) the polypeptide's activity includes (a) ATPase function and (b) the ability to bind actin; and (ii) the polypeptide comprises the amino acid sequence of SEQ ID NO:15 and has at least 98% sequence identity with SEQ ID NO:4 as measured using a sequence comparison algorithm.

2. An isolated nucleic acid of claim 1, wherein the polypeptide specifically binds to polyclonal antibodies generated against a protein comprising SEQ ID NO:4.

3. An isolated nucleic acid encoding a polypeptide, wherein the polypeptide has the following properties: the polypeptide's activity includes at least one of (a) ATPase function and (b) the ability to bind actin, wherein the nucleic acid encodes SEQ ID NO:4.

4. An isolated nucleic acid encoding a polypeptide, wherein the polypeptide has the following properties: the polypeptide's activity includes at least one of (a) ATPase function and (b) the ability to bind actin, wherein the nucleic acid comprises the nucleotide sequence of SEQ ID NO:3.

5. An isolated nucleic acid of claim 1, wherein the nucleic acid selectively hybridizes under stringent hybridization conditions to a nucleic acid having a sequence complementary to SEQ ID NO:3, wherein the stringent hybridization conditions employ 50% formamide, 5×SSC, 50 mM sodium phosphate (pH 6.8), 0.1% sodium pyrophosphate, 5×Denhardt's solution, 50 μg/ml sonicated salmon sperm DNA, 0.1% SDS, and 10% dextran sulfate at 42° C., with washes at 42° C. in 0.2×SSC and 50% formamide at 55° C., followed by a high-stringency wash consisting of 0.1×SSC containing EDTA at 55° C.

6. An expression vector comprising a nucleic acid encoding a polypeptide, wherein the polypeptide has the following properties: (i) the polypeptide's activity includes (a) ATPase function and (b) the ability to bind actin; and (ii) the polypeptide comprises the amino acid sequence of SEQ ID NO:15 and has at least 98% amino acid sequence identity to SEQ ID NO:4 as measured using a sequence comparison algorithm.

7. An isolated host cell transfected with the vector of claim 6.

* * * * *